United States Patent
Espie et al.

(10) Patent No.: US 11,780,927 B2
(45) Date of Patent: Oct. 10, 2023

(54) ANTI-CD40 ANTIBODIES FOR USE IN PREVENTION OF GRAFT REJECTION

(71) Applicant: NOVARTIS AG, Basel (CH)

(72) Inventors: Pascal Espie, Saint Louis (FR); Boerje Haraldsson, Basel (CH); James Rush, Thalwil (CH)

(73) Assignee: NOVARTIS AG, Basel (CH)

( * ) Notice: Subject to any disclaimer, the term of this patent is extended or adjusted under 35 U.S.C. 154(b) by 189 days.

(21) Appl. No.: 17/046,684

(22) PCT Filed: Apr. 11, 2019

(86) PCT No.: PCT/IB2019/052976
§ 371 (c)(1),
(2) Date: Oct. 9, 2020

(87) PCT Pub. No.: WO2019/198019
PCT Pub. Date: Oct. 17, 2019

(65) Prior Publication Data
US 2021/0079107 A1    Mar. 18, 2021

Related U.S. Application Data

(60) Provisional application No. 62/657,172, filed on Apr. 13, 2018.

(30) Foreign Application Priority Data

Nov. 26, 2018  (EP) ..................................... 18208332

(51) Int. Cl.
*C07K 16/28* (2006.01)
*A61P 37/06* (2006.01)

(52) U.S. Cl.
CPC .......... *C07K 16/2878* (2013.01); *A61P 37/06* (2018.01); *C07K 2317/56* (2013.01)

(58) Field of Classification Search
None
See application file for complete search history.

(56) References Cited

U.S. PATENT DOCUMENTS

| 8,828,396 B2 * | 9/2014 | Heusser | C07K 16/2866 424/152.1 |
| 9,221,913 B2 * | 12/2015 | Heusser | C07K 16/2875 |

FOREIGN PATENT DOCUMENTS

| WO | 2006073443 A2 | 7/2006 |
| WO | 2012065950 A1 | 5/2012 |

OTHER PUBLICATIONS

Rudikoff et al. Proc Natl Acad Sci USA 79: 1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14:2784-2794(1995). (Year: 1995).*
DAngelo et al., Many Routes to an Antibody Heavy-Chain CDR3: Necessary, Yet Insufficient, for Specific Binding (Frontiers in Immunology vol. 9, Article 395 Mar. 2018; doi:10.3389/fimmu.2018.00395, (Year: 2018).*
Piche-Nicholas et al., Changes in complementarity-determining regions significantly alter IgG binding to the neonatal Fc receptor (FcRN) and pharmacokinetics; MABS 2018, vol. 10, No. 1, 81-94, doi.org/10.1080/19420862.2017.1389355. (Year: 2018).*
Vonderheide et al.,(Clin Cancer Res 19: 1035-1043 (2013). (Year: 2013).*
Van Vugt et al., Expert Opinion on Investigational Drugs 31(10): 1087-1100 (Year: 2022).*
Cordoba et al., "A Novel, Blocking, Fc-Silent Anti-CD40 Monoclonal Antibody Prolongs Nonhuman Primate Renal Allograft Survival in the Absence of B Cell Depletion : Novel CD40 mAb Prolongs Allograft Survival", American Journal of Transplantation, 159(11):2825-2836 (2015).
Byrd et al., "Phase I study of the anti-CD40 humanized monoclonal antibody lucatumumab (HCD122) in relapsed chronic lymphocytic leukemia", Leukemia and Lymphoma, 53(11:2136-2142 (2012).
Harlan et al., "Efficacy and safety of bleselumab in kidney transplant recipients: A phase 2, randomized, open-label, noninferiority study", Am J. Transplant., 20:159-171 (2020).

* cited by examiner

*Primary Examiner* — Phuong Huynh
(74) *Attorney, Agent, or Firm* — David Goetz

(57) ABSTRACT

The disclosure relates to methods, treatment regimens, uses, kits and therapies for preventing graft rejection in solid organ transplantation, by employing anti-CD40 antibodies.

4 Claims, 17 Drawing Sheets

Specification includes a Sequence Listing.

SEQUENCE LISTING

<160> NUMBER OF SEQ ID NOS: 19

<210> SEQ ID NO 1
<211> LENGTH: 5
<212> TYPE: PRT
<213> ORGANISM: Homo sapiens

<400> SEQUENCE: 1

Ser Tyr Gly Met His
1               5

<210> SEQ ID NO 2
<211> LENGTH: 17
<212> TYPE: PRT
<213> ORGANISM: Homo sapiens

<400> SEQUENCE: 2

Val Ile Ser Tyr Glu Glu Ser Asn Arg Tyr His Ala Asp Ser Val Lys
1               5                   10                  15

Gly

<210> SEQ ID NO 3
<211> LENGTH: 11
<212> TYPE: PRT
<213> ORGANISM: Homo Sapiens

<400> SEQUENCE: 3

Asp Gly Gly Ile Ala Ala Pro Gly Pro Asp Tyr
1               5                   10

<210> SEQ ID NO 4
<211> LENGTH: 16
<212> TYPE: PRT
<213> ORGANISM: Homo sapiens

<400> SEQUENCE: 4

Arg Ser Ser Gln Ser Leu Leu Tyr Ser Asn Gly Tyr Asn Tyr Leu Asp
1               5                   10                  15

<210> SEQ ID NO 5
<211> LENGTH: 7
<212> TYPE: PRT
<213> ORGANISM: Homo sapiens

<400> SEQUENCE: 5

Leu Gly Ser Asn Arg Ala Ser
1               5

<210> SEQ ID NO 6
<211> LENGTH: 9
<212> TYPE: PRT
<213> ORGANISM: Homo sapiens

<400> SEQUENCE: 6

Met Gln Ala Arg Gln Thr Pro Phe Thr
1               5

<210> SEQ ID NO 7
<211> LENGTH: 120
<212> TYPE: PRT
<213> ORGANISM: Homo sapiens

<400> SEQUENCE: 7

Gln Val Gln Leu Val Glu Ser Gly Gly Gly Val Val Gln Pro Gly Arg

```
                1               5                    10                   15
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Glu Glu Ser Asn Arg Tyr His Ala Asp Ser Val
            50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
                100                 105                 110

Gly Thr Leu Val Thr Val Ser Ser
            115                 120
```

<210> SEQ ID NO 8
<211> LENGTH: 112
<212> TYPE: PRT
<213> ORGANISM: Homo sapeins

<400> SEQUENCE: 8

```
Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
            35                  40                  45

Pro Gln Val Leu Ile Ser Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
                100                 105                 110
```

<210> SEQ ID NO 9
<211> LENGTH: 450
<212> TYPE: PRT
<213> ORGANISM: Homo sapiens

<400> SEQUENCE: 9

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Glu Glu Ser Asn Arg Tyr His Ala Asp Ser Val
            50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
```

```
            100                 105                 110
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 10
<211> LENGTH: 219
<212> TYPE: PRT
<213> ORGANISM: Homo sapiens

<400> SEQUENCE: 10

Asp Ile Val Met Thr Gln Ser Pro Leu Ser Leu Thr Val Thr Pro Gly
1               5                   10                  15
```

-continued

```
Glu Pro Ala Ser Ile Ser Cys Arg Ser Ser Gln Ser Leu Leu Tyr Ser
             20                  25                  30

Asn Gly Tyr Asn Tyr Leu Asp Trp Tyr Leu Gln Lys Pro Gly Gln Ser
         35                  40                  45

Pro Gln Val Leu Ile Ser Leu Gly Ser Asn Arg Ala Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                 85                  90                  95

Arg Gln Thr Pro Phe Thr Phe Gly Pro Gly Thr Lys Val Asp Ile Arg
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 450
<212> TYPE: PRT
<213> ORGANISM: Homo sapiens

<400> SEQUENCE: 11

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Glu Glu Ser Asn Arg Tyr His Ala Asp Ser Val
     50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                 85                  90                  95

Ala Arg Asp Gly Gly Ile Ala Ala Pro Gly Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 12
<211> LENGTH: 219
<212> TYPE: PRT
<213> ORGANISM: Homo sapiens

<400> SEQUENCE: 12

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

```
                        85                  90                  95
Arg Gln Thr Pro Phe Thr Phe Gly Pro Gly Thr Lys Val Asp Ile Arg
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 13
<211> LENGTH: 217
<212> TYPE: PRT
<213> ORGANISM: Homo sapiens

<400> SEQUENCE: 13

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 14
<211> LENGTH: 217
```

<212> TYPE: PRT
<213> ORGANISM: Homo sapiens

<400> SEQUENCE: 14

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ala Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 15
<211> LENGTH: 1350
<212> TYPE: DNA
<213> ORGANISM: Homo sapiens

<400> SEQUENCE: 15

```
caggtgcagc tggtggaatc tggcggcgga gtggtgcagc ctggccggtc cctgagactg     60
tcttgcgccg cctccggctt caccttctcc agctacggca tgcactgggt cgacaggcc    120
cctggcaagg gactggaatg ggtggccgtg atctcctacg aggaatccaa cagataccac    180
gctgactccg tgaagggccg gttcacaatc tcccgggaca ctccaagat caccctgtac    240
ctgcagatga actccctgcg gaccgaggac accgccgtgt actactgcgc cagggacgga    300
ggaatcgccg ctcctggacc tgattattgg ggccagggca cctggtgac agtgtcctcc    360
gctagcacca agggcccctc cgtgttccct ctggcccct ccagcaagtc cacctctggc    420
ggcaccgccg ctctgggctg cctggtgaaa gactacttcc ccgagcccgt gaccgtgtcc    480
tggaactctg gcgccctgac ctccggcgtg cacacctttc agccgtgct gcagtcctcc    540
ggcctgtact ccctgtcctc cgtggtgacc gtgccctcta gctctctggg cacccagacc    600
tacatctgca acgtgaacca caagccctcc aacaccaagg tggacaagcg ggtgaacccc    660
aagtcctgcg acaagaccca cacctgtccc ccctgccctg cccctgaact gctgggcgga    720
```

| | |
|---|---|
| ccttccgtgt tcctgttccc cccaaagccc aaggacaccc tgatgatctc ccggacccccc | 780 |
| gaagtgacct gcgtggtggt ggacgtgtcc cacgaggacc ctgaagtgaa gttcaattgg | 840 |
| tacgtggacg gcgtggaagt gcacaacgcc aagaccaagc ccagagagga acagtacgcc | 900 |
| tccacctacc gggtggtgtc tgtgctgacc gtgctgcacc aggactggct gaacggcaaa | 960 |
| gagtacaagt gcaaggtctc caacaaggcc ctgcctgccc ccatcgaaaa gaccatctcc | 1020 |
| aaggccaagg gccagccccg cgagccacag gtgtacacac tgcccccccag ccgggaagag | 1080 |
| atgaccaaga accaggtgtc cctgacctgt ctggtcaaag gcttctaccc ctccgatatc | 1140 |
| gccgtggagt gggagtccaa cggacagccc gagaacaact acaagaccac cccccctgtg | 1200 |
| ctggactccg acggctcatt cttcctgtac tccaagctga ccgtggacaa gtcccggtgg | 1260 |
| cagcagggca acgtgttctc ctgctccgtg atgcacgagg ccctgcacaa ccactacacc | 1320 |
| cagaagtccc tgtccctgag ccccggcaag | 1350 |

<210> SEQ ID NO 16
<211> LENGTH: 657
<212> TYPE: DNA
<213> ORGANISM: Homo sapiens

<400> SEQUENCE: 16

| | |
|---|---|
| gacatcgtga tgacccagtc cccctgtcc ctgaccgtga cacctggcga gcctgcctct | 60 |
| atctcctgca gatcctccca gtccctgctg tactccaacg gctacaacta cctggactgg | 120 |
| tatctgcaga agcccggcca gtccccacag gtgctgatct ccctgggctc caacagagcc | 180 |
| tctggcgtgc ccgaccggtt ctccggctct ggctctggca ccgacttcac actgaagatc | 240 |
| tcacgggtgg aagccgagga cgtgggcgtg tactactgca tgcaggcccg gcagacccccc | 300 |
| ttcaccttcg gccctggcac caaggtggac atcggcgta cggtggccgc tcccagcgtg | 360 |
| ttcatcttcc cccccagcga cgagcagctg aagagcggca ccgccagcgt ggtgtgcctg | 420 |
| ctgaacaact tctaccccccg ggaggccaag gtgcagtgga aggtggacaa cgccctgcag | 480 |
| agcggcaaca gccaggagag cgtcaccgag caggacagca aggactccac ctacagcctg | 540 |
| agcagcaccc tgaccctgag caaggccgac tacgagaagc ataaggtgta cgcctgcgag | 600 |
| gtgacccacc agggcctgtc cagccccgtg accaagagct tcaacagggg cgagtgc | 657 |

<210> SEQ ID NO 17
<211> LENGTH: 1350
<212> TYPE: DNA
<213> ORGANISM: Homo sapiens

<400> SEQUENCE: 17

| | |
|---|---|
| caggtgcagc tggtggaatc tggcggcgga gtggtgcagc tggccggtc cctgagactg | 60 |
| tcttgcgccg cctccggctt caccttctcc agctacggca tgcactgggt gcgacaggcc | 120 |
| cctggcaagg gactgaatg ggtggccgtg atctcctacg aggaatccaa cagataccac | 180 |
| gctgactccg tgaagggccg gttcacaatc tcccgggaca actccaagat caccctgtac | 240 |
| ctgcagatga actccctgcg gaccgaggac accgccgtgt actactgcgc cagggacgga | 300 |
| ggaatcgccg ctcctggacc tgattattgg ggccagggca ccctggtgac agtgtcctcc | 360 |
| gctagcacca agggcccctc cgtgttccct ctggcccccct ccagcaagtc cacctctggc | 420 |
| ggcaccgccg ctctgggctg cctggtgaaa gactacttcc ccgagcccgt gaccgtgtcc | 480 |
| tggaactctg gcgccctgac ctccggcgtg cacacctttc cagccgtgct gcagtcctcc | 540 |
| ggcctgtact cccctgtcctc cgtggtgacc gtgccctcta gctctctggg cacccagacc | 600 |

```
tacatctgca acgtgaacca caagccctcc aacaccaagg tggacaagcg ggtggaaccc      660
aagtcctgcg acaagaccca cacctgtccc ccctgccctg ccctgaact gctgggcgga       720
ccttccgtgt tcctgttccc cccaaagccc aaggacaccc tgatgatctc ccggacccc       780
gaagtgacct gcgtggtggt ggccgtgtcc acgaggacc ctgaagtgaa gttcaattgg       840
tacgtggacg gcgtggaagt gcacaacgcc aagaccaagc ccagagagga acagtacaac      900
tccacctacc gggtggtgtc tgtgctgacc gtgctgcacc aggactggct gaacggcaaa     960
gagtacaagt gcaaggtctc caacaaggcc ctgcctgccc ccatcgaaaa gaccatctcc     1020
aaggccaagg gccagccccg cgagccacag gtgtacacac tgcccccag ccgggaagag       1080
atgaccaaga accaggtgtc cctgacctgt ctggtcaaag gcttctaccc ctccgatatc     1140
gccgtggagt gggagtccaa cggacagccc gagaacaact acaagaccac ccccctgtg      1200
ctggactccg acggctcatt cttcctgtac tccaagctga ccgtggacaa gtcccggtgg     1260
cagcagggca acgtgttctc ctgctccgtg atgcacgagg ccctgcacaa ccactacacc     1320
cagaagtccc tgtccctgag ccccggcaag                                      1350
```

<210> SEQ ID NO 18
<211> LENGTH: 657
<212> TYPE: DNA
<213> ORGANISM: Homo sapiens

<400> SEQUENCE: 18

```
gacatcgtga tgacccagtc ccccctgtcc ctgaccgtga cacctggcga gcctgcctct      60
atctcctgca gatcctccca gtccctgctg tactccaacg gctacaacta cctggactgg     120
tatctgcaga agcccggcca gtccccacag gtgctgatct ccctgggctc aacagagcc      180
tctggcgtgc ccgaccggtt ctccggctct ggctctggca ccgacttcac actgaagatc     240
tcacgggtgg aagccgagga cgtgggcgtg tactactgca tgcaggcccg gcagaccccc     300
ttcaccttcg gccctggcac caaggtggac atccggcgta cggtggccgc tcccagcgtg     360
ttcatcttcc cccccagcga cgagcagctg aagagcggca ccgccagcgt ggtgtgcctg     420
ctgaacaact ctacccccg gggaggccaag gtgcagtgga aggtggacaa cgccctgcag     480
agcggcaaca gccaggagag cgtcaccgag caggacagca aggactccac ctacagcctg     540
agcagcaccc tgaccctgag caaggccgac tacgagaagc ataaggtgta cgcctgcgag     600
gtgacccacc agggcctgtc cagccccgtg accaagagct caacagggg cgagtgc         657
```

<210> SEQ ID NO 19
<211> LENGTH: 277
<212> TYPE: PRT
<213> ORGANISM: Homo sapiens

<400> SEQUENCE: 19

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

-continued

```
Lys Tyr Cys Asp Pro Asn Leu Gly Leu Arg Val Gln Gln Lys Gly Thr
            85                  90                  95
Ser Glu Thr Asp Thr Ile Cys Thr Cys Glu Glu Gly Trp His Cys Thr
            100                 105                 110
Ser Glu Ala Cys Glu Ser Cys Val Leu His Arg Ser Cys Ser Pro Gly
            115                 120                 125
Phe Gly Val Lys Gln Ile Ala Thr Gly Val Ser Asp Thr Ile Cys Glu
            130                 135                 140
Pro Cys Pro Val Gly Phe Phe Ser Asn Val Ser Ser Ala Phe Glu Lys
145                 150                 155                 160
Cys His Pro Trp Thr Ser Cys Glu Thr Lys Asp Leu Val Val Gln Gln
                165                 170                 175
Ala Gly Thr Asn Lys Thr Asp Val Val Cys Gly Pro Gln Asp Arg Leu
            180                 185                 190
Arg Ala Leu Val Val Ile Pro Ile Ile Phe Gly Ile Leu Phe Ala Ile
            195                 200                 205
Leu Leu Val Leu Val Phe Ile Lys Lys Val Ala Lys Lys Pro Thr Asn
    210                 215                 220
Lys Ala Pro His Pro Lys Gln Glu Pro Gln Glu Ile Asn Phe Pro Asp
225                 230                 235                 240
Asp Leu Pro Gly Ser Asn Thr Ala Ala Pro Val Gln Glu Thr Leu His
                245                 250                 255
Gly Cys Gln Pro Val Thr Gln Glu Asp Gly Lys Glu Ser Arg Ile Ser
            260                 265                 270
Val Gln Glu Arg Gln
            275
```

ANTI-CD40 ANTIBODIES FOR USE IN PREVENTION OF GRAFT REJECTION

CROSS-REFERENCE TO RELATED APPLICATIONS

This is an application under 35 U.S.C. 371 of PCT Application No. PCT/IB2019/052976, which was filed on Apr. 11, 2019, which claims priority to U.S. Provisional Application No. 62/657,172, which was filed on Apr. 13, 2018, and European Patent Application No. 18208332.9, which was filed on Nov. 26, 2018, each of which are herein incorporated by reference in their entireties.

TECHNICAL FIELD

The disclosure relates to methods, treatment regimens, uses, kits and therapies for prevention of graft rejection in solid organ transplantation, by employing anti-CD40 antibodies, such as CFZ533.

BACKGROUND OF THE DISCLOSURE

CD40 is a transmembrane glycoprotein constitutively expressed on B cells and antigen presenting cells (APCs) such as monocytes, macrophages, and dendritic cells (DC).

CD40 is also expressed on platelets, and under certain conditions can be expressed on eosinophils, and parenchymal cells. The ligand for CD40 (CD154, CD40 ligand or CD40L), is inducible on a variety of cell types including activated T cells, platelets, and B cells.

Binding of CD154 to CD40 induces signaling via NF-κB, and MAPK pathways resulting in a variety of cell-type dependent activation outcomes. For example, signaling via this pathway is essential for several important effector functions of the adaptive immune system including primary T-cell-dependent antibody responses (TDARs), B cell proliferation, germinal center (GC) formation, immunoglobulin (Ig) isotype switching, somatic mutation, and differentiation of memory B and plasma cells. In addition to effects on B cells, CD40 pathway activation provides important signals for DC maturation and function, as well as monocyte and macrophage survival and cytokine secretion. More recently, CD40-CD154 pathway signaling has been implicated in the function of parenchymal cells in inflamed tissue, with activated epithelial cells from kidney, salivary gland and skin producing chemokines in response to CD40 ligation.

The diversity of cell types that express CD40 as well as the variety of effector functions downstream of CD40-CD154 interactions suggests that targeting this pathway could have therapeutic potential in various indications. In support of this notion, inhibition of this costimulatory pathway using receptor or ligand blocking antibodies improved autoimmune disease pathology and prolonged allograft survival in preclinical models. In addition, use of anti-CD154 antibodies has shown benefit in patients with Systemic Lupus Erythematosus (SLE) and Immune Thrombocytopenic Purpura (ITP). Unfortunately, treatment with anti-CD154 antibodies provoked thromboembolic events in the clinic as well as in non-human primates (NHPs).

Over the past decades, organ allotransplantation has become a common medical procedure with considerable impact on extending and improving the quality of life of patients with end stage renal, cardiac, hepatic or pulmonary failure. To maximize efficacy and minimize adverse effects, current immunosuppressant (IS) regimens use combinations of IS drugs. Care is taken to achieve synergy or additive immunosuppressive effects via the administration of submaximal doses of individual agents with different mechanism of actions while avoiding overlapping toxicities. Most treatment regimens today include two or more primary and adjunct IS with or without an induction agent. Induction agents are administered during the first hours to days post transplantation to suppress the recipient's immune system and priming of an immune response to the allograft while the other IS agents are reaching effective concentrations. Induction agents include the anti-CD25 mAb basiliximab (Simulect®, Novartis) or polyclonal anti-T cell globulin (Thymoglobulin®, rabbit ATG, rATG, Genzyme). In highly sensitized patients, induction with an anti-CD52 mAb, alemtuzumab (Campath®, Sanofi-Aventis S A) which leads to long-term lymphocyte depletion has been used. Within 1-2 days following transplant, the maintenance treatment regimen is initiated with two or more of the following agents: a calcineurin inhibitor (CNI) such as cyclosporine (CsA, Neoral®, Novartis) or tacrolimus (Tac, FK506, Prograf®, Astellas), together with a lymphocyte proliferation inhibitor such as mycophenolic acid (MPA; Myfortic®, Novartis) or mycophenolate mofetil (MMF; CellCept®, Roche) or proliferation signal inhibitor such as everolimus (Zortress®, Certican®, Novartis) or sirolimus (Rapamune®, Pfizer). More recently, the T cell co-stimulation blocker belatacept Nulojix®, BMS), a fusion protein, demonstrated the potential of a biologic agent to replace CNIs in a calcineurin-free treatment regimen with MPA.

Although the current standard-of-care regimens provide excellent short-term efficacy with very low acute rejection rates, there is still an opportunity to increase long-term graft and patient survival. The current rate of renal allograft graft survival in the first year and 5 years post-transplant is 95% and 68% (Matas et al 2013), respectively, with a rapid decline thereafter. The estimated glomerular filtration rate at 12 months has been strongly associated with subsequent graft failure (Kasiske et al 2011). As such, kidney allograft function is also an important predictor of graft survival. Other factors, such as donor age, acute rejection and vascular remodeling may also play a role in overall graft survival, but the nephrotoxic effects of calcineurin inhibitors are directly associated with irreversible renal function deterioration (Naesens et al 2009). By eliminating CNIs from the treatment regimen, mechanism-based side effects, such as nephrotoxicity, hypertension, dyslipidemia, neurotoxicity, gastrointestinal and hematological toxicity, and/or diabetogenic effects may be minimized or eliminated. In the search for novel therapeutics, there has been an increasing interest in the role B cells, plasma cells and antibodies play in the immune response to an allograft, specifically acute cellular rejection and chronic humoral or antibody mediated rejection (Clatworthy 2011). By developing a specific treatment that decreases the priming of T and B cells and subsequent production of donor specific antibodies and eliminating CNIs, it is hypothesized that chronic rejection can be minimized and long-term graft survival may be increased. Hence, there is a significant need for new immunosuppressant agents.

CFZ533 is a human monoclonal antibody directed against human CD40. It belongs to the IgG1 isotype subclass with and comprises an Fc-silencing mutation (N297A) which abolishes FcγR binding and associated effector functions like ADCC and CDC. CFZ533 is disclosed in U.S. Pat. Nos. 8,828,396 and 9,221,913, incorporated herein by reference.

SUMMARY OF THE DISCLOSURE

It has been found that human, anti-CD40 monoclonal antibodies with silenced ADCC activity are suitable treatment or prevention of a disease related with CD40-CD154 pathway signaling, such as for the prevention of graft rejection in solid organ transplantation. Particularly, the antibody CFZ533 has in a proof of concept study shown promise of offering a new treatment modality prevention of graft rejection in solid organ transplantation.

In the detailed description, several specific examples are provided describing the characterization of the functional properties of CFZ533 in CD40-pathway relevant in vitro and in vivo model systems as well as investigating the relationship between CFZ533 exposure and PD effects.

According to a first aspect of the invention an anti-CD40 antibody for use in treatment or prevention of a disease related to CD40-CD154 pathway signaling is provided.

In a preferred embodiment, an anti-CD40 antibody for use in the prevention of graft rejection in solid organ transplantation is provided.

The solid organ transplantation may be kidney transplantation or liver transplantation.

The solid organ transplantation may be kidney transplantation, liver transplantation, heart transplantation, lung transplantation, pancreas transplantation, intestine transplantation or composite tissue transplantation.

The antibody may be selected from the group consisting of:

a. an anti-CD40 antibody comprising an immunoglobulin VH domain comprising the amino acid sequence of SEQ ID NO: 7 and an immunoglobulin VL domain comprising the amino acid sequence of SEQ ID NO: 8;

b. an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;

c. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;

d. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14; and e. an anti-CD40 antibody comprising a silent Fc IgG1 region, or amino acid mutations that render the antibody unable to mediate cell depletion.

The antibody may comprise the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

In one embodiment, a pharmaceutical composition is provided comprising a therapeutically effective amount of the antibody for use according to the first aspect and one or more pharmaceutically acceptable carriers.

In one embodiment, the route of administration is subcutaneous or intravenous of the antibody according to the first aspect, or a combination of subcutaneous or intravenous.

The dose may be adjusted so that plasma or serum concentration of antibody is at least 40 µg/mL.

The dose may be above 3 mg active ingredient per kilogram of human subject (mg/kg), such as above or equal to 10 mg/kg, above or equal to 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg or 30 mg/kg.

In one embodiment, the dose is about 3 mg to about 30 mg active ingredient per kilogram of a human subject, such as about 3 mg to about 30 mg active ingredient per kilogram when administered intravenously (IV).

In one embodiment, the dose is about 10 mg active ingredient per kilogram of a human subject, such as about 10 mg active ingredient per kilogram IV.

In one embodiment, the dose is about 150 mg to about 600 mg active ingredient, such as about 150 mg to about 600 mg when administered subcutaneously (SC).

In one embodiment, the dose is about 300 mg or 450 mg active ingredient, such as about 300 mg or 450 mg SC.

In one embodiment, the antibody is administered through a first loading dosing and a second maintenance dosing.

In one embodiment, the loading dosing consists of one, two, three or four weekly intravenous or subcutaneous injections of a first dose and the maintenance dosing consists of weekly or biweekly subcutaneous injections of a second dose, and wherein the first dose is higher than the second dose.

In one embodiment, the first dose is between about 300 mg and about 600 mg, and the second dose is about 300 mg, about 450 mg or about 600 mg.

In one embodiment, the loading dosing consists of one or two intravenous administration of a first dose and the maintenance dosing consists of weekly or biweekly subcutaneous injections of a second dose.

In one embodiment, the first dose is about 10 mg/kg or about 30 mg/kg and the second dose is between about 300 mg and 600 mg.

According to a second aspect, a method of treatment or prevention of a disease related with CD40-CD154 pathway signaling is provided.

In a preferred embodiment, a method of preventing graft rejection in solid organ transplantation in a human subject is provided, comprising administering a therapeutically effective dose of anti-CD40 antibody to said subject.

The solid organ transplantation may be kidney transplantation or liver transplantation. In another embodiment, the solid organ transplantation may be kidney transplantation, liver transplantation, heart transplantation, lung transplantation, pancreas transplantation, intestine transplantation or composite tissue transplantation.

In one embodiment the antibody is selected from the group consisting of:

a. an anti-CD40 antibody comprising an immunoglobulin VH domain comprising the amino acid sequence of SEQ ID NO: 7 and an immunoglobulin VL domain comprising the amino acid sequence of SEQ ID NO: 8;

b. an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;

c. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;

d. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14; and e. an anti-CD40 antibody comprising a silent Fc IgG1 region.

In one embodiment, the antibody comprises the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

In one embodiment, the antibody is administered together with one or more pharmaceutically acceptable carriers.

In one embodiment, the antibody is administered subcutaneously or intravenously, or a combination of subcutaneous or intravenous.

In one embodiment, the antibody is administered so that plasma or serum concentration of antibody is at least 40 µg/mL.

The dose may be above 3 mg active ingredient per kilogram of human subject (mg/kg), such as above or equal to 10 mg/kg, above or equal to 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg or 30 mg/kg.

In one embodiment, the antibody is administered as a dose of about 3 mg to about 30 mg active ingredient per kilogram of a human subject, such as about 3 mg to about 30 mg active ingredient per kilogram when administered intravenously (IV).

In one embodiment, the dose is about 10 mg active ingredient per kilogram of the human subject, such as about 10 mg active ingredient per kilogram IV.

In one embodiment, the antibody is administered as a dose of about 150 mg to about 600 mg active ingredient, such as about 150 mg to about 600 mg when administered subcutaneously (SC).

In one embodiment, the dose about 300 mg or 450 mg active ingredient, such as about 300 mg or 450 mg SC.

In one embodiment, the antibody is administered with a loading dosing and a maintenance dosing.

In one embodiment, the loading dosing consists of one, two, three or four weekly subcutaneous injections of a first dose and the maintenance dosing consists of weekly or biweekly subcutaneous injections of a second dose, and wherein the first dose is higher than the second dose.

In one embodiment, the first dose is between about 300 mg and about 600 mg and the second dose is about 300 mg, about 450 or about 600 mg.

In one embodiment, the loading dosing consists of one or two intravenous administration and the maintenance dosing consists of weekly or biweekly subcutaneous injections of a second dose.

In one embodiment, the first dose is about 10 mg/kg or about 30 mg/kg and the second dose is about 300 mg.

According to a third aspect, use of a liquid pharmaceutical composition comprising an anti-CD40 antibody, a buffer, a stabilizer and a solubilizer, and means for intravenously or subcutaneously administering the anti-CD40 antibody to a solid organ transplantation patient, for the manufacture of a medicament for the prevention of graft rejection in solid organ transplantation is provided, wherein the anti-CD40 antibody:

a. is to be intravenously or subcutaneously administered with a first loading dosing; and b. thereafter, with a second maintenance dosing, wherein the maintenance dose is different from the loading dose, and wherein said anti-CD40 antibody is selected from the group consisting of:

i. an anti-CD40 antibody comprising an immunoglobulin VH domain comprising the amino acid sequence of SEQ ID NO: 7 and an immunoglobulin VL domain comprising the amino acid sequence of SEQ ID NO: 8;

ii. an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;

iii. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;

iv. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14;

v. an anti-CD40 antibody comprising a silent Fc IgG1 region: and vi. an anti-CD40 antibody comprising the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

An additional aspect of the disclosure relates to the use of a liquid pharmaceutical composition comprising an anti-CD40 antibody, for the manufacture of a medicament for the prevention of graft rejection in solid organ transplantation, wherein the anti-CD40 antibody:

a. is to be intravenously or subcutaneously administered with a first loading dosing; and b. thereafter, with a second maintenance dosing, wherein the maintenance dose is different from the loading dose, and wherein said anti-CD40 antibody is selected from the group consisting of:

i. an anti-CD40 antibody comprising an immunoglobulin VH domain comprising the amino acid sequence of SEQ ID NO: 7 and an immunoglobulin VL domain comprising the amino acid sequence of SEQ ID NO: 8;

ii. an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;

iii. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;

iv. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14;

v. an anti-CD40 antibody comprising a silent Fc IgG1 region: and vi. an anti-CD40 antibody comprising the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

In a fourth embodiment the disclosure relates to CFZ533 for use in the treatment of solid organ transplant patients, wherein the treatment results in long-term prevention of graft rejection.

In a fives embodiment the disclosure relates to CFZ533 for use in the long-term prevention of graft loss in solid organ transplant patients.

In a sixed embodiment, the disclosure relates to CFZ533 for use in the treatment of solid organ transplant patients, wherein the treatment results in long term graft survival.

In a seventh embodiment the disclosure relates to CFZ533 for use according to embodiment four to six, wherein (i) the prevention of graft loss, (ii) absence of organ graft loss or (iii) the graft survival lasts for at least 3 years post transplantation.

In an eight embodiment the disclosure relates to CFZ533 for use according to embodiment four to seven, wherein the CFZ533 treatment occurs post-transplantation and the antibody is administered so that plasma or serum concentration of the antibody is at least 40 µg/mL.

In a ninth embodiment the disclosure relates to CFZ533 for use according to embodiment eight, wherein the antibody is administered as a dose of about 3 mg to about 30 mg active ingredient per kilogram of a human subject.

In a tenth embodiment the disclosure relates to CFZ533 for use according to embodiment nine, wherein the dose is about 10 mg active ingredient per kilogram of the human subject.

In an eleventh embodiment the disclosure relates to CFZ533 for use according to embodiment nine, wherein the antibody is administered as a dose of about 150 mg to about 600 mg active ingredient.

In a twelfth embodiment the disclosure relates to CFZ533 for use according to embodiment eleven, wherein the dose is about 300 mg, about 450 mg, or about 600 mg active ingredient.

In a thirteenth embodiment the disclosure relates to CFZ533 for use according to embodiment eight to twelve, wherein the antibody is administered with a loading dosing and a maintenance dosing.

In a fourteenth embodiment the disclosure relates to CFZ533 for use according to embodiment thirteen, wherein the loading dosing consists of one, two, three or four weekly subcutaneous injection(s) of a first dose and the maintenance dosing consists of weekly or biweekly subcutaneous injections of a second dose, and wherein the first dose is higher than the second dose.

In a fifteenth embodiment the disclosure relates to CFZ533 for use according to embodiment fourteen, wherein the first dose is between about 300 mg and about 600 mg and the second dose is about 300 mg, about 450 or about 600 mg.

In a sixteenth embodiment the disclosure relates to CFZ533 for use according to embodiment fifteen, wherein the loading dosing consists of one, two, three or four intravenous administration(s) of a first dose and the maintenance dosing consists of weekly subcutaneous injections of a second dose.

In a seventeenth embodiment the disclosure relates to CFZ533 for use according to embodiment sixteen, wherein the first dose is about 10 mg/kg and the second dose is about 300 mg, about 450 or about 600 mg active ingredient.

In an eighteenth embodiment the disclosure relates to a method of securing long-term graft survival in solid organ transplant patients, wherein the patients are treated with a therapeutically effective amount of CFZ533.

In a nineteenth embodiment the disclosure relates to a method of long-term prevention of graft loss in solid organ transplant patients, wherein the patients are treated with a therapeutically effective amount of CFZ533.

In a twentieth embodiment the disclosure relates to a method according to embodiment eighteen and nineteen, wherein the CFZ533 treatment occurs post-transplantation and the antibody is administered so that plasma or serum concentration of antibody is at least 40 µg/mL.

In a twenty-first embodiment the disclosure relates to a method according to embodiment twenty, wherein the antibody is administered as a dose of about 3 mg to about 30 mg active ingredient per kilogram of a human subject.

In a twenty-second embodiment the disclosure relates to a method according to the twenty-first embodiment, wherein the dose is about 10 mg active ingredient per kilogram of the human subject.

In a twenty-third embodiment the disclosure relates to a method according to the twenty-second embodiment, wherein the antibody is administered as a dose of about 150 mg to about 600 mg active ingredient.

In a twenty-forth embodiment the disclosure relates to a method according to the twenty-third embodiment, wherein the dose is about 300 mg, about 450 mg, or about 600 mg active ingredient.

In a twenty-fifth embodiment the disclosure relates to a method according to the twenty-forth embodiment, wherein the antibody is administered with a loading dosing and a maintenance dosing.

In a twenty-sixth embodiment the disclosure relates to a method according to the twenty-fifth embodiment, wherein the loading dosing consists of one, two, three or four weekly subcutaneous injection(s) of a first dose and the maintenance dosing consists of weekly or biweekly subcutaneous injections of a second dose, and wherein the first dose is higher than the second dose.

In a twenty-seventh embodiment the disclosure relates to a method according to the twenty-sixth embodiment, wherein the first dose is between about 300 mg and about 600 mg and the second dose is about 300 mg, about 450 or about 600 mg.

In a twenty-eighths embodiment the disclosure relates to a method according to the twenty-sixth embodiment, wherein the loading dosing consists of one, two, three or four intravenous administration(s) of a first dose and the maintenance dosing consists of weekly subcutaneous injections of a second dose.

In a twenty-ninth embodiment the disclosure relates to a method according to the twenty-eighths embodiment, wherein the first dose is about 10 mg/kg and the second dose is about 300 mg, about 450 or about 600 mg.

In a thirties embodiment the disclosure relates to CFZ533 for use according to embodiments four to seventeen or the methods according to embodiments eighteen to twenty-nine, wherein the solid organ transplantation is kidney transplantation, liver transplantation, heart transplantation, lung transplantation, pancreas transplantation, intestine transplantation or composite tissue transplantation

BRIEF DESCRIPTION OF THE FIGURES

FIG. 13 is a schematic presentation of the study design.

DETAILED DESCRIPTION OF THE DISCLOSURE

Figure 1:
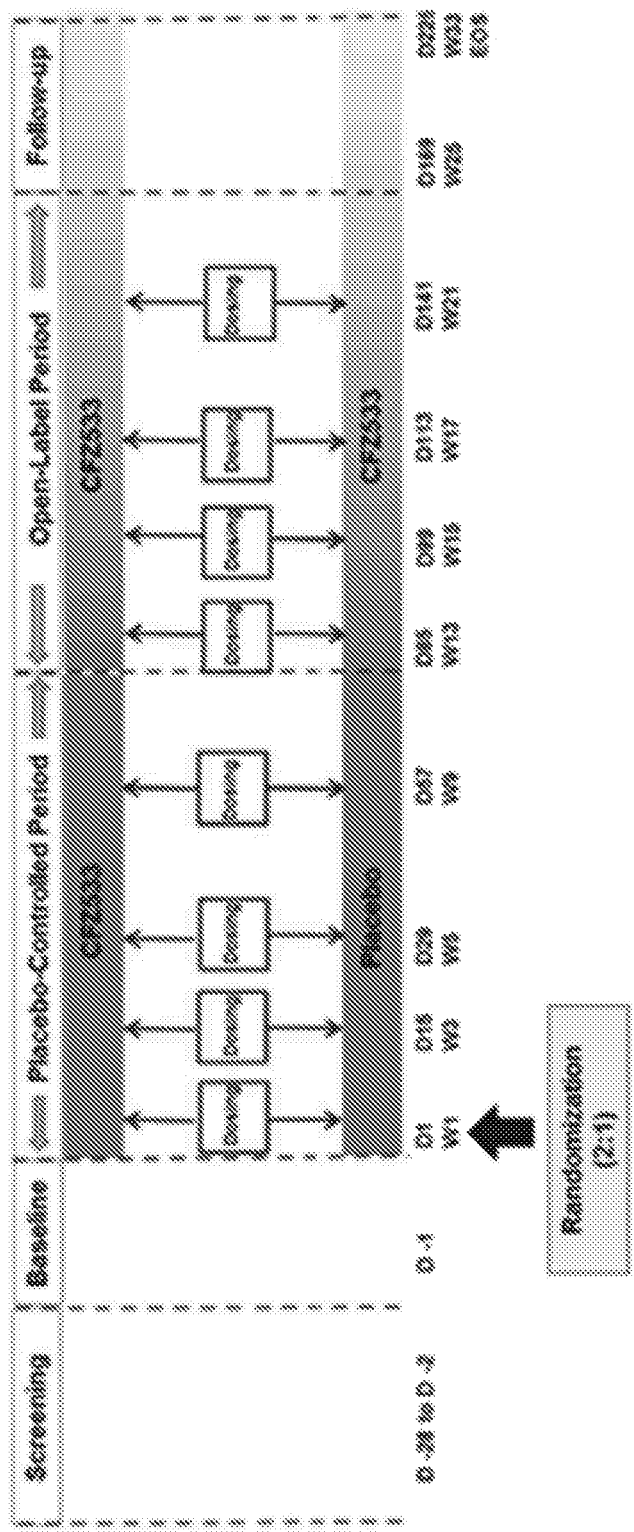
FIG. 1 is a schematic representation of the study design of a first and a second cohort of a comparative study.

The CD40-CD154 (CD154 is the CD40L) pathway is thought to play an important role in survival of grafts in solid organ transplantation.

Thus, any anti-CD40 monoclonal antibody capable of blocking CD40-CD154 signaling, such as an anti-CD40 antibody with silenced ADCC activity, could be suitable for the prevention of graft loss in solid organ transplantation.

Without wishing to be bound by theory, the inventors have identified that sustained plasma concentrations at least about 40 µg/mL of the CFZ533 antibody was necessary to block the CD40-CD40L pathway in target tissues in solid organ transplantation patients. Thus, with a dosing regimen providing, throughout the entire treatment period, sustained plasma concentrations of at least 40 µg/mL and up to 400 µg/mL, in situations where CD40 expression in affected tissues would be enhanced (severity of the condition, activation of the immune system post transplantation), is considered for a therapeutic effect. The observed maximum plasma concentration at steady state was about 400 µg/ml and was generally safe and well tolerated, with no major signal to suggest increased risk of infection. No thromboembolic events were observed.

The appropriate dosage will vary depending upon, for example, the particular CD40 pathway antagonist, e.g. an anti-CD40 antibody or antigen binding fragment thereof (e.g., mAb1, also called CFZ533 herein, mAb2, ASKP1240) or anti-CD40L antibody (e.g. BIIB063) or antigen-binding fragment thereof to be employed, the subject of treatment, the mode of administration and the nature and severity of the condition being treated, and on the nature of prior treatments that the patient has undergone. Ultimately, the attending health care provider will decide the amount of the CD40 pathway antagonist with which to treat each individual patient. In some embodiments, the attending health care provider may administer low doses of the CD40 pathway antagonist and observe the patient's response. In other embodiments, the initial dose(s) of CD40 pathway antagonist administered to a patient are high, and then are titrated downward until signs of relapse occur. Larger doses of the CD40 pathway antagonist may be administered until the optimal therapeutic effect is obtained for the patient, and the dosage is not generally increased further.

In practicing some of the methods of treatment or uses of the present disclosure, a therapeutically effective amount of an CD40 pathway antagonist, e.g. an anti-CD40 antibody or antigen binding fragment thereof (e.g., mAb1, also called CFZ533 herein, mAb2, ASKP1240) or anti-CD40L antibody or antigen-binding fragment thereof is administered to a patient, e.g., a mammal (e.g., a human). While it is understood that the disclosed methods provide for prevention of graft loss in solid organ transplantation patients using a CD40 pathway antagonist (e.g., mAb1/CFZ533, mAb2, ASKP1240), this does not preclude that, if the patient is to be ultimately treated with a CD40 pathway antagonist, such CD40 pathway antagonist therapy is necessarily a monotherapy. Indeed, if a patient is selected for treatment with a CD40 pathway antagonist, then the CD40 pathway antagonist (e.g., mAb1/CFZ533, mAb2, ASKP1240) may be administered in accordance with the methods of the disclosure either alone or in combination with other agents and therapies.

In one embodiment the disclosure provides a method for prevention of graft loss in solid organ transplantation patients using mAb1/CFZ533, mAb2 or ASKP1240 in combination with two or more of the following agents: a calcineurin inhibitor (CNI) such as cyclosporine (CsA, Neoral®, Novartis) or tacrolimus (Tac, FK506, Prograf®, Astellas), a lymphocyte proliferation inhibitor such as mycophenolic acid (MPA; Myfortic®, Novartis) or mycophenolate mofetil (MMF; CellCept®, Roche) or proliferation signal inhibitor such as everolimus (Zortress®, Certican®, Novartis) or sirolimus (Rapamune®, Pfizer) or a T cell co-stimulation blocker such as belatacept (Nulojix®, BMS).

In another embodiment, the disclosure provides a method for prevention of graft loss in solid organ transplantation patients using mAb1/CFZ533, mAb2 or ASKP1240 in combination with a T cell co-stimulation blocker such as belatacept (Nulojix®, BMS) in a calcineurin-free treatment regimen.

In an additional embodiment the disclosure provides a method for prevention of graft loss in solid organ transplantation patients using mAb1/CFZ533, mAb2 or ASKP1240 in combination with CsA, (Neoral®, Novartis), tacrolimus (Tac, FK506, Prograf®, Astellas) and/or a mTor inhibitor such as everolimus (Zortress®, Certican®, Novartis.

In one embodiment the disclosure provides a method for a mono-therapeutic prevention of graft loss in solid organ transplantation patients using mAb1/CFZ533, mAb2 or ASKP1240, wherein mAb1/CFZ533, mAb2 or ASKP1240 are administered as the sole active pharmaceutical ingredient. It will be understood that regimen changes may be appropriate for certain solid organ transplantation patients, e.g., patients that display inadequate response to treatment with the CD40 pathway antagonists, e.g. an anti-CD40 antibody or antigen binding fragment thereof (e.g., mAb1, also called CFZ533 herein, mAb2, ASKP1240) or anti-CD40L antibody or antigen-binding fragment thereof to be employed. Thus, administration (e.g. mAb1/CFZ533 or mAb2) may be more frequent than monthly dosing, e.g., bimonthly dosing (every two weeks) or weekly dosing.

Patients are likely to benefit from a loading regimen intravenously or subcutaneously (e.g., weekly for several weeks [e.g., 1 to 5 weeks, e.g., dosing at weeks 0, 1, 2, 3 and/or 4] or biweekly for several weeks (e.g., 2 to 8 weeks, e.g., dosing at weeks 0, 2, 4, and/or 6) followed by maintenance regimen, e.g. a weekly, bi-weekly or monthly maintenance regimen.

For example, an appropriate regimen for mAb1/CFZ533 or mAb2 can be daily, once every second day, once every third day, once every fourth day, once every fifth day, once every sixth day, or weekly for several weeks [e.g., 1 to 5 weeks, e.g., dosing at weeks 0, 1, 2, 3 and/or 4] followed by a monthly maintenance regimen.

In another example, an appropriate regimen for mAb1/CFZ533 or mAb2 is weekly or biweekly for several weeks (e.g., 2 to 8 weeks, e.g., dosing at weeks 0, 2, 4, and/or 6) followed by a weekly, biweekly or monthly maintenance regimen.

It will also be understood that administration (e.g. for mAb1/CFZ533 or mAb2) may be less frequent than monthly dosing, e.g., dosing every 6 weeks, every 8 weeks (every two months), quarterly (every three months), etc.

It will be understood that dose escalation may be appropriate for certain solid organ transplantation patients based on severity of the disease, e.g., patients that display inadequate response to treatment with the CD40 pathway antagonists, e.g. an anti-CD40 antibody or antigen binding fragment thereof (e.g., mAb1, also called CFZ533 herein, mAb2, ASKP1240) or anti-CD40L antibody or antigen-binding fragment thereof to be employed. Thus, subcutaneous (SC) dosages may be greater than about 150 mg to about 900 mg SC, e.g., about 75 mg, about 100 mg, about 125 mg, about 175 mg, about 200 mg, about 250 mg, about 350 mg, about 400 mg, about 450 mg, about 500 mg, about 600 mg, etc.; similarly, intravenous (IV) dosages may be greater than about 10 mg/kg, e.g., about 11 mg/kg, 12 mg/kg, 15 mg/kg, 20 mg/kg, 25 mg/kg, 30 mg/kg, 35 mg/kg, etc. It will also be understood that dose reduction may also be appropriate for certain solid organ transplantation patients, e.g., patients that display adverse events or an adverse response to treatment with the CD40 pathway antagonist (e.g. an anti-CD40 antibody or antigen binding fragment thereof (e.g., mAb1, also called CFZ533 herein, mAb2, ASKP1240) or anti-CD40L antibody or antigen-binding fragment thereof). Thus, dosages of the CD40 pathway antagonist (e.g. an anti-CD40 antibody or antigen binding fragment thereof (e.g., mAb1, also called CFZ533 herein, mAb2, ASKP1240) or anti-CD40L antibody or antigen-binding fragment thereof), may be less than about 150 mg to about 900 mg s.c., e.g., about 25 mg, about 50 mg, about 75 mg, about 100 mg, about 125 mg, about 175 mg, about 200 mg, about 250 mg, about 350 mg, about 400 mg, about 450 mg, about 500 mg, about 600 mg, etc.

In some embodiments, the CD40 antagonist, e.g. an anti-CD40 antibody or antigen binding fragment thereof (e.g., mAb1, also called CFZ533 herein, mAb2, ASKP1240) or anti-CD40L antibody or antigen-binding fragment thereof may be administered to the patient at an initial dose of up to 30 mg/kg IV or 600 mg SC on multiple occasions (weekly, bi/-weekly), and the dose may be then adjusted to 150 mg or 300 mg or 450 mg weekly or bi-weekly delivered SC if needed, as determined by a physician.

In some embodiments, the CD40 antagonist, e.g. an anti-CD40 antibody or antigen binding fragment thereof (e.g., mAb1, also called CFZ533 herein, mAb2, ASKP1240) or anti-CD40L antibody or antigen-binding fragment thereof may be administered to the patient at an initial dose of 10 mg/kg delivered i.v., and the dose may be then adjusted to 150 mg or 300 mg or 450 mg delivered s.c. if needed, as determined by a physician.

In a specific embodiment, 3 mg/kg CFZ533 is administered s.c. on day 1 (D1), day 15 (D15), day 29 (D29), day 57 (D57), day 85 (D85), day 99 (D99), day 113 (D113), and day 114 (D141).

In another specific embodiment, 10 mg/kg CFZ533 is administered i.v. on D1, D15, D29, D57, D85, D99, D113, and D141.

In yet another specific embodiment, a loading dose which comprises four unit doses of 600 mg CFZ533 administered s.c. once weekly (Q1W), i.e. 600 mg CFZ533 s.c. on D1, D8, D15 and D22, followed by a maintenance dose which comprises unit doses of 300 mg administered s.c. once weekly (Q1W), i.e. 300 mg CFZ533 s.c. once weekly from D29 to D85.

In a further specific embodiment, a loading dose which comprises one dose of at least 10 mg and up to 30 mg CFZ533 per kg of the subject, administered IV one time on day 1 and potentially again 1 week post transplantation, followed by a maintenance dose which comprises unit doses of at least 300 mg administered SC weekly (Q1W) or bi-weekly (Q2W), i.e. 300 mg CFZ533 s.c. once weekly from D8 to D85.

CFZ533 may be administered quarterly, monthly, weekly or biweekly e.g. subcutaneously at a dosing of about 75 mg to about 600 mg or about 150 mg to about 300 mg being administered, by subcutaneous injection, at an unit dose of about 75 mg, about 150 mg, about 300 mg, about 450 mg or about 600 mg.

CFZ533 may be administered by subcutaneous injection, weekly, at a loading dose of about 300 mg to about 600 mg, preferably about 600 mg wherein the loading dose is administered during 1 to 4 weeks, preferably during 4 weeks.

The loading dose may also be an i.v. administration of about 10 mg/kg to about 30 mg/kg.

The loading dose of CFZ533 is preferably followed by a maintenance dose, administered weekly, biweekly or monthly. The maintenance dose is preferably 300 mg s.c. once weekly.

The anti-CD40 antibody or antigen-binding fragment thereof may be CFZ533, a functional derivative thereof or a biosimilar thereof.

As herein defined, "unit dose" refers to a s.c. dose that can be comprised between about 75 mg to 900 mg, e.g. about 150 mg to about 600 mg, e.g. about 150 mg to about 600 mg, e.g. about 300 mg to about 600 mg, or a e.g. about 150 mg to about 300 mg. For example an unit s.c. dose is about 75 mg, about 150 mg, about 300 mg, about 350 mg, about 400 mg, about 450 mg, about 500 mg, about 550 mg, about 600 mg.

Definitions

As used herein, CD40 refers to cluster of differentiation 40, also called tumor necrosis factor receptor superfamily member 5. The term CD40 refers to human CD40, for example as defined in SEQ ID NO: 19, unless otherwise described.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The word "substantially" does not exclude "completely," e.g., a composition which is "substantially free" from Y may be completely free from Y. Where necessary, the word "substantially" may be omitted from the definition of the disclosure.

The term "comprising" encompasses "including" as well as "consisting," e.g., a composition "comprising" X may consist exclusively of X or may include something additional, e.g., X+Y.

AUC0-t designates the area under the plasma concentration-time curve from time zero to time 't' where t is a defined time point after administration [mass x time/volume].

AUCtx-ty represents the area under the plasma concentration-time curve from time 'x' to time 'y' where 'time x' and 'time y' are defined time points after administration.

$C_{max}$ is the observed maximum plasma concentration following drug administration [mass/volume].

$C_{min}$ is the observed minimum plasma concentration following drug administration $C_{trough}$ is the observed plasma concentration that is just prior to the beginning of, or at the end of a dosing interval.

$T_{max}$ is the time to reach the maximum concentration after drug administration [time]. ss (subscript) indicate that the parameter is defined at steady state.

"Plasma concentration" is the blood plasma concentration of a patient.

The term "antibody" or "anti-CD40 antibody" and the like as used herein refers to whole antibodies that interact with (e.g., by binding, steric hindrance, stabilizing/destabilizing, spatial distribution) a CD40. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FRs). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelid antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass, preferably IgG and most preferably IgG1. Exemplary antibodies include CFZ533 (herein also designated mAb1) and mAb2, as set forth in Table 1.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv format.

The term "antigen binding portion" of an antibody (or simply "antigen portion"), as used herein, refers to full length or one or more fragments of an antibody, such as a protein, that retain the ability to specifically bind to an antigen or epitope (e.g., a portion of CD40).

The "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). Under IMGT, the CDR regions of an antibody can be determined using the program IMGT/DomainGap Align.

The term "epitope" as used herein refers to any determinant capable of binding with high affinity to an immunoglobulin. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883).

The phrase "isolated antibody", as used herein, refers to antibody that is substantially free of other antibodies having different antigenic specificities (e.g., an isolated antibody that specifically binds CD40 is substantially free of antibodies that specifically bind antigens other than CD40). An isolated antibody that specifically binds CD40 may, however, have cross-reactivity to other antigens, such as CD40 molecules from other species. Moreover, an isolated antibody may be substantially free of other cellular material and/or chemicals. The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo).

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of an antibody according to the present disclosure, e.g., of a specified sequence, still have the ability to bind the human CD40. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a $C_{kappa/lambda}$ region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a $K_D$ of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can 10 vary for other antibody isotypes. For example, high affinity binding for an IgM isotype refers to an antibody having a $K_D$ of $10^{-7}$ M or less, or $10^{-8}$ M or less.

As used herein, an antibody or a protein that "specifically binds to CD40 polypeptide" is intended to refer to an antibody or protein that binds to human CD40 polypeptide with a $K_D$ of 100 nM or less, 10 nM or less, 1 nM or less.

An antibody that "cross-reacts with an antigen other than CD40" is intended to refer to an antibody that binds that antigen with a $K_D$ of 1 µM or less, 100 nM or less, 10 nM or less, 1 nM or less. An antibody that "does not cross-react with a particular antigen" is intended to refer to an antibody that binds to that antigen, with a $K_D$ of 100 nM or greater, or a $K_D$ of 1 µM or greater, or a $K_D$ of 10 µM or greater. In certain embodiments, such antibodies that do not cross-react with the antigen exhibit essentially undetectable binding against these proteins in standard binding assays.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "ADCC" or "antibody-dependent cellular cytotoxicity" activity refers to cell depleting activity. ADCC activity can be measured by the ADCC assay as well known to a person skilled in the art.

As used herein, the term "silent" antibody refers to an antibody that exhibits no or low ADCC activity as measured in an ADCC assay.

In one embodiment, the term "no or low ADCC activity" means that the silent antibody exhibits an ADCC activity that is below 50% specific cell lysis, for example below 10% specific cell lysis as measured in a standard ADCC assay. No ADCC activity means that the silent antibody exhibits an ADCC activity (specific cell lysis) that is below 1%.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181:6664-69; Strohl, W., supra). Examples of silent Fc IgG1 antibodies comprise the so-called LALA mutant comprising L234A and L235A mutation in the IgG1 Fc amino acid sequence. Another example of a silent IgG1 antibody comprises the D265A mutation. Another silent IgG1 antibody comprises the N297A mutation, which results in aglycosylated/non-glycosylated antibodies.

The term "treatment" or "treat" is herein defined as the application or administration of an anti-CD40 antibody or protein according to the invention, for example, mAb1 or mAb2 antibody, to a subject, or application or administration a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to alleviate, ameliorate, or improve the autoimmune disease and/or inflammatory disease, any associated symptoms of the autoimmune disease and/or inflammatory disease, or the predisposition toward the development of the autoimmune disease and/or inflammatory disease.

By "treatment" is also intended the application or administration of a pharmaceutical composition comprising an anti-CD40 antibodies or protein of the invention, for example, mAb1 or mAb2 antibody, to a subject, or application or administration of a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to alleviate, ameliorate, or improve the autoimmune disease and/or inflammatory disease, any associated symptoms of the autoimmune disease and/or inflammatory disease, or the predisposition toward the development of the autoimmune disease and/or inflammatory disease.

The term "prevent" or "preventing" refer to prophylactic or preventative treatment; it is concerned about delaying the onset of, or preventing the onset of the disease, disorders and/or symptoms associated thereto.

As used herein, a subject is "in need of" a treatment if such subject would benefit biologically, medically or in quality of life from such treatment.

The term "pharmaceutically acceptable" means a non-toxic material that does not interfere with the effectiveness of the biological activity of the active ingredient(s).

As used herein, the term "administration" or "administering" of the subject compound means providing a compound of the invention and prodrugs thereof to a subject in need of treatment. Administration "in combination with" one or more further therapeutic agents includes simultaneous (concurrent) and consecutive administration in any order, and in any route of administration.

As used herein, a "therapeutically effective amount" refers to an amount of an anti-CD40 antibody or antigen binding fragment thereof, e.g., mAb1, that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., an anti-CD40 antibody, e.g., mAb1) administered alone, the term refers to that ingredient alone. When applied to a combination, the term refers to combined amounts of the active ingredients that result in the therapeutic effect, whether administered in combination, serially or simultaneously.

The phrase "therapeutic regimen" means the regimen used to treat an illness, e.g., the dosing protocol used during the prevention of graft loss in solid organ transplantation. A therapeutic regimen may include an induction regimen and a maintenance regimen.

The phrase "induction regimen" or "induction period" refers to a treatment regimen (or the portion of a treatment regimen) that is used for the initial treatment of a disease. In some embodiments, the disclosed methods, uses, kits, processes and regimens (e.g., methods of preventing graft loss in solid organ transplantation) employ an induction regimen. In some cases, the induction period is the period until maximum efficacy is reached. The general goal of an induction regimen is to provide a high level of drug to a patient during the initial period of a treatment regimen. An induction regimen may employ (in part or in whole) a "loading regimen" or "loading dosing", which may include administering a greater dose of the drug than a physician would employ during maintenance regimen, administering a drug more frequently than a physician would administer the drug during a maintenance regimen, or both. Dose escalation may occur during or after an induction regimen.

The phrase "maintenance regimen" or "maintenance period" refers to a treatment regimen (or the portion of a treatment regimen) that is used for the maintenance of a patient during treatment of an illness, e.g., to keep the patient in remission for long periods of time (months or years) following the induction period. In some embodiments, the disclosed methods, uses and regimens employ a maintenance regimen. A maintenance regimen may employ continuous therapy (e.g., administering a drug at a regular intervals, e.g., weekly, monthly [every 4 weeks], yearly, etc.) or intermittent therapy (e.g., interrupted treatment, intermittent treatment, treatment at relapse, or treatment upon achievement of a particular predetermined criteria [e.g., pain, disease manifestation, etc.]). Dose escalation may occur during a maintenance regimen.

The phrase "means for administering" is used to indicate any available implement for systemically administering a drug to a patient, including, but not limited to, a pre-filled syringe, a vial and syringe, an injection pen, an autoinjector, an i.v. drip and bag, a pump, a patch pump, etc. With such items, a patient may self-administer the drug (i.e., administer the drug on their own behalf) or a physician may administer the drug.

The terms "long-term prevention of graft rejection", "long-term prevention of graft loss", "long term graft survival" in transplant patients, in particular in solid organ transplant patients refers to a situation in which the transplanted tissue or organ or graft survives and functions for a period of at least 3 years, or at least 4 years, or at least 5 years post transplantation. The terms "long-term prevention of graft rejection", "long-term prevention of graft loss", "long term graft survival" in transplant patients, in particular in solid organ transplant patients can also refer to a situation in which the transplantation of the tissue or organ or graft is only needed once in the life of a patient.

Example 1. Anti-CD40 Antibodies

CD40 is a transmembrane glycoprotein constitutively expressed on B cells and antigenpresenting cells (APCs) such as monocytes, macrophages, and dendritic cells (DC). CD40 is also expressed on platelets, and under specific conditions can be expressed on eosinophils and activated parenchymal cells. Ligation of CD40 on B cells results in downstream signaling leading to enhanced B cell survival and important effector functions, including clonal expansion, cytokine secretion, differentiation, germinal center formation, development of memory B cells, affinity maturation, immunoglobulin (Ig) isotype switching, antibody production and prolongation of antigen presentation. CD154-mediated activation of the antigen-presenting cell (APC) also leads to induction of cytokine secretion and expression of surface activation molecules including CD69, CD54, CD80, and CD86 that are involved in the regulation of CD4+ T helper cell and CD8+ T cell cross-priming and activation.

CD154 exists in two forms; membrane-bound and soluble. Membrane-bound CD154 is a transmembrane glycoprotein expressed on activated CD4+, CD8+, and T-lymphocytes, mast cells, monocytes, basophils, eosinophils, natural killer (NK) cells, activated platelets and has been reported on B cells. It may also be expressed at low levels on vascular endothelial cells and up-regulated during local inflammation. Soluble CD154 (sCD154) is formed after proteolysis of membrane-bound CD154 and is shed from lymphocytes and platelets following cell activation. Once shed, sCD154 remains functional and retains its ability to bind to the CD40 receptor.

The critical role of CD40/CD154 interactions in vivo are best illustrated by patients suffering from Hyper-Immunoglobulin M (HIGM) as a result of loss of function mutations in CD40 or its ligand. Patients with HIGM present with a severe impairment of T cell dependent antibody responses, lack of B cell memory, and little to no circulating IgG, IgA or IgE. In patients with mutations in CD40 signaling, a similar phenotype and disease presentation has been described (van Kooten and Banchereau 2000).

Anti-CD40 mAbs with silenced ADCC activity have been disclosed in U.S. Pat. Nos. 8,828,396 and 9,221,913, incorporated by reference here in their entirety. Anti-CD40 mAbs with silenced ADCC activity are predicted to have an improved safety profile relative to other anti-CD40 antibodies, and in particular may be more suitable for non-oncologic indications, such as prevention of graft rejection in solid organ transplantation, and particularly prevention of graft rejection in kidney transplantation or liver transplantation. The anti-CD40 antibodies disclosed herein may be suitable for prevention of graft rejection in solid organ transplantation, and particularly prevention of graft rejection in kidney transplantation, liver transplantation, heart transplantation, lung transplantation, pancreas transplantation, intestine transplantation or composite tissue transplantation.

According to a non-binding hypothesis of the inventors, the two mAbs from patents U.S. Pat. Nos. 8,828,396 and 9,221,913, designated mAb1 and mAb2, are thought to be suitable compounds for treatment of transplant. The antibody mAb1, also called CFZ533, is particularly preferred.

mAb1 inhibits CD154-induced activation in vitro and T cell-dependent antibody formation and germinal center formation in vivo. In transplantation patients, CD40 blockade with mAb1 has been shown to offer a new treatment modality (Example 7).

To enable a person skilled in the art to practice the invention, the amino acid and nucleotide sequences of mAb1 and mAb2 are provided in Table 1 below.

Another anti-CD40 mAb known in the art is ASKP1240 from Astellas Pharma/Kyowa Hakko Kirin Co, as described e.g. in U.S. Pat. No. 8,568,725B2, incorporated by reference herein.

Yet another anti-CD40 mAb known in the art is BI655064 from Boehringer Ingelheim, as described e.g. in U.S. Pat. No. 8,591,900, incorporated by reference herein.

A further anti-CD40 mAb known in the art is FFP104 by Fast Forward Pharmaceuticals, as described e.g. in U.S. Pat. No. 8,669,352, incorporated by reference herein.

Another treatment modality might be MEDI4920 from AstraZeneca, which is a Anti-CD40L-Tn3 fusion protein, or the anti-CD40L antibody BIIB063 from Biogen.

Antibodies with the same mode of action as the above mentioned antibodies, so called biosimilars, are also covered by the disclosure, as will be appreciated by a person skilled in the art.

TABLE 1

Sequence table

| SEQ ID NO: | Description of sequence | Detailed amino acid or nucleotide sequences |
|---|---|---|
| 1 | HCDR1 of mAb 1 and mAb2 (Kabat) | SYGMH |
| 2 | HCDR2 of mAb 1 and mAb2 (Kabat) | VISYEESNRYHADSVKG |
| 3 | HCDR3 of mAb 1 and mAb2 (Kabat) | DGGIAAPGPDY |
| 4 | LCDR1 of mAb 1 and mAb2 (Kabat) | RSSQSLLYSNGYNYLD |

TABLE 1-continued

Sequence table

| SEQ ID NO: | Description of sequence | Detailed amino acid or nucleotide sequences |
|---|---|---|
| 5 | LCDR2 of mAb 1 and mAb2 (Kabat) | LGSNRAS |
| 6 | LCDR3 of mAb 1 and mAb2 (Kabat) | MQARQTPFT |
| 7 | Variable Heavy chain of mAb1 and mAb2 | QVQLVESGGGVVQPGRSLRLSCAASGFTFSSYGMHWVRQAPGKGLEWVAVISYEESNRYHADSVKGRFTISRDNSKITLYLQMNSLRTEDTAVYYCARDGGIAAPGPDYWGQGTLVTVSS |
| 8 | Variable light chain of mAb 1 and mAb2 | DIVMTQSPLSLTVTPGEPASISCRSSQSLLYSNGYNYLDWYLQKPGQSPQVLISLGSNRASGVPDRFSGSGSGTDFTLKISRVCAEDVGVYYCMQARQTPFTFGPGTKVDIR |
| 9 | Full length heavy chain of mAb 1 | QVQLVESGGGVVQPGRSLRLSCAASGFTFSSYGMHWVRQAPGKGLEWVAVISYEESNRYHADSVKGRFTISRDNSKITLYLQMNSLRTEDTAVYYCARDGGIAAPGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 10 | Full length light chain of mAb1 | DIVMTQSPLSLTVTPGEPASISCRSSQSLLYSNGYNYLDWYLQKPGQSPQVLISLGSNRASGVPDRFSGSGSGTDFTLKISRVEAEDVGVYYCMQARQTPFTFGPGTKVDIRRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 11 | Full length heavy chain of mAb2 | QVQLVESGGGVVQPGRSLRLSCAASGFTFSSYGMHWVRQAPGKGLEWVAVISYEESNRYHADSVKGRFTISRDNSKITLYLQMNSLRTEDTAVYYCARDGGIAAPGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 12 | Full length light chain of mAb2 | DIVMTQSPLSLTVTPGEPASISCRSSQSLLYSNGYNYLDWYLQKPGQSPQVLISLGSNRASGVPDRFSGSGSGTDFTLKISRVEAEDVGVYYCMQARQTPFTFGPGTKVDIRRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 13 | Fc region of mAb1 | APELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 14 | Fc region of mAb2 | APELLGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALP |

TABLE 1-continued

Sequence table

| SEQ ID NO: | Description of sequence | Detailed amino acid or nucleotide sequences |
|---|---|---|
| | | APIEKTISKAKGQPREPQVYTLPPSREEMTKNQ VSLTCLVKGFYPSDIAVEWESNGQPENNYKTTP PVLDSDGSFFLYSKLTVDKSRWQQGNVFSCSVM HEALHNHYTQKSLSLSPGK |
| 15 | DNA encoding Full length heavy chain of mAb1 | CAGGTGCAGCTGGTGGAATCTGGCGGCGGAGTG GTGCAGCCTGGCCGGTCCCTGAGACTGTCTTGC GCCGCCTCCGGCTTCACCTTCTCCAGCTACGGC ATGCACTGGGTGCGACAGGCCCCTGGCAAGGG ACTGGAATGGGTGGCCGTGATCTCCTACGAGGA ATCCAACAGATACCACGCTGACTCCGTGAAGGG CCGGTTCACAATCTCCCGGGACAACTCCAAGAT CACCCTGTACCTGCAGATGAACTCCCTGCGGAC CGAGGACACCGCCGTGTACTACTGCGCCAGGGA CGGAGGAATCGCCGCTCCTGGACCTGATTATTG GGGCCAGGGCACCCTGGTGACAGTGTCCTCCGC TAGCACCAAGGGCCCCTCCGTGTTCCCTCTGGC CCCCTCCAGCAAGTCCACCTCTGGCGGCACCGC CGCTCTGGGCTGCCTGGTGAAAGACTACTTCCC CGAGCCCGTGACCGTGTCCTGGAACTCTGGCGC CCTGACCTCCGGCGTGCACACCTTTCCAGCCGT GCTGCAGTCCTCCGGCCTGTACTCCCTGTCCTC CGTGGTGACCGTGCCCTCTAGCTCTCTGGGCAC CAGACCTACATCTGCAACGTGAACCACAAGCCC CTCCAACACCAAGGTGGACAAGCGGGTGGAACC CAAGTCCTGCGACAAGACCCACACCTGTCCCCC CTGCCCTGCCCCTGAACTGCTGGGCGGACCTTC CGTGTTCCTGTTCCCCCCAAAGCCCAAGGACAC CCTGATGATCTCCCGGACCCCCGAAGTGACCTG CGTGGTGGTGGACGTGTCCCACGAGGACCCTG AAGTGAAGTTCAATTGGTACGTGGACGGCGTG GAAGTGCACAACGCCAAGACCAAGCCCAGAGA GGAACAGTACGCCTCCACCTACCGGGTGGTGT CTGTGCTGACCGTGCTGCACCAGGACTGGCTG AACGGCAAAGAGTACAAGTGCAAGGTCTCCAA CAAGGCCCTGCCTGCCCCCATCGAAAAGACCA TCTCCAAGGCCAAGGGCCAGCCCCGCGAGCCA CAGGTGTACACACTGCCCCCCAGCCGGGAAGA GATGACCAAGAACCAGGTGTCCCTGACCTGTC TGGTCAAAGGCTTCTACCCCTCCGATATCGCC GTGGAGTGGGAGTCCAACGGACAGCCCGAGAA CAACTACAAGACCACCCCCCCTGTGCTGGACT CCGACGGCTCATTCTTCCTGTACTCCAAGCTG ACCGTGGACAAGTCCCGGTGGCAGCAGGGCAA CGTGTTCTCCTGCTCCGTGATGCACGAGGCCC TGCACAACCACTACACCCAGAAGTCCCTGTCC CTGAGCCCCGGCAAG |
| 16 | DNA encoding Full length light chain of mAb1 | GACATCGTGATGACCCAGTCCCCCCTGTCCCTG ACCGTGACACCTGGCGAGCCTGCCTCTATCTCC TGCAGATCCTCCCAGTCCCTGCTGTACTCCAAC GGCTACAACTACCTGGACTGGTATCTGCAGAAG CCCGGCCAGTCCCCACAGGTGCTGATCTCCCTG GGCTCCAACAGAGCCTCTGGCGTGCCCGACCGG TTCTCCGGCTCTGGCTCTGGCACCGACTTCACA CTGAAGATCTCACGGGTGGAAGCCGAGGACGTG GGCGTGTACTACTGCATGCAGGCCCGGCAGACC CCCTTCACCTTCGGCCCTGGCACCAAGGTGGAC ATCCGGCGTACGGTGGCCGCTCCAGCGTGTTC ATCTTCCCCCCAGCGACGAGCAGCTGAAGAGC GGCACCGCCAGCGTGGTGTGCCTGCTGAACAAC TTCTACCCCCGGGAGGCCAAGGTGCAGTGGAAG GTGGACAACGCCCTGCAGAGCGGCAACAGCCA GGAGAGCGTCACCGAGCAGGACAGCAAGGACT CCACCTACAGCCTGAGCAGCACCCTGACCCTG AGCAAGGCCGACTACGAGAAGCATAAGGTGTA CGCCTGCGAGGTGACCCACCAGGGCCTGTCCA GCCCCGTGACCAAGAGCTTCAACAGGGGCGAG TGC |
| 17 | DNA encoding Full length heavy chain of mAb2 | CAGGTGCAGCTGGTGGAATCTGGCGGCGGAGTG GTGCAGCCTGGCCGGTCCCTGAGACTGTCTTGC GCCGCCTCCGGCTTCACCTTCTCCAGCTACGGC ATGCACTGGGTGCGACAGGCCCCTGGCAAGGG |

TABLE 1-continued

Sequence table

| SEQ ID NO: | Description of sequence | Detailed amino acid or nucleotide sequences |
|---|---|---|
| | | ACTGGAATGGGTGGCCGTGATCTCCTACGAGGA<br>ATCCAACAGATACCACGCTGACTCCGTGAAGGG<br>CCGGTTCACAATCTCCCGGGACAACTCCAAGAT<br>CACCCTGTACCTGCAGATGAACTCCCTGCGGAC<br>CGAGGACACCGCCGTGTACTACTGCGCCAGGGA<br>CGGAGGAATCGCCGCTCCTGGACCTGATTATTG<br>GGGCCAGGGCACCCTGGTGACAGTGTCCTCCGC<br>TAGCACCAAGGGCCCCTCCGTGTTCCCTCTGGC<br>CCCCTCCAGCAAGTCCACCTCTGGCGGCACCGC<br>CGCTCTGGGCTGCCTGGTGAAAGACTACTTCCC<br>CGAGCCCGTGACCGTGTCCTGGAACTCTGGCGC<br>CCTGACCTCCGGCGTGCACACCTTTCCAGCCGT<br>GCTGCAGTCCTCCGGCCTGTACTCCCTGTCCTC<br>CGTGGTGACCGTGCCCTCTAGCTCTCTGGGCAC<br>CCAGACCTACATCTGCAACGTGAACCACAAGCC<br>CTCCAACACCAAGGTGGACAAGCGGGTGGAACC<br>CAAGTCCTGCGACAAGACCCACACCTGTCCCCC<br>CTGCCCTGCCCCTGAACTGCTGGGCGGACCTTC<br>CGTGTTCCTGTTCCCCCCAAAGCCCAAGGACAC<br>CCTGATGATCTCCCGGACCCCCGAAGTGACCTG<br>CGTGGTGGTGGCCGTGTCCCACGAGGACCCTGA<br>AGTGAAGTTCAATTGGTACGTGGACGGCGTGGA<br>AGTGCACAACGCCAAGACCAAGCCCAGAGAGGA<br>ACAGTACAACTCCACCTACCGGGTGGTGTCTG<br>TGCTGACCGTGCTGCACCAGGACTGGCTGAACG<br>GCAAAGAGTACAAGTGCAAGGTCTCCAACAAGG<br>CCCTGCCTGCCCCCATCGAAAAGACCATCTCCA<br>AGGCCAAGGGCCAGCCCCGCGAGCCACAGGTGT<br>ACACACTGCCCCCCAGCCGGGAAGAGATGACCA<br>AGAACCAGGTGTCCCTGACCTGTCTGGTCAAAG<br>GCTTCTACCCCTCCGATATCGCCGTGGAGTGGG<br>AGTCCAACGGACAGCCCGAGAACAACTACAAGA<br>CCACCCCCCCTGTGCTGGACTCCGACGGCTCAT<br>TCTTCCTGTACTCCAAGCTGACCGTGGACAAGT<br>CCCGGTGGCAGCAGGGCAACGTGTTCTCCTGCT<br>CCGTGATGCACGAGGCCCTGCACAACCACTACA<br>CCCAGAAGTCCCTGTCCCTGAGCCCCGGCA<br>AG |
| 18 | DNA encoding Full length light chain of mAb2 | GACATCGTGATGACCCAGTCCCCCCTGTCCCTG<br>ACCGTGACACCTGGCGAGCCTGCCTCTATCTCC<br>TGCAGATCCTCCCAGTCCCTGCTGTACTCCAAC<br>GGCTACAACTACCTGGACTGGTATCTGCAGAAG<br>CCCGGCCAGTCCCCACAGGTGCTGATCTCCCTG<br>GGCTCCAACAGAGCCTCTGGCGTGCCCGACCGG<br>TTCTCCGGCTCTGGCTCTGGCACCGACTTCACA<br>CTGAAGATCTCACGGGTGGAAGCCGAGGACGTG<br>GGCGTGTACTACTGCATGCAGGCCCGGCAGACC<br>CCCTTCACCTTCGGCCCTGGCACCAAGGTGGAC<br>ATCCGGCGTACGGTGGCCGCTCCCAGCGTGTTC<br>ATCTTCCCCCCCAGCGACGAGCAGCTGAAGAGC<br>GGCACCGCCAGCGTGGTGTGCCTGCTGAACAAC<br>TTCTACCCCGGGAGGCCAAGGTGCAGTGGAAG<br>GTGGACAACGCCCTGCAGAGCGGCAACAGCCAG<br>GAGAGCGTCACCGAGCAGGACAGCAAGGACTCC<br>ACCTACAGCCTGAGCAGCACCCTGACCCTGAGC<br>AAGGCCGACTACGAGAAGCATAAGGTGTAC<br>GCCTGCGAGGTGACCCACCAGGGCCTGTCCAGC<br>CCCGTGACCAAGAGCTTCAACAGGGGCGAGTGC |
| 19 | Amino acid sequence of human CD40 | MVRLPLQCVLWGCLLTAVHPEPPTACREKQYLIN<br>SQCCSLCQPGQKLVSDCTEFTETECLPCGESEFL<br>DTWNRETHCHQHKYCDPNLGLRVQQKGTSETDTI<br>CTCEEGWHCTSEACESCVLHRSCSPGFGVKQIAT<br>GVSDTICEPCPVGFFSNVSSAFEKCHPWTSCETK<br>DLVVQQAGTNKTDVVCGPQDRLRALVVIPIIFGI<br>LFAILLVLVFIKKVAKKPTNKAPHPKQEPQEINF<br>PDDLPGSNTAAPVQETLHGCQPVTQEDGKESRIS<br>VQERQ |

In one embodiment, an anti-CD40 antibody is provided, said antibody comprising an immunoglobulin VH domain comprising the amino acid sequence of SEQ ID NO: 7 and an immunoglobulin VL domain comprising the amino acid sequence of SEQ ID NO: 8.

In one embodiment, an anti-CD40 antibody is provided, said antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6.

In one embodiment, an anti-CD40 antibody is provided, said antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13.

In one embodiment, an anti-CD40 antibody is provided, said antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14.

In one embodiment, an anti-CD40 antibody is provided, said antibody comprising a silent Fc IgG1 region.

In a preferred embodiment, an anti-CD40 antibody designated mAb1 is provided. Specifically, mAb1 comprises the heavy chain amino acid sequence of SEQ ID NO: 9 and the light chain amino acid sequence of SEQ ID NO: 10; and mAb2 comprises the heavy chain amino acid sequence of SEQ ID NO: 11 and the light chain amino acid sequence of SEQ ID NO: 12.

1. Expression Systems

For expression of the light and heavy chains, the expression vector(s) encoding the heavy and light chains are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

Particularly a cloning or expression vector can comprise either at least one of the following coding sequences (a)-(b), operatively linked to suitable promoter sequences:

(a) SEQ ID NO: 15 and SEQ ID NO: 16 encoding respectively the full length heavy and light chains of mAb1; or (b) SEQ ID NO: 17 and SEQ ID NO: 18 encoding respectively the full length heavy and light chains of mAb2.

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621), CHOK1 dhfr+ cell lines, NSO myeloma cells, COS cells and SP2 cells. In particular, for use with NSO myeloma cells, another expression system is the GS gene expression system shown in PCT Publications WO 87/04462, WO 89/01036 and EP0338841.

When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods (See for example Abhinav et al. 2007, Journal of Chromatography 848: 28-37).

The host cells may be cultured under suitable conditions for the expression and production of mAb1 or mAb2.

2. Pharmaceutical Compositions

Therapeutic antibodies are typically formulated either in aqueous form ready for administration or as lyophilisate for reconstitution with a suitable diluent prior to administration. An anti-CD40 antibody may be formulated either as a lyophilisate, or as an aqueous composition, for example in pre-filled syringes.

Suitable formulation can provide an aqueous pharmaceutical composition or a lyophilisate that can be reconstituted to give a solution with a high concentration of the antibody active ingredient and a low level of antibody aggregation for delivery to a patient. High concentrations of antibody are useful as they reduce the amount of material that must be delivered to a patient. Reduced dosing volumes minimize the time taken to deliver a fixed dose to the patient. The aqueous compositions of the invention with high concentration of anti-CD40 antibodies are particularly suitable for subcutaneous administration.

Thus the invention provides an aqueous pharmaceutical composition, suitable for administration in a subject, e.g., for subcutaneous administration, comprising an anti-CD40 antibody such as mAb1 or mAb2.

The anti-CD40 antibody may be used as a pharmaceutical composition when combined with a pharmaceutically acceptable carrier. Such a composition may contain, in addition to an anti-CD40 antibody such as mAb1 or mAb2, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder.

In one specific embodiment the composition is a lyophilized formulation prepared from an aqueous formulation having a pH of 6.0 and comprising:

(i) 150 mg/mL mAb1 or mAb2
(ii) 270 mM sucrose as a stabilizer,
(iii) 30 mM L-histidine as a buffering agent, and
(iv) 0.06% Polysorbate 20 as a surfactant.

In another specific embodiment the pharmaceutical composition is an aqueous pharmaceutical composition has a pH of 6.0 and comprising:

(i) 150 mg/mL mAb1 or mAb2
(ii) 270 mM sucrose as a stabilizer,
(iii) 30 mM L-histidine as a buffering agent, and
(iv) 0.06% Polysorbate 20 as a surfactant.

In another specific embodiment the composition is a lyophilized or liquid formulation comprising:

(i) mAb1 or mAb2
(ii) sucrose as a stabilizer,
(iii) L-histidine as a buffering agent, and
(iv) Polysorbate 20 as a surfactant and at least one additional active pharmaceutical ingredient selected from the group consisting of a calcineurin inhibitor (CNI) such as cyclosporine (e.g. CsA, Neoral®, Novartis) or tacrolimus (e.g. Tac, FK506, Prograf®, Astellas), a lymphocyte proliferation inhibitor such as mycophenolic acid (e.g. MPA; Myfortic®, Novartis) or mycophenolate mofetil (e.g. MMF; CellCept®, Roche) or proliferation signal inhibitor such as everolimus (e.g. Zortress®, Certican®, Novartis) or sirolimus (e.g. Rapamune®, Pfizer) or a T cell co-stimulation blocker such as belatacept (e.g. Nulojix®, BMS).

3. Route of Administration

Typically, the antibodies or proteins are administered by injection, for example, either intravenously, intraperitoneally, or subcutaneously. Methods to accomplish this administration are known to those of ordinary skill in the art. It may also be possible to obtain compositions that may be topically or orally administered, or which may be capable of transmission across mucous membranes. As will be appreciated by a person skilled in the art, any suitable means for administering can be used, as appropriate for a particular selected route of administration.

Examples of possible routes of administration include parenteral, (e.g., intravenous (i.v. or I.V. or iv or IV), intramuscular (IM), intradermal, subcutaneous (s.c. or S.C. or sc or SC), or infusion), oral and pulmonary (e.g., inhalation), nasal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

An anti-CD40 therapy can optionally be initiated by administering a "loading dose/regimen" of the antibody or protein of the invention to the subject in need of anti-CD40 therapy. By "loading dose/regimen" is intended an initial dose/regimen of the anti-CD40 antibody or protein of the invention that is administered to the subject, where the dose of the antibody or protein of the invention administered falls within the higher dosing range (i.e., from about 10 mg/kg to about 50 mg/kg, such as about 30 mg/kg). The "loading dose/regimen" can be administered as a single administration, for example, a single infusion where the antibody or antigen-binding fragment thereof is administered IV, or as multiple administrations, for example, multiple infusions where the antibody or antigen-binding fragment thereof is administered IV, so long as the complete "loading dose/regimen" is administered within about a 24-hour period (or within the first month if multiple intravenous administration are needed, based on the severity of the disease). Following administration of the "loading dose/regimen", the subject is then administered one or more additional therapeutically effective doses of the anti-CD40 antibody or protein of the invention. Subsequent therapeutically effective doses can be administered, for example, according to a weekly dosing schedule, or once every two weeks (biweekly), once every three weeks, or once every four weeks. In such embodiments, the subsequent therapeutically effective doses generally fall within the lower dosing range (i.e. about 0.003 mg/kg to about 30 mg/kg, such as about 10 mg/kg, e.g. 10 mg/kg).

Alternatively, in some embodiments, following the "loading dose/regimen", the subsequent therapeutically effective doses of the anti-CD40 antibody or protein of the invention are administered according to a "maintenance schedule", wherein the therapeutically effective dose of the antibody or protein of the invention is administered weekly, bi-weekly, or once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the anti-CD40 antibody or protein of the invention fall within the lower dosing range (i.e. about 0.003 mg/kg to about 30 mg/kg, such as about 10 mg/kg, e.g. 10 mg/kg), particularly when the subsequent doses are administered at more frequent intervals, for example, once every two weeks to once every month, or within the higher dosing range (i.e., from 10 mg/kg to 50 mg/kg, such as 30 mg/kg), particularly when the subsequent doses are administered at less frequent intervals, for example, where subsequent doses are administered one month to 12 months apart.

The timing of dosing is generally measured from the day of the first dose of the active compound (e.g., mAb1), which is also known as "baseline". However, different health care providers use different naming conventions.

Notably, week zero may be referred to as week 1 by some health care providers, while day zero may be referred to as day one by some health care providers. Thus, it is possible that different physicians will designate, e.g., a dose as being given during week 3/on day 21, during week 3/on day 22, during week 4/on day 21, during week 4/on day 22, while referring to the same dosing schedule. For consistency, the first week of dosing will be referred to herein as week 0, while the first day of dosing will be referred to as day 1. However, it will be understood by a skilled artisan that this naming convention is simply used for consistency and should not be construed as limiting, i.e., weekly dosing is the provision of a weekly dose of the anti-CD40 antibody, e.g., mAb1, regardless of whether the physician refers to a particular week as "week 1" or "week 2". Example of dosage regimes as noted herein are found in FIGS. 1 and 2. It will be understood that a dose need not be provided at an exact time point, e.g., a dose due approximately on day 29 could be provided, e.g., on day 24 to day 34, e.g., day 30, as long as it is provided in the appropriate week.

As used herein, the phrase "container having a sufficient amount of the anti-CD40 antibody to allow delivery of [a designated dose]" is used to mean that a given container (e.g., vial, pen, syringe) has disposed therein a volume of an anti-CD40 antibody (e.g., as part of a pharmaceutical composition) that can be used to provide a desired dose. As an example, if a desired dose is 500 mg, then a clinician may use 2 ml from a container that contains an anti-CD40 antibody formulation with a concentration of 250 mg/ml, 1 ml from a container that contains an anti-CD40 antibody formulation with a concentration of 500 mg/ml, 0.5 ml from a container contains an anti-CD40 antibody formulation with a concentration of 1000 mg/ml, etc. In each such case, these containers have a sufficient amount of the anti-CD40 antibody to allow delivery of the desired 500 mg dose.

As used herein, the phrase "formulated at a dosage to allow [route of administration] delivery of [a designated dose]" is used to mean that a given pharmaceutical composition can be used to provide a desired dose of an anti-CD40 antibody, e.g., mAb1, via a designated route of administration (e.g., SC or IV). As an example, if a desired subcutaneous dose is 500 mg, then a clinician may use 2 ml of an anti-CD40 antibody formulation having a concentration of 250 mg/ml, 1 ml of an anti-CD40 antibody formulation having a concentration of 500 mg/ml, 0.5 ml of an anti-CD40 antibody formulation having a concentration of 1000 mg/ml, etc. In each such case, these anti-CD40 antibody formulations are at a concentration high enough to allow subcutaneous delivery of the anti-CD40 antibody. Subcutaneous delivery typically requires delivery of volumes of about 1 mL or more (e.g. 2 mL). However, higher volumes may be delivered over time using, e.g. a patch/pump mechanism.

Disclosed herein is the use of an anti-CD40 antibody (e.g., mAb1) for the manufacture of a medicament for the prevention of graft rejection in solid organ transplantation in a patient, wherein the medicament is formulated to comprise containers, each container having a sufficient amount of the anti-CD40 antibody to allow delivery of at least about 75 mg, 150 mg, 300 mg or 600 mg anti-CD40 antibody or antigen binding fragment thereof (e.g., mAb1) per unit dose.

Disclosed herein is the use of an anti-CD40 antibody (e.g., mAb1) for the manufacture of a medicament for the prevention of graft rejection in solid organ transplantation in a patient, wherein the medicament is formulated at a dosage to allow systemic delivery (e.g., IV or SC delivery) 75 mg, 150 mg, 300 mg of 600 mg anti-CD40 antibody or antigen binding fragment thereof (e.g., mAb1) per unit dose.

4. Kits

The disclosure also encompasses kits for treating a transplantation patient (as the case may be) with an anti-CD40 antibody or antigen binding fragment thereof, e.g., mAb1. Such kits comprise an anti-CD40 antibody or antigen binding fragment thereof, e.g., mAb1 (e.g., in liquid or lyophilized form) or a pharmaceutical composition comprising the anti-CD40 antibody (described supra). Additionally, such kits may comprise means for administering the anti-CD40 antibody (e.g., a syringe and vial, a prefilled syringe, a prefilled pen, a patch/pump) and instructions for use. The instructions may disclose providing the anti-CD40 antibody (e.g., mAb1) to the patient as part of a specific dosing regimen. These kits may also contain additional therapeutic agents (described supra) for treating psoriasis, e.g., for delivery in combination with the enclosed anti-CD40 antibody, e.g., mAb1.

The phrase "means for administering" is used to indicate any available implement for systemically administering a drug to a patient, including, but not limited to, a pre-filled syringe, a vial and syringe, an injection pen, an autoinjector, an i.v. drip and bag, a pump, patch/pump, etc. With such items, a patient may self-administer the drug (i.e., administer the drug on their own behalf) or a care-giver or a physician may administer the drug.

In one embodiment, the means for administering, such as an autoinjector, are part of a system comprising means for detecting and processing plasma concentration of drug in real-time. In a preferred embodiment, the system comprises means to compare the plasma concentration of drug with a threshold value, and adjust the dose accordingly.

Disclosed herein are kits for the treatment of a transplantation patient, comprising: a) a pharmaceutical composition comprising a therapeutically effective amount of an anti-CD40 antibody or antigen binding fragment thereof; b) means for administering the anti-CD40 antibody or antigen binding fragment thereof to the patient; and c) instructions providing administration of an anti-CD40 antibody or antigen binding fragment thereof to a patient in need thereof at a dose of about 3 to about 30 mg active ingredient per kilogram of a human subject (on multiple occasions).

In one specific embodiment, a use is provided, of a) a liquid pharmaceutical composition comprising an anti-CD40 antibody, a buffer, a stabilizer and a solubilizer, and b) means for subcutaneously administering the anti-CD40 antibody to a transplantation patient, for the manufacture of a medicament for the prevention of graft rejection in solid organ transplantation, wherein the anti-CD40 antibody:

i) is to be subcutaneously administered to the patient with a dose of about 3 to about 30 mg, such as 10 mg, active ingredient per kilogram of a human subject, three times, once every other week; and ii) thereafter, is to be subcutaneously administered to the patient as monthly doses of about 3 to about 30 mg, such as 10 mg, active ingredient per kilogram of a human subject, wherein said anti-CD40 antibody is selected from the group consisting of:

a) an anti-CD40 antibody comprising an immunoglobulin VH domain comprising the amino acid sequence of SEQ ID NO: 7 and an immunoglobulin VL domain comprising the amino acid sequence of SEQ ID NO: 8;

b) an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;

c) an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;

d) an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14;

e) an anti-CD40 antibody comprising a silent Fc IgG1 region: and f) an anti-CD40 antibody comprising the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

Example 2. Pharmacology

1. Primary Pharmacology mAb1 binds to human CD40 with high affinity ($K_d$ of 0.3 nM). However, it does not bind to Fcγ receptors (including CD16) or mediate antibody-dependent cellular cytotoxicity or complement-dependent cytotoxicity. mAb1 inhibits recombinant CD154 (rCD154)-induced activation of human leukocytes, but does not induce PBMC proliferation or cytokine production by monocyte-derived dendritic cells (DCs). mAb1 binds human and non-human primate CD40 with very similar affinities.

In vivo, mAb1 blocks primary and secondary T cell-dependent antibody responses (TDAR), and can prolong survival of kidney allografts in non-human primates (Cordoba et al 2015). In addition, mAb1 can disrupt established germinal centers (GCs) in vivo.

The CD40 receptor occupancy and functional activity were simultaneously assessed in vitro using human whole blood cultures. Functional activity was quantified via CD154-induced expression of CD69 (the activation marker) on CD20 positive cells (B cells) and CD40 occupancy was monitored using fluorescently labeled mAb1. Almost complete CD40 occupancy by mAb1 was required for full inhibition of rCD154-induced CD69 expression.

2. Secondary Pharmacology

The effects of mAb1 on platelet function and blood hemostasis were investigated, indicating that mAb1 does not induce platelet aggregation responses, rather displays certain mild inhibitory effects on platelet aggregation at high concentrations.

Example 3. Non-Clinical Toxicology and Safety Pharmacology

Toxicology studies with mAb1 did not reveal any significant organ toxicities, including no evidence of thromboembolic events as reported in clinical trials with anti-CD154 mAbs (Kawai et al 2000). In a 13-week GLP rhesus monkey study (weekly dosing at 10, 50 and 150 mg/kg), increased lymphoid cellularity was noted in 5/22 animals which was considered to be due to ongoing infection, an observation consistent with the pharmacology of mAb1. Inflammatory lesions in the kidneys and lungs of 2 animals at 50 mg/kg were noted, and in one of the two animals, lesions in the eyes and trachea were also noted. While a direct effect of mAb1 on the kidney and lung cannot be excluded, the weight of evidence including confirmation of opportunistic pathogens, suggests these findings are likely secondary to mAb1-mediated immunosuppression and of an infectious origin. In view of these inflammatory findings, the No Observed Adverse Effect Level (NOAEL) for the 13-week toxicity study was set at 10 mg/kg. In a 26-week chronic toxicity study in cynomolgus monkeys, no adverse, mAb1-related findings were discovered. Based on these data, the NOAEL was set at 150 mg/kg (26-week). The mean (all animals) $C_{max,ss}$ was 44, 3235, and 9690 µg/mL at 1, 50, and 150 (NOAEL) mg/kg S.C. weekly, respectively. The NOAEL derived from the 26-week cynomolgus monkey study is considered the most relevant for supporting the clinical dosing regimen.

Post-mortem histological and immuno-histological evaluation revealed a decrease in GCs in cortical B-cell areas of the spleen and lymphatic tissues. The recovery animals showed some cases of increased lymph node cellularity with normal T cell areas and increased B cell areas, which is consistent with reconstitution of GCs after drug withdrawal. Recovery animals were able to mount primary TDAR to keyhole limpet hemocyanin (KLH) immediately after blood levels of mAb1 dropped below the level necessary for full receptor occupancy.

Because of the complete inhibition of T cell-dependent antibody responses (TDAR), KLH, the formation of anti-drug antibodies (ADA) to mAb1 is not expected and therefore ADA-related side effects are considered unlikely when concentrations of mAb1 are maintained continuously at pharmacological levels.

Tissue cross-reactivity studies revealed that CD40 is not only present on immune cells, but also in various tissues. This is mainly due to its expression on endothelial and epithelial cells, where CD40 is involved in signaling such as responding to wound healing processes, upregulation of virus-defense, and inflammatory-related mediators. An antagonistic anti-CD40 monoclonal antibody like mAb1 is not expected to contribute to inflammatory processes, which was confirmed by in vitro studies using human umbilical vein endothelial cells (HUVEC).

Full guideline-conform reproductive toxicity studies have not been conducted thus far. However, a dose-range finding, embryo-fetal development (EFD) study in rabbits has been conducted in order to confirm the rabbit as relevant reproductive toxicology species. No effects on embryo-fetal development were seen and there was no treatment-related fetal external malformation in any group.

Example 4. Non-Clinical Pharmacokinetics and Pharmacodynamics

1. Pharmacokinetics (PK)

Typical for IgG immunoglobulins, the primary route of elimination of mAb1 is likely via proteolytic catabolism, occurring at sites that are in equilibrium with plasma. In addition, binding and internalization of mAb1-CD40 complexes resulted in rapid and saturable clearance routes. This was illustrated by non-linear mAb1 serum concentration-time profiles showing an inflection point at about 10-20 µg/mL. The contribution of the CD40-mediated clearance to the overall clearance depends on mAb1 concentration, together with levels of CD40 expression, internalization and receptor turnover rates. For serum concentrations of mAb1>10-20 µg/mL, linear kinetics are expected, while non-linear kinetics emerged at lower concentrations.

2. Pharmacodynamics (PD)

In a PK/PD study in cynomolgus monkeys, the inflection point (about 10 µg/mL) in the PK profiles was associated with a drop of CD40 saturation, as determined in an independent lymphocyte target saturation assay. As such this inflection point is viewed as a marker for the level of saturation of CD40, and an evidence for target engagement.

The link between CD40 occupancy and pharmacodynamic activity was further demonstrated in rhesus monkeys immunized with KLH. Monkeys were immunized with KLH three times (the first was about 3 weeks prior to dosing, the second was 2 weeks after mAb1 administration, and the third was after complete wash-out of mAb1). CD40 occupancy by mAb1 at plasma concentrations >40 µg/mL at the time of the second KLH vaccination completely prevented recall antibody responses. Once mAb1 was cleared, all animals mounted a full memory antibody response to the third KLH. These results suggest that the function of pre-existing memory B cells were not affected. After complete elimination of mAb1, immunization with tetanus toxoid (TTx) led to anti-TTx-IgG/IgM titers similar to non-treated animals and demonstrated that full TDAR was regained after mAb1 elimination.

3. Immunogenicity

As expected from an immunosuppressive drug, immunogenicity data in rhesus monkey (single dose) are in agreement with the results from the KLH-TDAR experience and confirmed that no immune response against mAb1 could be mounted under full CD40 occupancy by mAb1.

Example 5. Human Safety and Tolerability Data

The safety, tolerability, PK and PD activity of mAb1 are being assessed in an ongoing, randomized, double-blind, placebo-controlled, single-ascending dose study of mAb1 in healthy subjects and patients with rheumatoid arthritis (RA). A total of 48 subjects have been enrolled: 36 healthy subjects who received single doses of mAb1 up to 3 mg/kg IV or S.C., and 12 patients with RA, 6 of whom received single doses of mAb1 at 10 mg/kg IV. Overall, single doses up to 3 mg/kg mAb1 in healthy volunteers and a single of 10 mg/kg mAb1 in RA patients have been safe and well tolerated and no suspected serious adverse events (SAEs) have occurred. An investigation of the 30 mg/kg IV dose is ongoing in RA patients. As this study is still ongoing, all clinical data are preliminary in nature and based on interim analyses conducted up to a dose of 10 mg/kg in RA patients.

Example 6. Human Pharmacokinetics and Pharmacodynamics (Healthy Volunteers and Rheumatoid Arthritis Patients)

In healthy subjects as well as in patients with rheumatoid arthritis, after single IV or SC administration, CFZ533 PK profiles were consistent with target mediated disposition resulting in non-linear PK profiles and more rapid clearance when CD40 receptor occupancy dropped below approximately 90%.

Despite some inter-individual variability in the PK profiles from the Chinese subjects, the disposition of CFZ533 in Chinese subjects was generally similar as for non-Chinese subjects, and the target engagement was also similar (about 4 weeks) after 3 mg/kg IV CFZ533. At this dose level, similar PK/PD profiles were demonstrated through free CFZ533 profiles in plasma, CD40 occupancy on peripheral B cells measuring free CD40 and total CD40, and total sCD40 concentrations in plasma.

After SC administration in healthy subjects, CFZ533 was rapidly absorbed and distributed in line with what is expected for a typical IgG1 antibody in human. At 3 mg/kg SC, CFZ533 generally peaked at 3 days post-dose (7 days for 2 subjects), and 1 week after dosing plasma concentrations were in the same range as for after IV. At 3 mg/kg SC, duration of target engagement was also about 4 weeks.

In patients with rheumatoid arthritis at 10 mg/kg IV, as measured by free CD40 on whole blood B cells compared to mean pre-dose, and total sCD40 profiles in plasma, full CD40 occupancy was generally maintained for 8 weeks. At 30 mg/kg IV, PK and total sCD40 profiles in plasma are consistent with duration of target engagement of 16 weeks.

In healthy subjects CD40 engagement by CFZ533 generally led to a decrease in total CD40 on peripheral B cells by about 50%, tracking CD40 occupancy on B cells as measured by free CD40 on B cells. This is likely due to internalization and/or shedding of the membrane bound CD40 upon binding to CFZ533. In patients with rheumatoid arthritis the decrease in total CD40 on peripheral B cells was not confirmed.

The relationship between CFZ533 in plasma and CD40 occupancy on whole blood B cells (free CD40 on B cells) was defined, and CFZ533 concentrations of 0.3-0.4 µg/mL were associated with full (defined as ≥90%) CD40 occupancy on whole blood B cells.

More generally, non-specific and specific elimination pathways have been identified for CFZ533. The non-specific and high capacity pathway mediated by FcRn receptors is commonly shared by endogenous IgGs. The specific target mediated disposition of CFZ533 led to the formation of CFZ533-CD40 complexes that were partially internalized (with subsequent lysosomal degradation) and/or shed from the membrane. Target-mediated processes resulted in saturable and nonlinear disposition of CFZ533. The formation of CFZ533-CD40 complexes was dose/concentration-dependent, with saturation occurring at high concentrations of CFZ533.

Overall, the disposition of CFZ533 is dependent on the relative contribution of the specific (target mediated) and non-specific elimination pathways to the overall clearance of CFZ533. Nonlinear PK behavior was observed when CFZ533 concentrations were lower than that of the target, while at higher concentrations with CD40 receptors being saturated, the non-specific pathways predominate and the elimination of CFZ533 was linear.

As expected for a typical IgG1 antibody targeting a membrane bound receptor and demonstrating target mediated disposition, the extent of exposure of CFZ533 (AU-Clast) increased more than the increase in dose (hyperproportionality). Consequently, this is expected to be associated with a decrease in the volume of distribution and clearance of CFZ533 at higher doses.

One subject at 1 mg/kg IV CFZ533 (1 week full CD40 occupancy) developed specific antibodies to CFZ533 detected 6 weeks after CFZ533 plasma concentrations were below the limit of quantification, and definitively too low to block any CD40 pathway-relevant effects in tissue. The presence of anti-drug antibodies (ADAs) in this subject did not compromised exposure, and was not associated with an immune related safety signal. This corresponds to an ADA incidence of 2% in this study.

A single dose of 3 mg/kg (IV and SC) of CFZ533 transiently suppressed anti-KLH responses to the first KLH immunization, at CFZ533 concentrations corresponding to full (≥90%) receptor occupancy (for about 3-4 weeks). Anti-KLH primary responses were detected in all subjects as CFZ533 concentration, and accompanying receptor occupancy, declined. All subjects were able to mount recall responses to a second KLH immunization (administered after loss of receptor occupancy was anticipated).

Data suggest that CD40 engagement by CFZ533 prevented recombinant human CD154 (rCD154) mediated B cell activation in human whole blood. The rCD154-induced-CD69 expression on B cells was generally suppressed during a period corresponding to full CD40 occupancy on B cells. When CD40 occupancy was incomplete, the functional activity of rCD154 was restored.

There was no evidence of any effect of CFZ533 on immunophenotyping data.

Example 7. Clinical Trial

To assess the suitability of utilizing a human, anti-CD40 monoclonal antibodies with silenced ADCC activity in treatment or prevention of a disease related with CD40-CD154 pathway signaling, such as prevention of graft rejection in kidney transplantation, a clinical study was designed and conducted using the antibody CFZ533, herein also called mAb1.

1. Study Design

A 12-month randomized, multiple dose, open-label, study evaluating safety, tolerability, pharmacokinetics/pharmacodynamics (PK/PD) and efficacy of an anti-CD40 monoclonal antibody, CFZ533, in combination with mycophenolate mofetil (MMF) and corticosteroids (CS), with and without tacrolimus (Tac), in de novo renal transplant recipients.

The purpose of this adaptive, two-part study is to investigate the potential for CFZ533 to replace calcineurin inhibitors (CNI), while providing a similar rate of acute rejection prophylaxis and better renal function in a de novo renal transplant population receiving an allograft from standard criteria donors.

Figure 12:
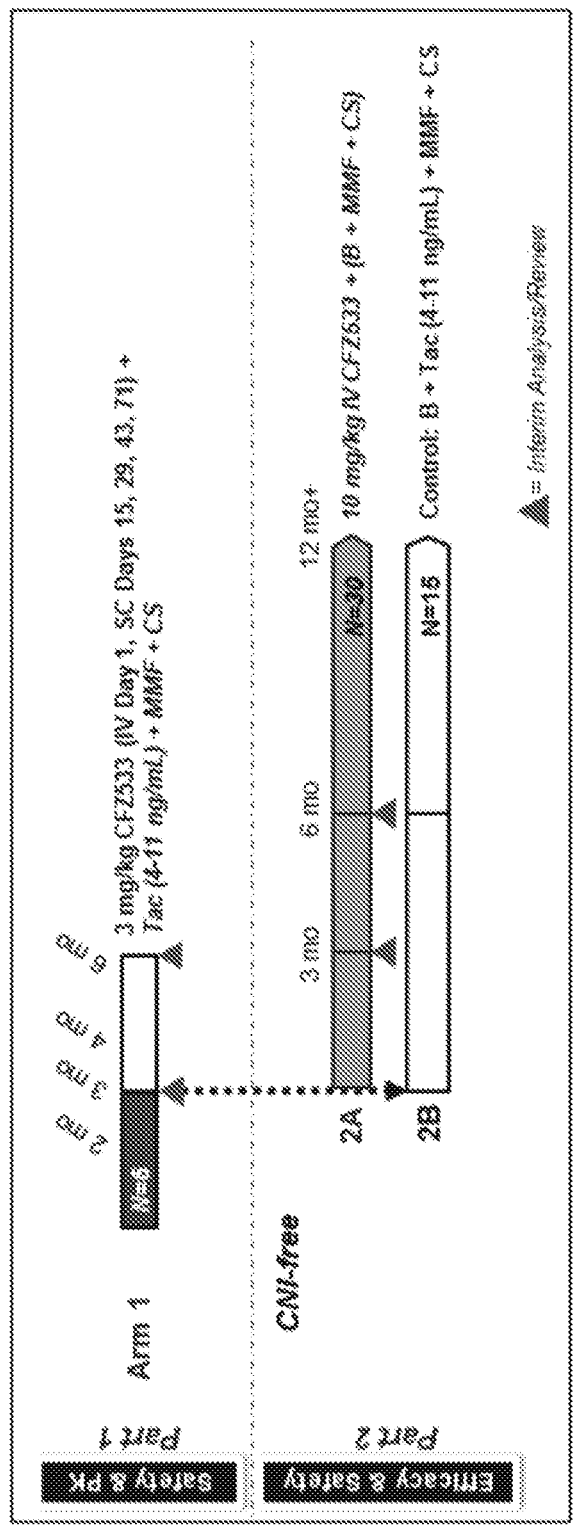
FIG. 12 is a schematic overview of the study design.

FIG. 12 is a schematic overview of the study design.

Part 1 of this trial will focus on profiling the multiple dose pharmacokinetics (PK), pharmacodynamics (PD) and tolerability for both IV and SC CFZ533 administration in the setting of standard-of-care, CNI-based immunosuppression.

For Arm 1, 6 patients total will be enrolled to receive IV induction (Day 1) and SC administration on Days 15, 29, 43 and 71 of 3 mg/kg CFZ533 with standard-exposure tacrolimus (whole blood trough concentration 4-11 ng/mL), MMF and CS.

Primary objective of Part 1 is to assess the safety, tolerability and pharmacokinetics of multiple IV and SC doses of CFZ533 in combination with MMF, CS, and Tac (standard exposure) in de novo renal transplant patients over the treatment and follow-up period. Secondary objectives of Part 1 are

- To quantify the magnitude and duration of peripheral blood CD40 occupancy (free CD40 and total CD40 on B cells);
- To quantify the change from baseline and recovery of peripheral blood total soluble CD40 and total soluble CD154; and
- To evaluate the immunogenicity of CFZ533 via the quantitative analysis of anti-CFZ533 antibodies.

Part 2 will evaluate the safety and efficacy of CFZ533 in the absence of a CNI in combination with adjunct MMF and basiliximab induction therapy for up to 12 months.

Following 2:1 randomization, 45 patients will be enrolled in Arms 2A and 2B in a parallel manner. Arm 2A will receive multiple intravenous CFZ533 10 mg/kg doses with basiliximab induction, MMF and CS; Arm 2B (control) will receive standard-exposure tacrolimus (whole blood trough concentration 4-11 ng/mL) with basiliximab induction, MMF and CS.

Primary objective of Part 2 is to assess the potential for CFZ533 to act as the primary immunosuppressant in a CNI-free regimen with MMF in de novo renal transplant patients as assessed by treated biopsy-proven acute rejections (tBPAR) at Month 3 post-transplantation.

Secondary objectives part 2 are

- To assess the safety and tolerability of CFZ533 administered chronically in combination with MMF and CS up to 3 months against a control;
- To assess the pharmacokinetics of multiple IV doses of CFZ533 during the 12-month treatment period;
- To quantify the magnitude and duration of peripheral blood CD40 occupancy (free CD40 and total CD40 on B cells) during the treatment period following multiple IV doses of CFZ533;
- To compare renal function in CFZ533 treatment arms to control at Month 3 post-transplantation as assessed by:
  Estimated glomerular filtration rate (GFR) using Modification of Diet in Renal Disease (MDRD);
  Proportion of patients with estimated GFR (eGFR)<60 mL/min/1.73 m$^2$;
  Proportion of patients with negative eGFR slope;
- To evaluate the immunogenicity of multiple IV doses of CFZ533 via the quantitative analysis of anti-CFZ533 antibodies; and
- To quantify the change from baseline and recovery of peripheral blood total soluble CD40 during the treatment period following multiple IV doses of CFZ533.

(1) Key Inclusion Criteria

Written informed consent;
Male or female patients ≥18 years old;
Recipients of a transplant from a heart-beating deceased, living unrelated or non-human leukocyte antigen (HLA) identical living related donor; and
Recipients of a kidney with a cold ischemia time (CIT) <30 hours;

(2) Key Exclusion Criteria

Multi-organ transplant recipients;
Recipient of an organ from a non-heart beating donor;
ABO incompatible allograft or complement-dependent lymphocytotoxic (CDC) cross-match positive transplant;
Receipt of a second kidney allograft, unless the first allograft was lost due to surgical complication;
High immunological risk for rejection as determined by local practice for assessment of anti-donor reactivity (e.g., high panel reactive antibodies (PRA)>20%, presence of pre-existing donor-specific antibodies (DSA));
At risk for tuberculosis (TB);
Anti-HIV positive, HBsAg-positive or anti-HCV positive;
Epstein-Barr virus (EBV) negative (in Part 1 only);
History of coagulopathy or medical condition requiring long-term anticoagulation, which would preclude renal biopsy after transplantation;
Active infection;
Pregnant or nursing (lactating) women; and
Women of child-bearing potential, defined as all women physiologically capable of becoming pregnant, unless they are using highly effective methods of contraception during dosing and for 12 weeks after the study medications have been stopped.

(3) Investigational and Reference Therapy

Figure 13A:
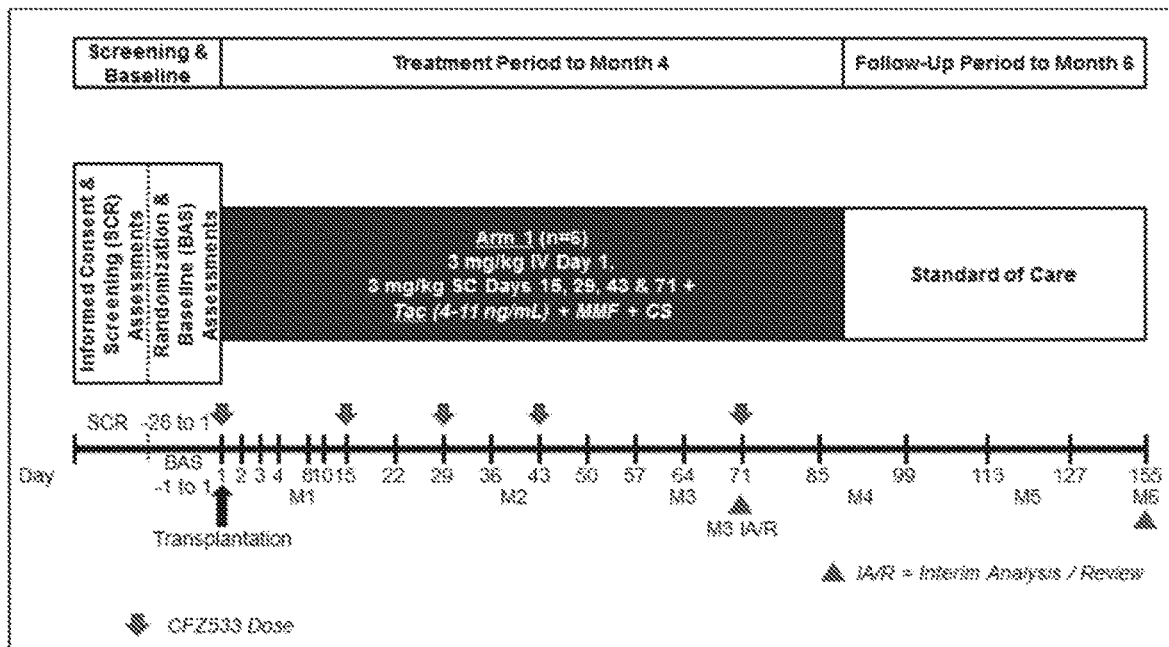
FIG. 13A shows the design of Part 1.

Part 1 (FIG. 13A); Arm 1, n=6: CFZ533 at 3.0 mg/kg SC (5 doses; first dose is IV, SC on Days 15, 29, 43 and 71)+tacrolimus (4-11 ng/mL)+MMF 1.0 g BID+CS.

Figure 13B:
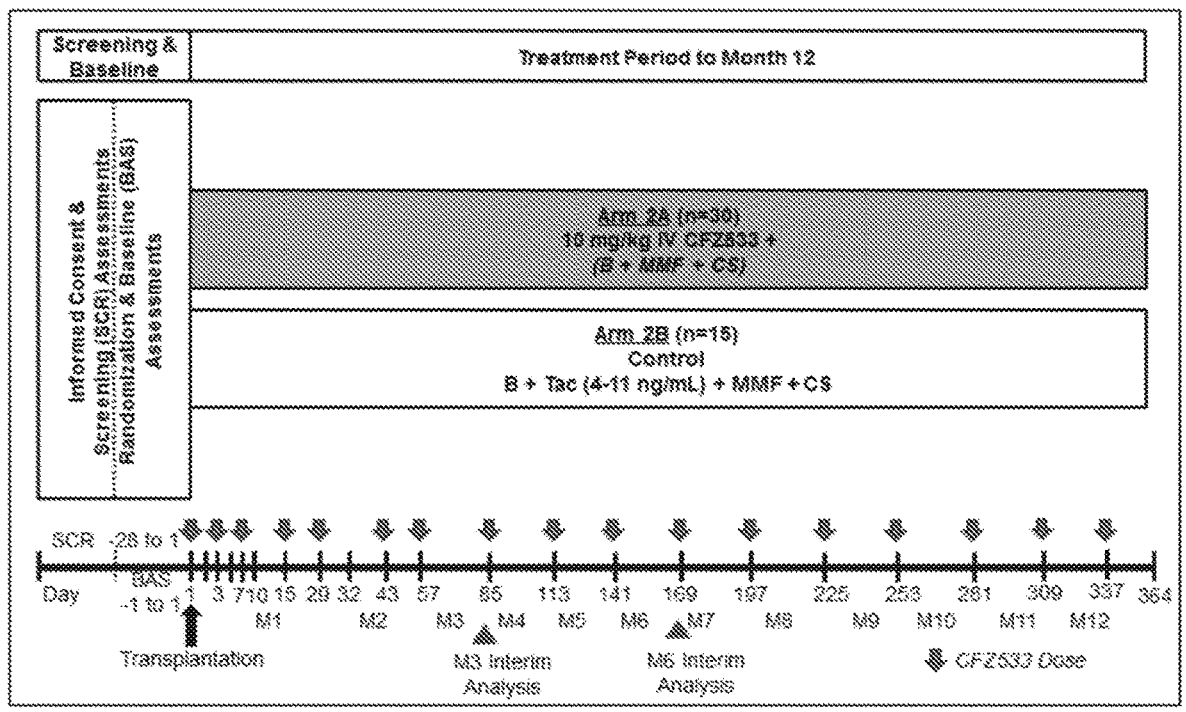
FIG. 13B shows the design of Part 2.

Part 2 (FIG. 13B); Arm 2A, n=30: Basiliximab 20 mg (Days 1, 4)+CFZ533 at 10 mg/kg IV (17 doses)+MMF 1.0 g BID+CS; and Arm 2B Control/Standard of Care, n=15: Basiliximab 20 mg (Days 1, 4)+tacrolimus (4-11 ng/mL)+MMF 1.0 g BID+CS.

(4) Concomitant Treatments

CMV, PCP, HBV & BK virus prophylaxis; and Oral *Candida* treatment.

(5) Efficacy Assessmen

Treated biopsy proven acute rejection (tBPAR), graft loss, death, estimated glomerular filtration rate (GFR).

Treated Biopsy Proven Acute Rejection (tBPAR)

A treated BPAR is any condition where the subject received anti-rejection treatment and was histologically diagnosed as acute rejection (according to the Banff 2009 criteria or the Banff 2013 criteria. Borderline histological findings are interpreted according to local medical practice and fulfill the criteria of tBPAR if anti-rejection treatment is given).

Renal biopsies will be collected for all cases of suspected acute rejection.

Kidney Allograft Biopsy

For all suspected rejection episodes, regardless of initiation of anti-rejection treatment, an allograft biopsy must be performed according to local practice preferably within 48 hrs. Biopsies will be read by the local pathologist according to the updated Banff 2009 criteria (or the Banff 2013 criteria depending on the local practice). The results of the biopsy read by the local pathologist will be listed on the Kidney Allograft Biopsy electronic case report/record form (eCRF). The results will be used for subject management for acute rejection. The local pathologist will remain blinded to treatment. Any biopsies performed according to local practice (e.g., not for cause) should also be recorded. In Part 2, biopsies performed for suspected rejection and other kidney disease related events will also be evaluated centrally by an independent Adjudication Committee.

Graft Loss

The allograft will be presumed to be lost on the day the subject starts daily sis and is not able to subsequently be removed from dialysis. If the subject undergoes allograft nephrectomy prior to starting permanent dialysis, then the day of nephrectomy is the day of graft loss. The reason for graft loss will be recorded on the Graft Loss eCRF. This will be reported on the Study Completion eCRF and Treatment Phase Disposition eCRF with Graft Loss as the reason for study discontinuation and on the appropriate Dosage Administration Record eCRF(s) if death occurs while on randomized treatment. Graft loss is considered a SAE and should be reported on the Adverse Event eCRF (as serious) and the SAE reported to the local Novartis Drug Safety and Epidemiology Department local Novartis Drug Safety and Epidemiology (DS&E) Department within 24 hrs.

Death

In the event of subject death, the SAE leading to death should be reported to Novartis DS&E within 24 hrs. The events leading to the death should be entered on the Adverse Event eCRF and the death should be indicated on the appropriate Dosage Administration Record eCRF(s) (if death occurs while on randomized treatment), on the Study Completion eCRF and on the Treatment Phase Disposition eCRF.

(6) Safety Assessments

Safety assessment are performed by measuring the following variables:

Renal function, Adverse and serious adverse events, Infections, Cytokines, Donor specific antibodies, new onset diabetes mellitus after transplantation (NODAT), EBV, CMV surveillance, Viral serology, Immunogenicity, Electrocardiogram (ECG), Vital and BK virus and tuberculosis signs, and Clinical labs.

An adverse event (AE) is any untoward medical occurrence (i.e., any unfavorable and unintended sign [including abnormal laboratory findings], symptom or disease) in a subject or clinical investigation subject. Therefore, an AE may or may not be temporally or causally associated with the use of a medicinal (investigational) product.

For all subjects who have signed informed consent and are entered into the study will have all adverse events occurring after informed consent is signed recorded on the Adverse Event eCRF. Pre-existing medical conditions/diseases (i.e., Medical History(ies)) are considered AEs if they worsen after providing written informed consent. Abnormal laboratory values or test results constitute AEs only if they induce clinical signs or symptoms, or are considered clinically significant, or they require therapy.

The occurrence of AEs should be sought by non-directive questioning of the subject at each visit during the study. AEs also may be detected when they are volunteered by the subject during or between visits or through physical examination, laboratory test, or other assessments. AEs must be recorded on the Adverse Event eCRF under the signs, symptoms or diagnosis associated with them.

An SAE is defined as any AE which meets any one of the following criteria:
is fatal or life-threatening
results in persistent or significant disability/incapacity
constitutes a congenital anomaly/birth defect
requires inpatient hospitalization or prolongation of existing hospitalization, unless hospitalization is for:
routine treatment or monitoring of the studied indication, not associated with any deterioration in condition
elective or pre-planned treatment for a pre-existing condition that is unrelated to the indication under study and has not worsened since signing the informed consent form
treatment on an emergency outpatient basis for an event not fulfilling any of the definitions of a SAE given above and not resulting in hospital admission
social reasons and respite care in the absence of any deterioration in the subject's general condition
is medically significant, i.e., defined as an event that jeopardizes the patient or may require medical or surgical intervention to prevent one of the outcomes listed above.

All malignant neoplasms will be assessed as serious under "medically significant" if other seriousness criteria are not met.

(7) Other Assessments

Other variables are also assessed, such as pharmacokinetics (Free CFZ533 in plasma; Tac trough levels; MPA trough levels; and Soluble CD40 and soluble CD154 in plasma), Graft survival, Patient survival, and Lymph node/tissue biopsy.

2. Dosing Regimen

Before any study-related evaluations are performed, the patient must give written informed consent. Once consent is obtained, pre-transplant screening and baseline assessments will occur to determine the patient's eligibility to participate in the study starting up to 28 days prior to transplantation. If the screening, baseline and study Day 1 visits occur in close proximity of each other (i.e., within a 12 hour timespan). Data collection from assessments performed at the clinical site as part of medical standard of care but prior ICF sign-off is acceptable in order to confirm patient eligibility for patients receiving an organ from a deceased donor, if assessed shortly before transplantation (i.e. within 24h—matching the baseline window of Day −1 to Day 1) and in-line with inclusion and exclusion criteria.

Day 1 is defined as the day of randomization/enrollment and transplantation. This protocol defines 7 days to a week and 4 weeks (or 28 days) to a Study Month. For example, Week 2 is considered to start on Day 8 and Study Month 2 is considered to start on Week 5/Day 29. Randomization/enrollment should occur within 24 hours pre-transplant and drug administration will begin after randomization/enrollment. If CFZ533 is to be administered, the first dose of CFZ533 will be administered IV pre-transplant or intraoperatively, and must be completed by the time of unclamping. Other study drugs must be started within 24 hours post transplant or according to local practice.

Patients who are randomized/enrolled but not transplanted will be replaced. All randomized/enrolled subjects are expected to continue in the study up to Month 6 (Part 1) or Month 12 (Part 2) regardless of being on or off randomized/assigned treatment. All subjects will be followed-up for safety (e.g., SAEs) for approximately three months after their last dose of CFZ533 or 2 months after the end of study (EoS) visit for patients on standard of care (SoC) treatment.

Any treatment arm in which the rejection rate fulfills the a priori defined stopping rules (not shown) will be immediately discontinued at any time during the study.

The transition from one arm to the next including Parts 1 to 2 will be based on a priori defined rules. Any changes in dosing or clinical conduct of the study will be implemented via an amendment, approved by the ethics committee responsible for approval of this study, and by the local heath authority when mandated by local regulations.

Safety assessments will include physical examinations, ECGs, vital signs, standard clinical laboratory evaluations (hematology, blood chemistry, urinalysis) AE and SAE monitoring as well as special assessments.

Approximately 6 patients who meet the inclusion criteria will be enrolled within approx. 12 hours pre-transplant to receive IV and SC CFZ533 at 3 mg/kg on Days 1 (IV), 15, 29, 43 and 71) with standard-exposure Tac (whole blood trough concentration 4-11 ng/mL), mycophenolate mofetil 1.0 g BID and CS (FIG. 13A).

The first dose of CFZ533 will be administered IV pre-transplant or intra-operatively. Drug administration will begin after enrollment and must be completed by the time of unclamping. Subsequent doses of CFZ533 will be administered SC for a period of approximately 3 months.

Other study drugs must be started within 24 hours post-transplant.

The day of enrollment and transplant will be considered to be study Day 1. Thereafter, post-transplant hospitalization will occur and then patients will make weekly study visits during Months 1-3 (up to approximately Day 71), then approximately every other week for Months 4-6 (up to approximately Day 155).

Cumulative efficacy and safety data will be collected on an ongoing basis during the conduct of the study.

PK, PD and tBPARs will be reviewed on an ongoing basis by the clinical trial team. If at any time the observed number of tBPARs exceeds the a priori-defined stopping criteria the study will be stopped.

Approximately 45 patients who meet the inclusion criteria will be randomized in a 2:1 fashion within 24 hours pre-transplant to receive one of the 2 treatment arms (FIG. 13B): 1. Arm 2A, n=30: Basiliximab 20 mg (Days 1, 4)+CFZ533 at 10 mg/kg IV (17 doses)+MMF 1.0 g BID+CS; 2. Arm 2B Control/SoC, n=15: Basiliximab 20 mg (Days 1, 4)+Tac (4-11 ng/mL)+MMF 1.0 g BID+CS.

Induction therapy must be started within 2 hours prior to transplantation, or according to local practice.

The first dose of CFZ533 will be administered IV pre-transplant or intra-operatively. Drug administration will begin after randomization and must be completed by the time of unclamping. Subsequent doses of CFZ533 will be administered IV (Arm 2A), over a period of 12 months.

Other study drugs (apart from Basiliximab) should be started within 24 hours post-transplant. The second dose of basiliximab will be administered on Day 4, or according to local practice.

The day of randomization and transplant will be considered to be study Day 1. Further treatment will be given on study Days 3, 7, 15, 29, 43, 57 and then monthly thereafter until Months 12 (up to approximately Day 337). Subjects will then undergo Study Completion evaluations.

The primary endpoint of Part 2 will be assessed to determine whether the success criteria (safety and tBPAR) have been met. If notable AEs or safety concerns meeting the a priori-defined stopping criteria one of the planned dose levels may be changed or discontinued via amendment.

Subjects will undergo Study Completion evaluations at the end of the trial.

3. Rationale of Dose/Regimen, Duration of Treatment

The open-label, adaptive design selected for Part 1 of this prospective, multicenter study will allow for a cautious comparison and evaluation of the multiple dose CFZ533 safety, tolerability, PK and PD as added to MMF+Tac and CS for 3 months. Part 2 expands upon the knowledge gained in Part 1 to assess the clinical activity and exposure-response of CFZ533 in a well powered CNI-free treatment regimen with basiliximab induction+MMF and CS for initial and maintenance prophylaxis of organ rejection in adult de novo renal transplant recipients.

Although the ideal study would employ a double-blind, double-dummy methodology to minimize bias, in consideration of the inherent complexity of this adaptive study (multiple arms, frequent visits, interim analysis and extensive investigations), it has been decided to utilize an open-label design. This open-label design will not only minimize the risks for patients during the initial investigation of CFZ533 should the need for rapid intervention arise, such as emergent SAEs, but it also avoids the additional difficulties and errors associated with sham-dose adjustments for a Tac placebo in CFZ533 arms and placebo injections/infusions in the control group. It is recognized that Investigator bias can affect the management of patients receiving investigational treatment; especially in an open-label study setting. In general, such scrutiny biases the study in favor of the control arm. As such, efforts to minimize bias for or against the CFZ533 treatment arms will be managed through the use of a limited number of high-quality transplant centers with a similar standard of care and patient management. In order to overcome any bias introduced by the open-label design, in Part 2, a blinded external independent adjudication committee (AC) has been formed to centrally evaluate all biopsies taken for suspected rejection reactions and other kidney disease related events in an unbiased, standardized and blinded manner. Adjudication outcome will be entered into the eCRF and additional outputs provided.

This first-in-transplant study will enroll a de novo patient population who receive a kidney from donors per the inclusion and exclusion criteria outlined in the clinical study protocol. This population was selected since they typically present the lowest risk of post-transplant complications, including delayed graft function and provide a fair assessment of clinical activity while not requiring the highest level of immunosuppression. Safety risks will be reviewed on a regular basis by an external DMC, with particular attention given to serious infections and malignancies associated to those (e.g., PTLD), as well as thromboembolic events.

The efficacy endpoints of treated BPAR and GFR are consistent with recent HA guidance (CHMP/EWP/263148/06 2009) and discussions (FDA Workshop 2012) on including an assessment of graft function as well as the traditional efficacy endpoints (e.g., tBPAR, BPAR) with or without clinical outcomes (i.e., Death and Graft loss).

The composite of tBPAR, graft loss or death has been used as an endpoint in many previous studies in the kidney transplantation indication and has been widely accepted by health authorities for registration purposes in this indication.

Overall, this design is consistent with well-established precedents by global health authorities for clinical development of immunosuppressive regimens in kidney transplantation.

The initial CFZ533 dose to be administered to de novo renal transplant patients via both IV and SC route is 3 mg/kg CFZ533 (Part 1). For all CFZ533 treatment regimens, the first dose of CFZ533 will be administered IV prior to or during transplant surgery to ensure full CD40 target occupancy on B cells in the periphery at the time of unclamping and revascularization of the transplanted organ; the timing avoids initiation of an immune reaction in the initial presence of the foreign antigens. The SC route is preferred for patient convenience and ease of administration while the IV route is reserved for high doses and administration of the initial dose during surgery.

Figure 14:
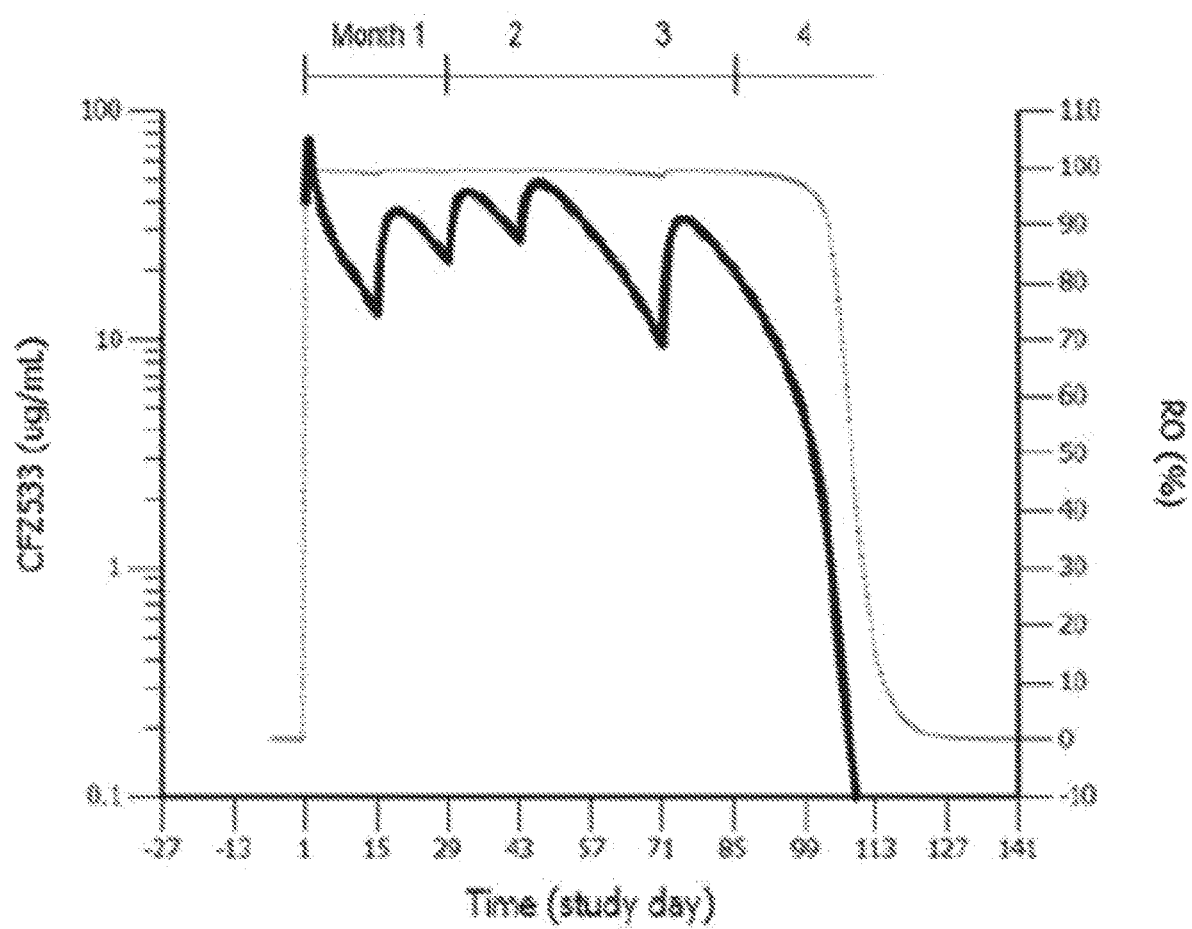
FIG. 14 is a graph showing simulated pharmacokinetics profile before study started.

The following section discusses the overall CFZ533 dose rationale and specifics for Parts 1 and 2 in turn: Dose selection for Part 1: In healthy volunteers, 3 mg/kg IV or SC led to full (>90%) CD40 saturation on B cells for about 4 weeks. Nevertheless, it is recognized that differences in expression level and/or turnover of membrane bound (Lowe et al 2010) and soluble targets (Schwabe et al 1999, Contin et al 2003, Komura et al 2007) may have an impact on the PK/PD profile of therapeutic antibodies. To profile the multiple-dose CFZ533 PK and PD in de novo renal transplant patients, both IV and SC doses of 3 mg/kg CFZ533 will be investigated over about 2½ months in Part 1 of this study. In addition, to better control for inter-patient variability and minimize the number of patients exposed to quadruple immunosuppression, it is planned to evaluate both IV and biweekly and monthly SC administration within the same 6 patients. A simulation of the expected CFZ533 PK and CD40 receptor occupancy planned for Part 1 is presented in FIG. 14. There is shown CFZ533 PK/PD simulation of SC administration with an IV loading dose at the time of transplant. SC administration on Days 15, 29 and 43 and 71. NOTE: the black and thick curve represents the CFZ533 concentration over time (days). The left y-axis represents the CFZ533 concentration in µg/mL. The dashed grey line represents the peripheral CD40 receptor occupancy on B cells over time and the right y-axis represents the CD40 receptor occupancy in percent (%).

If the disposition of CFZ533 between normal healthy subjects and renal transplant patients is conserved, the Cmax following the three planned q2wk SC doses will approach 50 µg/mL. In the event the CFZ533 clearance is decreased, it is possible that CFZ533 concentrations could approach or exceed those of an IV infusion (about 80 µg/mL).

This CFZ533 regimen is expected to result in complete CD40 suppression in peripheral whole blood over the treatment interval. Results from Part 1 will provide PK and PD data that will be used to better inform modeling and selection of IV and SC dosing regimens to be investigated in Part 2 of this trial. To further minimize the risk for over immunosuppression, no basiliximab induction therapy will be administered to patients participating in this part of the trial. Patients will also receive prophylaxis for CMV and PCP and recipients with negative EBV serology will be excluded.

Upon completion of the final CFZ533 dose administration, patients will remain on SoC to be managed based on defined local practices and will be monitored through Month 6 per the study protocol.

In Part 2 of this trial, CFZ533 will be investigated at 10 mg/kg IV (a loading regimen consisting of 7 doses is being used in the first 2 months, then monthly (q4w) dosing starting on study Day 57).

Safety and tolerability confirmed in humans: A Phase 1 study (CCFZ533X2101), testing Single ascending doses (0.03 to 30 mg/kg) of CFZ533 i.v. and 3 mg/kg s.c., was completed and did not reveal major safety concern up to the highest dose tested (10 mg/kg i.v.). Based on clinical experience so far, the 10 mg/kg i.v. dosing regimen is anticipated to be safe and tolerable in Tx patients.

Figure 3:
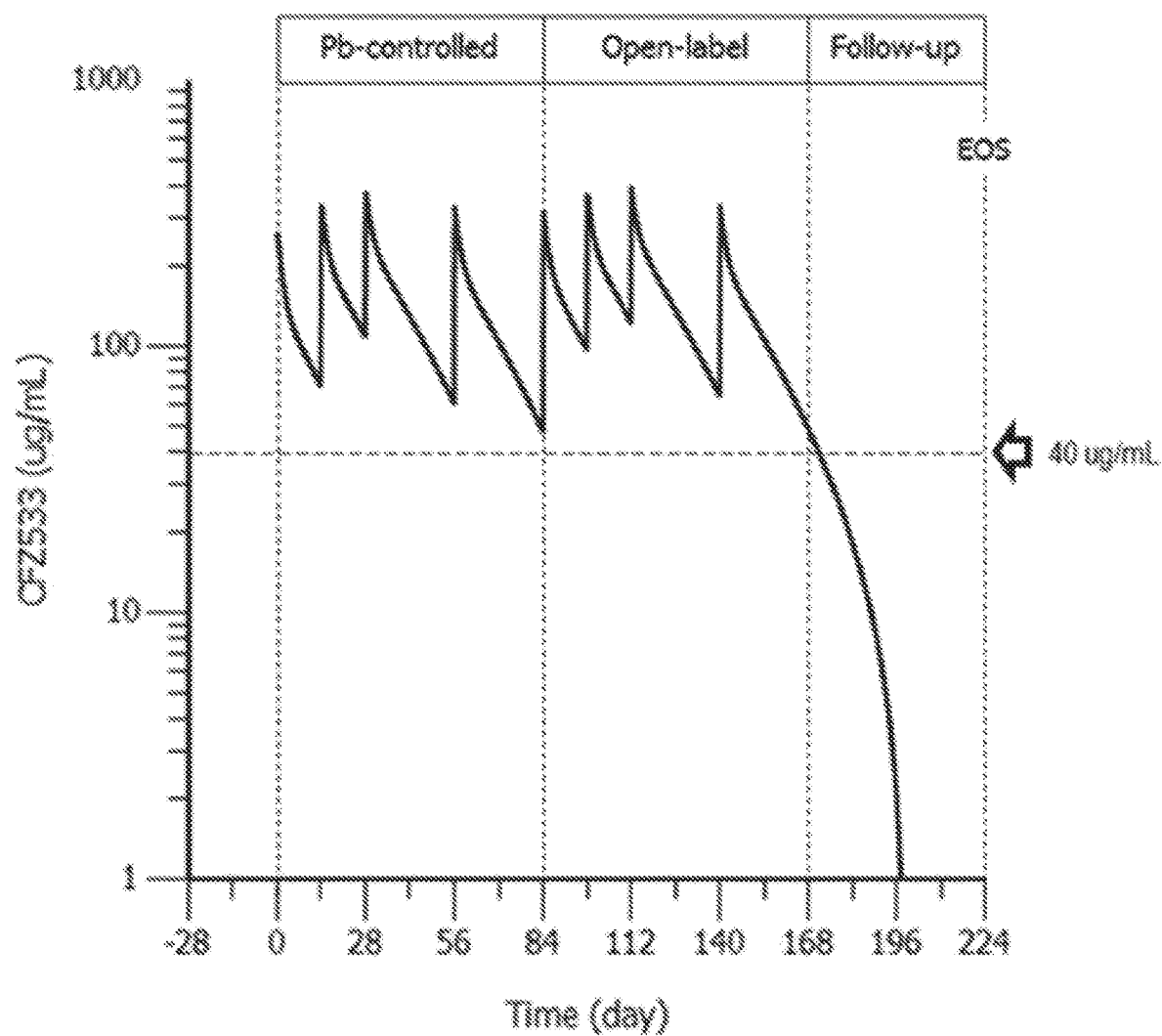
FIG. 3 is a graph showing preliminary simulated pharmacokinetics profiles before study started.

Adequate safety margin from preclinical toxicological studies: GLP toxicology studies to date have tested CFZ533 at (i) weekly s.c. dosing for 13 weeks at 10, 50, and 150 mg/kg (s.c. and i.v.) in rhesus monkeys, and (ii) weekly s.c. dosing for 26 weeks at 1, 50, and 150 mg/kg in cynomolgus monkeys. These studies did not reveal any major finding that would prevent the use of CFZ533 at the proposed intravenous regimen for 12 weeks or 24 weeks. In the 26-week toxicity study in cynomolgus monkey, at steady state, an average concentration of 8300 µg/mL (Cav,ss) was obtained after weekly dosing at 150 mg/kg (NOAEL). The corresponding systemic exposure (AUC, steady state conditions) over a 1-month period would be 232400 day*µg/mL, which is about 57-fold higher than the predicted systemic plasma exposure over the first month (AUC0-28 days; FIG. 3). In the 26-week toxicology study, at NOAEL, Cmax, ss was 9495 µg/mL, which is 24-fold higher than the expected Cmax (about 400 µg/mL) for the proposed intravenous regimen in tx patients (FIG. 3).

FIG. 3 shows predicted mean plasma concentration-time profile for CFZ533 given intravenously at 10 mg/kg (Cohort 2). Mean PK profiles were simulated for 10 mg/kg i.v. CFZ533 given at Study Day 1, 15, 29 and 57 (placebo controlled period), and Study Day 85, 99, 113 and 141 (open-label period). A Michaelis-Menten model was applied using parameters obtained from a preliminary model-based population analysis of Cohort 5 (3 mg/kg i.v.) PK data from FIH study CCFZ533X2101 in healthy subjects. No previous experience with an anti-CD40 blocking agent existed in human tx, and any potential differences in the biology of CD40 (expression, turnover) between healthy subjects and tx patients was no known. The proposed i.v. regimen was expected to provide, throughout the entire treatment period, sustained plasma concentrations above 40 µg/mL, to anticipate for an increased CD40 expression in target tissues in tx patients. The horizontal dotted line at 40 µg/mL is representing plasma concentration above which it is expected full CD40 occupancy and pathway blockade in target tissues (based on PD data from 26-week toxicology study in cynomolgus monkey—dose group 1 mg/kg). The expected systemic exposure for the first month (higher dosing frequency) is 4087 day*m/mL (57-fold lower than the observed systemic plasma exposure over one month at steady state in the 26-week toxicology study in cynomolgus—NOAEL at 150 mg/kg weekly), the expected Cmax is about 400 µg/mL.

Relevant PD effects in tissues in non-human primates: In the 26-week toxicological study (1 mg/kg dose group) animals with average steady state plasma concentrations ≥38 µg/mL had a complete suppression of germinal centers in cortical B cell areas of lymph nodes. The 10 mg/kg i.v. regimen was expected to provide, throughout the entire treatment period (placebo-controlled and open-label, see FIG. 3), sustained plasma concentrations above 40 µg/mL, to anticipate for higher CD40 expression in tx patients, and incomplete PD effects in target tissue due to loss of target saturation.

Data from ASKP1240, a monoclonal antibody blocking CD40: A recent analysis of disclosed PK/efficacy data from Astellas' anti-CD40 antibody ASKP1240 in solid organ transplantation (Harland et al 2015) demonstrated that efficient target mediated antibody clearance in tissue, could result in loss of CD40 blockade and likely loss of efficacy, as a consequence of a significant increase of target expression in target tissues. The proposed intravenous regimen is aiming to saturate, throughout the entire treatment period, CD40 elimination pathways, in conditions where higher CD40 expression is likely FIG. 1 is a schematic representation of the study design of Cohorts 1 and 2 of an ongoing comparative study CCFZ533X2203 (not disclosed).

Cohort 3 comprises two periods:
  1. open-label treatment period (from dosing on Day 1, Week 1 to last dose and completion of assessments on Day 85, Week 13), 2. follow-up period (from Week 13 after completion of last dose to Day 141, Week 21), when patients are followed up for 8 weeks without study medication.

In the open-label treatment period, treatment arm 1 dosing starts with CFZ533 600 mg s.c. once weekly for 4 weeks; in treatment arm 2, dosing starts with CFZ533 10 mg/kg i.v. on Day 1.

Following that, dosing continues with CFZ533 300 mg s.c. once weekly for 4 weeks (treatment arm 1) and 9 weeks (treatment arm 2), respectively.

Figure 2:
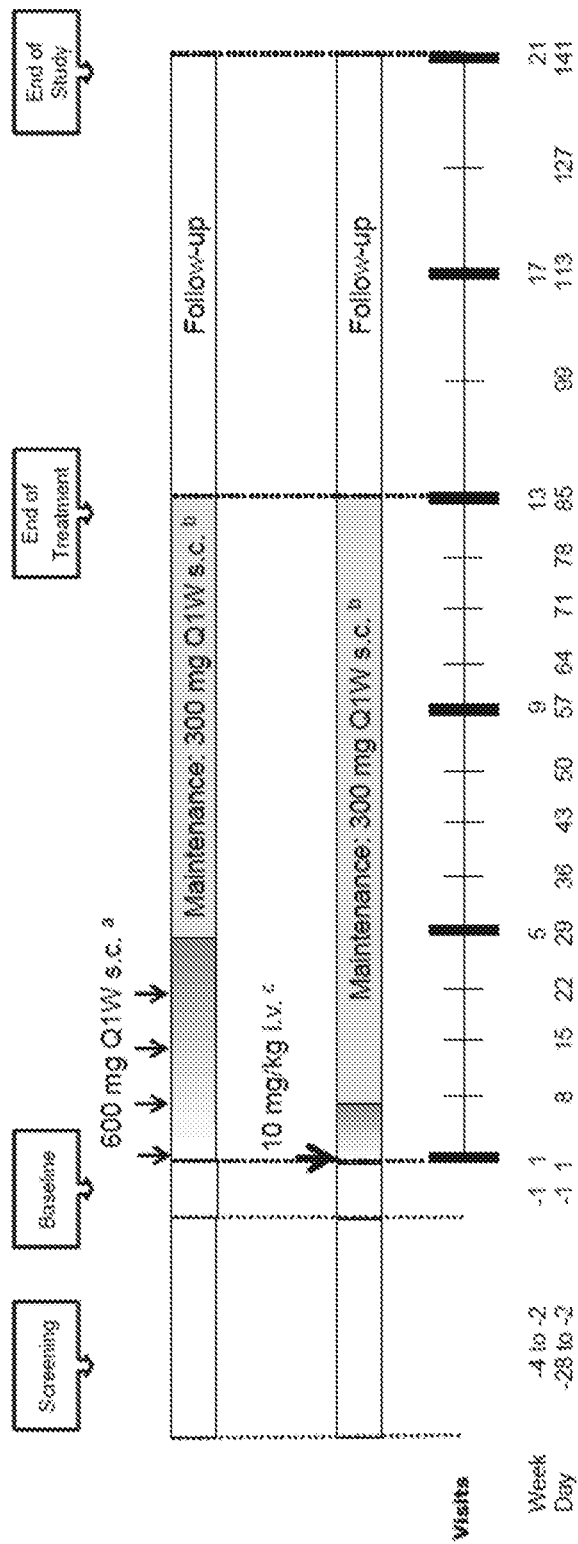
FIG. 2 is a schematic representation of the study design of a third cohort of a comparative study.

FIG. 2 is a schematic representation of the study design of Cohort 3 of an ongoing study comparative study CCFZ533X2203 (not disclosed).

Figure 4:
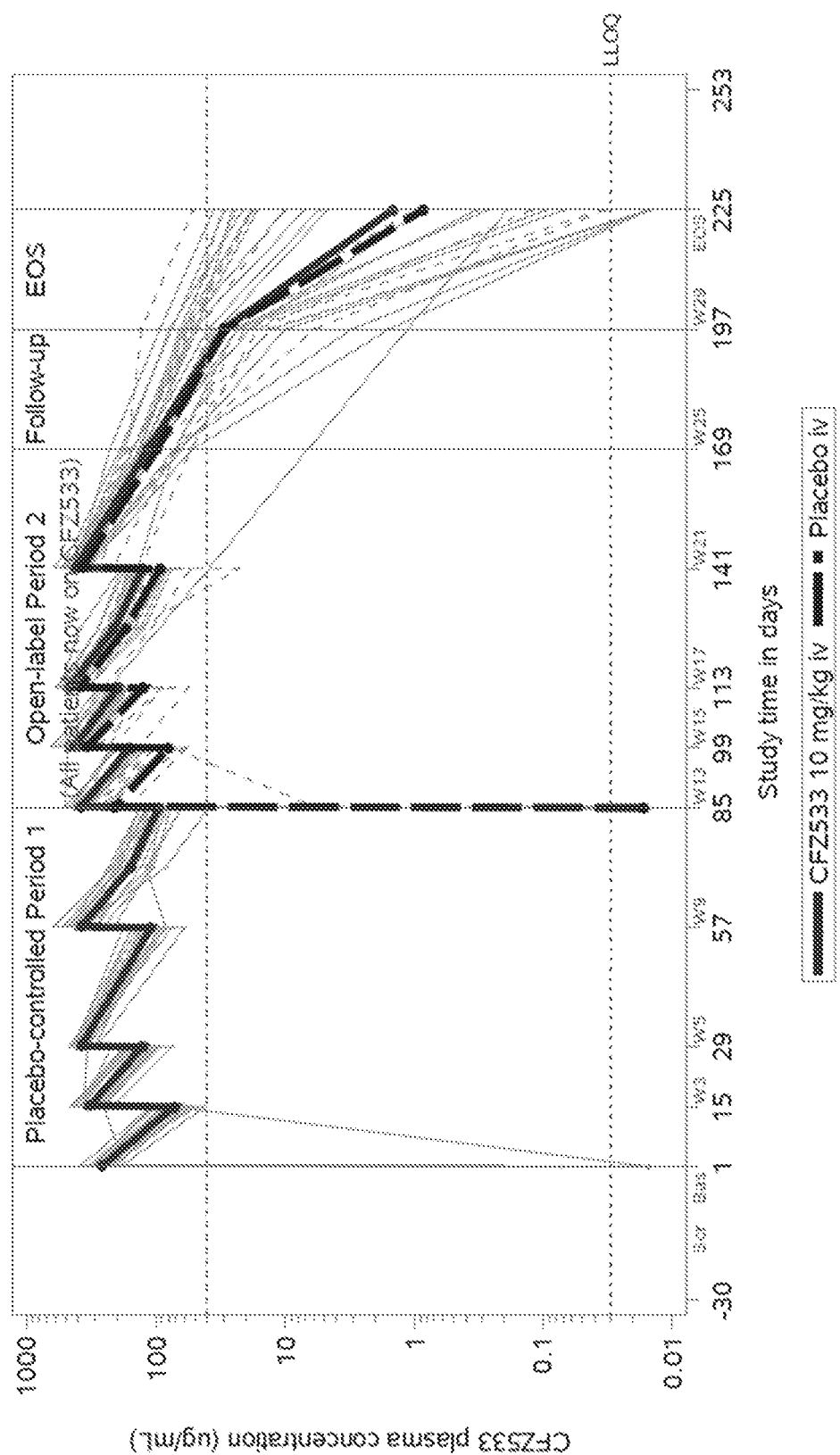
FIG. 4 is a graph showing pharmacokinetic profiles after intravenous administration.

FIG. 4 is a graph showing pharmacokinetics of CFZ533- 10 mg/kg IV. IV regimen provided full target saturation and complete CD40 pathway blockade in target tissues. CD40 pathway blockade in tissue expected with plasma concentration >40 μg/mL (suppression of GC development and T dependent antigen response), dotted line in the graph. After 12/24 weeks of treatment, emerging signs that CD40 expression was down-modulated in some patients.

(1) Comparator and Background Medication

In adult de novo kidney transplant recipients, the use of Tac, MMF, and CS is an approved regimen (e.g. Prograf® PI 2013) and is the current standard of care used in more than 80% of kidney transplants globally. When Tac is combined with an MPA-based regimen and with induction using an IL-2 antagonist, the labeled trough concentration range for Tac is 4-11 ng/mL (e.g. Prograf® PI 2013), and this range will be employed in this clinical study.

CFZ533 will be tested in Part 1 on top of Tac, MMF and CS, and in Part 2 in a Tac/CNI-free regimen with MMF and induction therapy. All concomitant medication will be used according to label.

(2) Tacrolimus (Tac)

Tac is a calcineurin inhibitor that blocks T cell activation and IL-2 transcription. Tac (e.g. Prograf®) is indicated for the prophylaxis of organ rejection in patients receiving allogeneic kidney transplants. It is recommended that Tac be used concomitantly with azathioprine or mycophenolate mofetil (MMF) and adrenal corticosteroids. Therapeutic drug monitoring is recommended for all patients receiving Tac. In kidney transplant patients, the initial dose of Tac (e.g. Prograf®) may be administered within 24 hours of transplantation, but should be delayed until renal function has recovered. In combination with MMF/IL-2 receptor antagonist a starting dose of 0.1 mg/kg/day and a target trough concentration during the first 12 months of 4-11 ng/mL is recommended. The most common adverse reactions (>30%) in kidney transplant patients were infection, tremor, hypertension, abnormal renal function, constipation, diarrhea, headache, abdominal pain, insomnia, nausea, hypomagnesemia, urinary tract infection, hypophosphatemia, peripheral edema, asthenia, pain, hyperlipidemia, hyperkalemia, anemia. For more information on Tac, please refer to the local package insert (e.g. Prograf® PI 2013).

(3) Mycophenolate Mofetil (MMF)

MMF (e.g. CellCept®) is a prodrug of mycophenolic acid (MPA), a reversible inhibitor of inosine monophosphate dehydrogenase (IMPDH) in purine (guanine) biosynthesis which is necessary for the growth of T cells and B cells. Other cells are able to recover purines via a separate salvage pathway and are thus able to escape the effect thus MMF has potent cytostatic effects on lymphocytes. MMF is indicated for the prophylaxis of organ rejection in patients receiving allogeneic renal, cardiac or hepatic transplants. MMF should be used concomitantly with cyclosporine and corticosteroids. A dose of 1 g administered orally twice a day (daily dose of 2 g) is recommended for use in renal transplant patients. MMF (e.g. CellCept®) carries a warning for female patients who may become pregnant. Some manufacturers of MMF recommend male contraception (condom). Use during pregnancy is associated with increased risks of first trimester pregnancy loss and congenital malformations. Females of reproductive potential (FRP) must be counseled regarding pregnancy prevention and planning. Other common side effects of MMF include diarrhea, vomiting, pain, stomach area pain, swelling of the lower legs, ankles and feet, high blood pressure. For more information please refer to the local package insert (e.g. CellCept® PI 2013).

(4) Basiliximab

Basiliximab (e.g. Simulect®) is a chimeric CD25 monoclonal antibody of the IgG1 isotype. It acts as an antagonist at the interleukin-2 (IL-2) binding site of the p55 subunit (Tac antigen) of the high affinity IL-2 receptor (CD25) on the surface of the activated T lymphocytes. Basiliximab is indicated for the prophylaxis of acute organ rejection in patients receiving renal transplantation when used as part of an immunosuppressive regimen that contains cyclosporine and corticosteroids. Basiliximab is for central or peripheral IV administration only. Reconstituted basiliximab should be given either as a bolus injection or diluted to a volume of 25 mL (10 mg vial) of 50 mL (20 mg/vial) with normal saline or dextrose 5% and administered as an IV infusion over 20-30 minutes. The recommended regimen for adult patients is two 20 mg doses; the first dose is suggested to be given within 2 hours prior to transplantation and the second dose is suggested to be given 4 days after transplantation. Bolus administration may be associated with nausea, vomiting and local reactions including pain.

4. Treatment

The following drugs will be used in this study and will be administered in accordance with this protocol and where applicable, current local labeling. Not all dosage forms listed are available in each country, dependent on local approval status and regulations. The treatment regimen to which subjects are randomized comprises of up to four components: MMF (all study parts), CS (all study parts), CFZ533 and/or Tac (both in Part 1; either one in Part 2) and basiliximab (Parts 2 only).

CFZ533 is provided as 150 mg/mL lyophilized open-label bulk medication requiring reconstitution. CFZ533 150 mg/mL concentrate for solution for infusion/solution for injection (liquid in vial) will be introduced. Instructions for preparation and administration to be described in a separate pharmacy manual.

Concomitant medication will be used according to label. Tac (e.g. Prograf® or Generics) as 0.5 mg, 1.0 mg or 5.0 mg capsules or tablets. Mycophenolate mofetil (e.g. CellCept® or Generics) 250 mg or 500 mg film-coated tablets, or 250 mg capsules, or 500 mg vial for IV administration. Basiliximab as 20 mg lyophilized vial for IV administration following reconstitution with sterile water. Corticosteroids (CS) for oral and IV administration, MMF, Tac and basiliximab will be supplied locally.

No additional immunosuppressive agents may be used other than what is defined as per protocol.

In Part 1, subjects will be enrolled into Arm 1. In Part 2, subjects will be randomized to one of the Arms 2A-2B. Study treatments are defined as follow.

Part 1: Arm 1, n=6: CFZ533 at 3.0 mg/kg SC (5 doses; first dose IV)+Tac (4-11 ng/mL)+MMF 1.0 g BID+CS. Part 2: Arm 2A, n=30: Basiliximab 20 mg (Days 1, 4)+CFZ533 at 10 mg/kg IV (17 doses)+MMF 1.0 g BID+CS. Arm 2B Control/Standard of Care, n=15: Basiliximab 20 mg (Days 1, 4)+Tac (4-11 ng/mL)+MMF 1.0 g BID+CS The investigational drug, CFZ533 will be prepared by Novartis and supplied to the Investigators as open-labeled bulk medication.

For preparation of the study medication in Part 2, the unblinded pharmacist or designee at the Investigator's site will need to log into the IRT system to receive the treatment code. In addition, the unblinded pharmacist or designee at the Investigator's site will prepare the medication for administration to subjects based on a separate pharmacy manual. Appropriate documentation of the subject specific dispensing process must be maintained. Bulk medication labels will be in the local language, will comply with the legal requirements of each country, and will include storage conditions for the drug but no information about the subject.

(1) Induction Therapy

For patients randomized to the control arm or where Tac, MMF and/or steroids are to be administered per protocol, they may be administered prior to transplant according to center practice but such practice must be applied consistently to all subjects at a given center. At randomization/enrollment, all subjects must follow the assigned regimen. Pre-transplant immunosuppression, including induction therapy and any Tac or MMF should be recorded on the Concomitant medication eCRF under the Immunosuppressive category.

(2) Basiliximab Induction Therapy

Subjects randomized to receive induction therapy will receive 2×20 mg doses of basiliximab administered IV. The first dose should be given within 2 hours prior to transplant surgery, and the second dose should be administered on Day 4 post-transplant, or according to local practice.

The 20 mg vial should be reconstituted with 5 mL sterile water. The resultant solution is isotonic and may be injected as an IV bolus. Alternatively, the solution may be diluted to a volume of 50 mL with sterile saline and 5% dextrose and administered as an infusion over 30 minutes. If venous irritation occurs following bolus administration, the next dose (if appropriate) should be administered as a 30 minute infusion. There is no maintenance dose, and no other antibodies are permitted for induction therapy. All basiliximab doses and changes must be recorded in the Concomitant Medications eCRF under the Immunosuppressive category.

(3) CFZ533 Therapy

CFZ533 will be administered by IV infusion or SC injection to the patient by authorized Investigator staff at each visit.

The first dose of CFZ533 will be administered IV pre-transplant or intra-operatively. Drug administration will begin after randomization/enrollment and must be completed up to 6 hours prior to or at the time of unclamping.

The study medication preparation and administration guidelines are described in a separate pharmacy manual. The subject will be weighed at the Baseline visit and this weight value will be used for the initial study medication preparation and the calculation of the dose. Most actual weight will serve as basis for further dose calculations.

All dosages prescribed and dispensed to the subject and all dose changes during the study must be recorded on the CFZ533 Dose Administration Record eCRF. Patients can be released after each treatment if deemed appropriate by the Investigator.

(4) MMD Administration

Mycophenolate mofetil will be 2 tablets of 500 mg or 4 capsules of 250 mg b.i.d. (2 g/day). For patients who remain intubated >24 hours post-transplant and/or whom are otherwise unable to swallow oral medication, IV MMF may be substituted until oral conversion is possible.

The first dose of MMF will be administered immediately after randomization/enrollment and no later than 24 hours after graft reperfusion of the allograft or according to local practice.

All MMF doses and changes must be recorded on the MMF Dose Administration Record eCRF (Part 1) and Concomitant Medications eCRF under the Immunosuppressive category (Part 2).

(5) Tacrolimus Administration

Tac will be administered as PO capsules b.i.d. and adjusted to maintain within the target ranges of 4-11 ng/mL. Tac should be initiated as soon as possible and no later than 24 hours after reperfusion of the graft. The lowest permitted dosing of Tac in this study is 0.5 mg b.i.d. If Tac is discontinued for more than 21 consecutive days, and the study regimen cannot be maintained, the patient must be discontinued from the randomized treatment and managed per local practice. Subjects who discontinue their study regimen are expected to remain in the study on standard of care to Month 6 in Part 1 or Month 12 in Part 2.

Tac dosing will be modified by Investigators as needed and recorded on the Tacrolimus Dosage Administration Record (Part 1) and Concomitant Medication (Part 2) eCRF at each visit. In the event of Tac intolerance (e.g., nephrotoxicity, neurotoxicity) dose reduction of Tac may be necessary. If it occurs that the Tac trough level is outside the required target level, then the Investigator will be asked to confirm the intended Tac trough level, to record the start date and reason for dose reduction on the Tacrolimus Dosage Administration Record (Part 1) and Concomitant Medication (Part 2) eCRF.

The co-administration of drugs known to interfere with Tac metabolism should be avoided if possible. If these drugs are required, the Investigator should carefully monitor Tac trough levels.

The patient will be instructed to record the time of the last dose on the day prior to the blood draw and to bring the morning dose to the visit so it may be administered after the blood sampling is completed.

(6) Corticosteroids

Corticosteroids (CS) will be administered according to local standard practice in a way that is consistent in all patients enrolled at each site. Dosing of CS should be recorded in the Concomitant Medications eCRF under the Immunosuppressive category.

5. Results

CD40 signaling has been associated with the pathogenesis of autoimmune diseases (AD), and patients with systemic ADs generally present with increased CD40 expression and elevated serum/plasma sCD40 levels.

CFZ533 is subject to target-mediated disposition (TMD), a process in which a significant proportion of CFZ533 (relative to dose) is bound with high affinity to CD40 such that this interaction is reflected in the PK profile of CFZ533. In such circumstances additional factors to consider for defining the appropriate posology to treat solid organ transplantation patients include CD40 expression level in the body, CD40 synthesis and degradation (the biology of the target), and CFZ533-CD40 binding kinetics.

Previous clinical experience with CFZ533 in healthy volunteers, rheumatoid arthritis, primary Sjögren's Syndrome, kidney transplantation, liver transplantation, Grave's disease and myasthenia gravis patients, has shown that elevated CD40 expression is associated with high elimination (clearance) rate of CFZ533, loss of target engagement and loss of CD40 pathway blockade in target tissues, if CD40 is not fully saturated. Under full CD40 occupancy, the contribution of CD40 to the overall clearance of CFZ533 is minimal, and the disposition of CFZ533 is mainly the consequence of CFZ533 binding to FcRn receptors (a high capacity receptor responsible for IgG homeostasis by recycling/salvage. FIG. 4 shows plasma concentration of CFZ533 in patients dosed according to the regimen disclosed in FIGS. 1 and 2, study CCFZ533X2203 (not disclosed herein).

From a pharmacokinetic/pharmacodynamic perspective and dose finding strategy, it is likely that an appropriate posology in patients would include a loading regimen followed by maintenance regimen.

The loading regimen, likely during the first month, through IV or SC administration is justified because CFZ533 is subject to CD40 mediated elimination. If CD40 is not fully saturated at start of treatment, in conditions of elevated CD40 expression, a high elimination (clearance) rate of CFZ533 is likely to be associated with loss of target engagement and loss of CD40 pathway blockade in target tissues. After the loading period, and based on preliminary modeling using PK data from the ongoing study CCFZ533X2203 (not disclosed herein) in patients a SC maintenance regimen will be selected to ensure full CD40 pathway blockade in target tissues.

Figure 11:
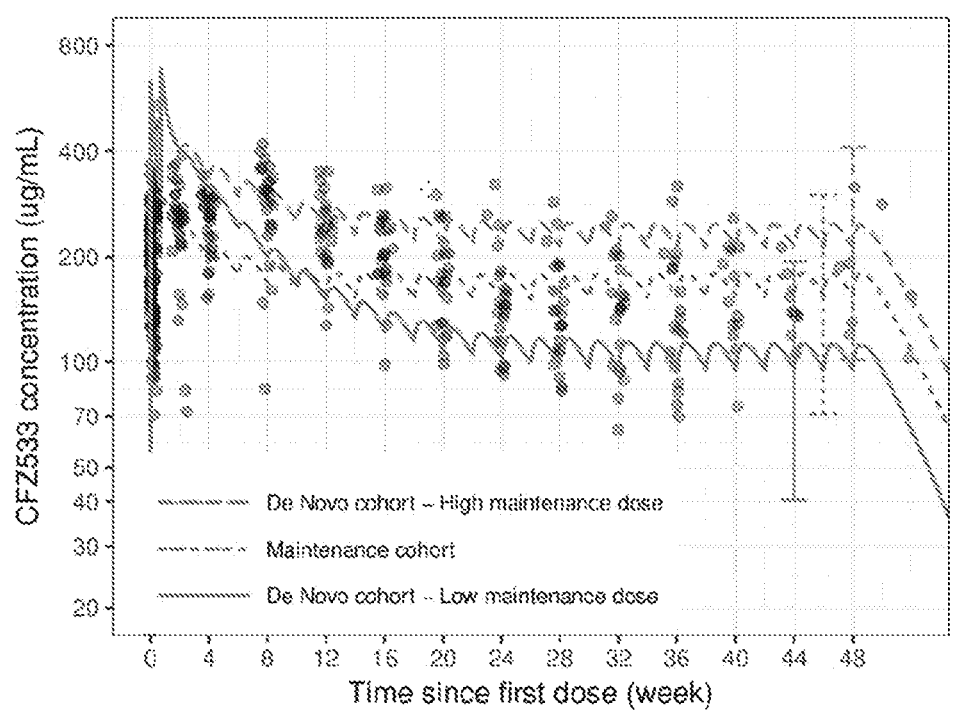
FIG. 11 is representing the predicted plasma concentration-time profiles for CFZ533 in de novo kidney transplant patients and in maintenance kidney transplant patients plotted together with actual CFZ533 plasma concentrations.

FIG. 11 is representing the predicted plasma concentration-time profiles for CFZ533 in de novo kidney transplant patients and in maintenance kidney transplant patients plotted together with actual CFZ533 plasma concentrations.

The lines represent the predicted time-course of the CFZ533 plasma concentration for the typical transplant patient (de novo transplant patients; 600 mg SC Q2W maintenance regimen—long dashed line, or 300 mg SC Q2W maintenance regimen—solid line; or 450 mg SC Q2W maintenance regimen—short dashed line). For each of these regimens, the 90% prediction intervals for the trough CFZ533 plasma concentration at steady state are displayed. Those predictions are for patients with body weight ranging from 50 to 120 kg. The CFZ533 plasma concentrations measured in a separate study are displayed as grey dots. Predictions are based on a model fit to the data from a first-in-human study and a transplant study.

The posterior mean tBPAR rate was presented together with the 95% credible interval, the number of patients with tBPAR and the posterior probabilities of being above the thresholds, 10%, 15%, 20%, and 25%. A plot of the posterior probability distribution for the tBPAR rate was provided.

The pre-defined success criteria was considered to be a tBPAR rate difference between the CFZ533 arm and the control group of less than 20 percentage points with at least 60% level of proof.

Overall results of the study are shown in Table 2.

TABLE 2

Overall study results.

|  | CFZ533 + TAC + MMF (part 1) | CFZ533 + MMF (part 2) | Tac + MMF (part 2) |
| --- | --- | --- | --- |
| Started | 7 | 34 | 18 |
| Completed | 6 | 30 | 13 |
| Not Completed | 1 | 4 | 5 |
| Graft Loss | 0 | 0 | 2 |
| Withdrawal by Subject | 0 | 0 | 2 |
| Lost to Follow-up | 0 | 0 | 1 |
| Lack of Efficacy | 0 | 1 | 0 |
| Physician Decision | 1 | 3 | 0 |

An overview of the pharmacokinetic parameters are found in Table 3.

TABLE 3

Pharmacokinetic results.

|  | CFZ533 + TAC + MMF (part 1) | Unit |
| --- | --- | --- |
| Number of Participants Analyzed | 7 | participants |
| Mean Cmax Pharmacokinetic Parameter-Part I (Mean ± Standard Deviation) | 66.3 ± 12.3 | ug/mL |
| Mean Tmax Pharmacokinetic Parameter - Part I (Median (Full Range)) | 0.237 (0 to 1.02) | day |
| Mean AUClast Pharmacokinetic Parameter - Part I (Mean ± Standard Deviation) | 367 ± 52.0 | day*ug/mL |

Efficacy as defined by the frequency and severity (Banff classification) of treated biopsy proven acute rejection (tBPAR) is shown in Table 4 (adjudicated data).

TABLE 4

Efficacy overview.

|  | CFZ533 + MMF (part 2) | Tac + MMF (part 2) |
| --- | --- | --- |
| Number of Participants Analyzed [units: participants] | 33 | 18 |
| Efficacy as defined by the frequency and severity (Banff classification) of treated biopsy proven acute rejection (tBPAR) adjudicated data - Part II (units: events) | | |
| Month 3 | 6 | 2 |
| Month 6 | 7 | 3 |
| Month 9 | 7 | 3 |
| Month 12 | 7 | 3 |

An overview of the statistical analysis of the efficacy data is shown in Table 5.

TABLE 5

Statistical analysis.

| Groups | CFZ533 + MMF (part 2), Tac + MMF (part 2) | |
| --- | --- | --- |
| P Value | 0.8976 | |
| Method | Other Bayesian posterior probability | Posterior probability that the composite efficacy failure difference between CFZ533 and Tac is <20%. |

TABLE 5-continued

Statistical analysis.

| | | |
|---|---|---|
| Mean Difference (Final Values) | 0.095 | Month 3 |
| 95% Confidence Interval 2-Sided | −0.067 to 0.263 | |
| Groups | CFZ533 + MMF (part 2), Tac + MMF (part 2) | |
| P Value | 0.8836 | |
| Method | Other Bayesian posterior probability | Posterior probability that the composite efficacy failure difference between CFZ533 and Tac is <20%. |
| Mean Difference (Final Values) | 0.093 | Month 6 |
| 95% Confidence Interval 2-Sided | −0.084 to 0.271 | |
| Groups | CFZ533 + MMF (part 2), Tac + MMF (part 2) | |
| P Value | 0.8822 | |
| Method | Other Bayesian posterior probability | Posterior probability that the composite efficacy failure difference between CFZ533 and Tac is <20%. |
| Mean Difference (Final Values) | 0.093 | Month 9 |
| 95% Confidence Interval 2-Sided | −0.085 to 0.272 | |
| Groups | CFZ533 + MMF (part 2), Tac + MMF (part 2) | |
| P Value | 0.8821 | |
| Method | Other Bayesian posterior probability | Posterior probability that the composite efficacy failure difference between CFZ533 and Tac is <20%. |
| Mean Difference (Final Values) | 0.093 | Month 12 |
| 95% Confidence Interval 2-Sided | −0.087 to 0.273 | |

The eGFR in Part 2 is shown in Table 6.

TABLE 6 eGFR in Part 2.

| | CFZ533 + MMF (part 2) | Tac + MMF (part 2) |
|---|---|---|
| Number of Participants analyzed [units: participants] | 32 | 18 |
| eGFR - Part 2 [units: ml/min] Mean (90% confidence interval) | | |
| Day 1 | 9.8 (8.3 to 11.3) | 9.7 (7.7 to 11.8) |
| Day 29 | 55.6 (50.4 to 60.7) | 44.3 (37.2 to 51.4) |
| Day 337 | 58.2 (52.2 to 64.2) | 44.2 (36.1 to 52.3) |

An summary of adverse events (AEs) is seen in Table 7. AEs were collected from First Patient First Visit (FPFV) until Last Patient Last Visit (LPLV).

TABLE 7

Overview of adverse events.

| | CFZ533 + TAC + MMF (Part 1) N = 7 | CFZ533 + MMF (Part 2) N = 34 | TAC + MMF (Part 2) N = 18 | Total N = 59 |
|---|---|---|---|---|
| Total participants affected by Serious adverse events | 4 (57.14%) | 21 (61.76%) | 12 (66.67%) | 37 (62.71%) |

TABLE 7-continued

Overview of adverse events.

| | CFZ533 + TAC + MMF (Part 1) N = 7 | CFZ533 + MMF (Part 2) N = 34 | TAC + MMF (Part 2) N = 18 | Total N = 59 |
|---|---|---|---|---|
| Total patients affected by Other adverse events | 7 (100.00%) | 33 (97.06%) | 18 (100.00%) | 58 (98.31%) |

In conclusion, this study shows that patients in the CFZ533 arm had significantly better renal function throughout the study; the difference in eGFR being approximately 10 mL/min and the risk for acute rejection was similar to that of patients treated with Tac.

The rate of reported BPAR was rather high in both treatment arms most likely due to extra investigator vigilance after the recently failed competitor trial. Thus, the independent, blinded AC was crucial for the success of the trial providing important learnings for future transplant studies.

The study also shows that the risk for NODAT seems much lower with CFZ533 patients (0% of pateints treated with CFZ533+TAC+MMF, Part 1; 8.82% of patients treated with CFZ533+MMF, Part 2; compared to 16.67% of patients treated with TAC+MMF, Part 2) and if anything there was a tendency to fewer complications with CFZ533 than with Tac. Thus, CFZ533 was well tolerated and the safety profile, PK and efficacy results support further development into Phase II/III trials.

Example 8. Characterization of the In Vitro and In Vivo Properties of CFZ533, a Blocking and Non-Depleting Anti-CD40 Monoclonal Antibody 1. Methods Surface Plasmon Resonance Analysis of Affinity of CFZ533 for CD40

The binding analyses of recombinant CFZ533 were performed at 25° C. with HBS–EP+ as running buffer. A typical binding analysis cycle consisted of three steps: (i) capture of the antibody via ProteinA immobilized on the chip surface, (ii) binding of CD40 antigen to the captured anti-CD40 antibody, and (iii) regeneration of the ProteinA surface. To determine the kinetic rate constants of the antigen-antibody binding interactions, binding data were processed, double referenced with responses from blank injections. The binding curves were fitted locally using the 1:1 interaction model of the Biacore T100 Evaluation software to determine kinetic rate constants. The value for the equilibrium dissociation constant (KD) was calculated as the ratio of the rate constants kd/ka. All binding measurements were performed in two independent experiments.

Surface Plasmon Resonance Analysis of Affinity of CFZ533 for FcγRIIIA

Extracellular domains of human FcγRIIIA tagged with a 4-amino acid purification tag (4APP; Novartis) and an Avi biotinylation tag (GLNDIFEAQKIEWHE; Avidity) were synthesized by Geneart: human FcγRIIIA (CD16a) 158V (Uniprot: P08637, 17-199), human FcγRIIIA 158F (Uniprot: P08637, 17-199), expressed in HEK293 cells and purified with anti-4APP affinity chromatography. Receptors were site directed biotinylated with BirA (Avidity), bound to streptavidin sensor chips (General Electric), and the equilibrium-binding levels of the different Abs were analyzed by surface plasmon resonance (T100, General Electric) as described (Warncke et al. 2012). Equilibrium dissociation constants ($K_D$) were calculated by a 1:1 model.

Human Leukocyte Cultures

Whole blood buffy coats were obtained from healthy volunteers (Blutspendezentrum, Basel, Switzerland) or whole blood collected from healthy volunteers provided under informed consent in accordance with the Swiss Human Research Act and approval of the responsible ethic committee (Ethikkommission Nordwest- and Zentralschweiz; EKNZ). Human tonsil samples were obtained from both Ergolz Klinik (Liestal, Switzerland) (Study Protocol No. 1000244 v.03; approved by Ethikkommission beider Basel; EKBB) and Kantonspital (Liestal, Switzerland) (Study Protocol No. TRI0149 v.01; approved by EKNZ). For in vitro culture experiments, please see supplementary material for detailed methods. Briefly, whole blood, isolated PBMCs, in vitro derived monocyte DCs or human tonsil B cells were incubated with single concentrations or a dose titration of CFZ533 or relevant control antibodies. For pathway blocking experiments, these cultures also included an EC80 concentration of recombinant human CD154 (5 μg/ml) and IL-4 (75 ng/ml). Readouts for in vitro assays included proliferation assessed by thymidine incorporation ($^3$H-TdR), flow cytometric-based assessment of expression of the activation molecule CD69 on B cells, and cytokine secretion assessed by ELISA. Similar assays were used for NHP whole blood and PBMCs. In some human whole blood experiments, CD40 receptor occupancy was also examined by used of a fluorescently tagged CFZ533. Where appropriate, IC50 values were estimated using linear regression-based curve-fitting in GraphPad Prism® software.

In Vitro Cell Depletion Assays

See supplementary material for detailed methods. Briefly, the ability of CFZ533 to mediated depletion of CD20$^{pos}$ B cells was monitored in human whole blood over a period of three days in comparison to the B cell depleting antibody Rituximab. For CDC, CFZ533 or Rituximab were incubated with RAJI B cells in the presence or absence of rabbit complement and cell lysis was assessed by luminescence.

Internalization of CFZ533

Internalization of fluorescently tagged CFZ533 and rCD154 was assessed in vitro using the human B cell line RI-1 (Th'ng et al, 1987). CD40 dependence of CFZ533 internalization was assessed using a CD40 knockout RI-1 cell line. Internalization was assessed using an Amnis® image flow cytometer (Merck KHaA, Darnstadt) according to the manufacturer's instructions and data analyzed using ImageStream®$^X$ software.

In Vivo Studies

Single dose pharmacokinetic/pharmacodynamic (PK/PD) studies utilized biologics-treatment naive cynomolgus monkeys (*Macaca fascicularis*) between 7.5-8.5 years old (6.5±2.6 kg) and captive-bred from Philippines (Siconbrec, Makati City, Philippines). Animal handling, care, drug treatments and blood sampling are performed according to the Swiss Federal Law for animal protection (animal licenses BS #1900, BS #1495). For the recall immunization experiments, we utilized animals from a toxicology study conducted at Covance Laboratories GmbH, Muenster, Germany, (manuscript in preparation). The study was performed according to an authorized study protocol and local standard operating procedures in strict compliance with national legal regulations on animal welfare law and accepted animal welfare standards.

In the PK study, CFZ533 was administered to three animals at calculated single doses of 16.2 (5532), 18.5 (5531) and 20 (5530) mg/kg. Blood was sampled for analyses of CFZ533 serum concentrations, numbers of peripheral T and B lymphocytes, and CD40 occupancy on peripheral B cells by CFZ533. For recall TDAR experiments, animals were immunized with keyhole limpet hemocyanin (KLH) in Alum on study days 8 (priming) and 43 (recall; during CFZ533 treatment) respectively. Serum was sampled one day before and 7, 14 and 21 days after priming and recall immunizations. KLH specific IgM/IgG titers were determined with sandwich ELISA using cynomolgus monkey anti-KLH IgM/IgG reference serum as standard. PK assessment was performed as described above. See supplementary material for additional details on the PK and TDAR experiments.

Histological Analysis of Germinal Centers

Sections of formalin fixed, embedded in paraffin wax (FFPE) spleen and lymph nodes (axillary, mandibular and mesenteric) stained with hematoxylin and eosin as well as with an indirect immune-peroxidase method (HRP+DAB from Dako) with the following markers: anti-CD20 antibody (M0755, Dako), anti-CD8 antibody (RM-9116-SO, Medac) and Ki67 (M7240, Dako). All slides were assessed and graded according to the intensity of the staining (negative to intense). In addition, the staining pattern and distribution of any immunohistochemical stained cells within the tissue were also described.

2. Results

CFZ533 Binds Human CD40 and Inhibits rCD154-Induced Activation of Multiple CD40 Expressing Cell Types Table 8 indicates that the KD of CFZ533 for recombinant human CD40 was determined by surface plasmon resonance as 0.3 nM, thus being very similar to its parental antibody HCD122 (wild-type IgG1 version of CFZ533).

TABLE 8

Binding affinities (KD) and kinetics of HCD122 and CFZ533 to human CD40.

| | HCD122 | CFZ533 |
|---|---|---|
| $K_D$ [M] | $4.67 \pm 1.00 \times 10^{-10}$ | $3.05 \pm 0.26 \times 10^{-10}$ |
| $k_a$ [1/Ms] | $2.84 \pm 0.67 \times 10^{5}$ | $3.13 \pm 0.73 \times 10^{5}$ |
| $k_d$ [1/s] | $1.26 \pm 0.03 \times 10^{-4}$ | $0.93 \pm 0.14 \times 10^{-4}$ |
| Chi$^2$[RU$^2$] | 0.17-0.19 | 0.10-0.15 |

Figure 5:
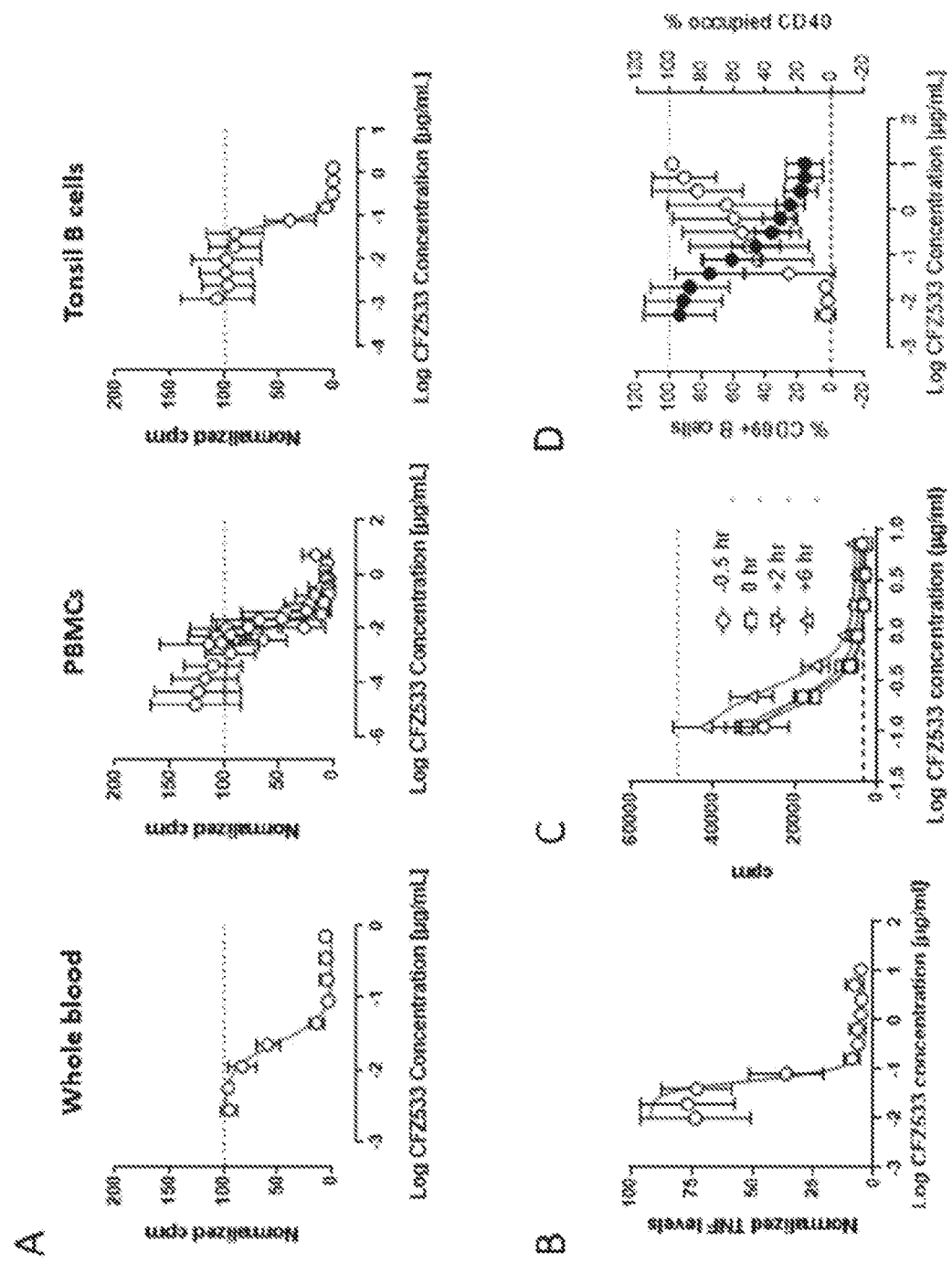
FIG. 5 is graphs shows CFZ533 inhibition of the rCD154-induced pathway activation.

FIG. 5A shows effect of CFZ533 on rCD154 and IL-4-mediated proliferation (3H-TdR) of human whole blood cultures, PBMCs, and isolated tonsil B cells from multiple donors (5, 32 and 6 donors respectively). Data is presented as normalized cpm (rCD154+IL-4=100; dotted lines). FIG. 5B shows CFZ533 inhibited TNF-alpha production by rCD154-stimulated moDCs after overnight culture. FIG. 5C shows delayed addition of CFZ533 inhibited rCD154+IL-4 mediated human PBMC proliferation. CFZ533 was added to human PBMCs one hour before, simultaneously with, or two and six hours after stimulation with rCD154+IL-4, and proliferation (3H-TdR) was assessed after a subsequent four days of culture (dotted and dashed lines represent rCD154+ IL-4 and cell plus media controls). For all data, the mean and SD of readouts of rCD154-induced stimulation were graphed as a function of log-transformed CFZ533 concentrations. Where appropriate, IC50 values were determined using linear regression based curve-fitting. FIG. 5D shows relationship between CD40 occupancy and pathway blockade by CFZ533. Human whole blood from 10 donors was cultured overnight with rCD154 in presence of a dose titration of CFZ533. The degree of pathway activation (% CD69pos on B cells) and degree of CD40 occupancy (staining with AlexaFlour 488 labeled CFZ533) was evaluated. Open and filled circles indicate the percent of CD40 occupied by CFZ533 and percent CD69pos expressing cells on CD20pos B cells as a function of log-transformed CFZ533 concentration respectively (Mean and SD shown). Dotted and dashed lines represent rCD154-induced CD69 expression and cells plus media control cultures normalized across all donors.

FIG. 5A indicates that CFZ533 completely inhibited rCD154-induced proliferation of human whole blood cultures, PBMCs as well as purified tonsillar B cells from multiple donors with potencies (IC50 values) of 0.024 µg/ml (0.16 nM), 0.017 µg/ml (0.12 nM) and 0.071 µg/ml (0.47 nM) respectively. In addition, we could demonstrate that CFZ533 completely blocked rCD154-induced TNF production by primary monocyte-derived dendritic cells (moDCs) with an IC50 of 0.04 µg/ml (0.27 nM) (FIG. 5B).

As published previously, CFZ533 inhibited rCD154-induced proliferation of PBMCs from Cynomolgus monkeys (Cordoba et al., 2015). CFZ533 inhibited rCD154-induced proliferation of PBMCs from humans, rhesus and cynomolgus animals with similar potency (IC50 of 0.02, 0.03, and 0.01 µg/ml, respectively), and could also bind CD40 on B cells from these species with EC50 values of approximately 0.2 µg/ml, see Table 9.

TABLE 9

Cellular binding and functional properties of CFZ533 in human and NHPs.

| | Inhibition of rCD154-induced proliferation (IC50 PBMCs) | CD40 occupancy by CFZ533 (MFI EC50 on CD20 + cells) |
|---|---|---|
| Human | 0.017 + 0.012 µg/ml<br>0.12 + 0.08 µM<br>(n = 32) | 0.22 + 0.042 µg/ml<br>1.49 + 0.28 µM<br>(n = 4) |
| Rhesus | 0.026 + 0.017 µg/ml<br>0.18 + 0.12 µM<br>(n = 8) | 0.22 + 0.033 µg/ml<br>1.49 + 0.22 µM<br>(n = 6) |
| Cynomolgus | 0.010 + 0.003 µg/ml<br>0.07 + 0.02 µM<br>(n = 4) | 0.20 + 0.068 µg/ml<br>1.35 + 0.46 µM<br>(n = 4) |

The above cellular data were derived from experiments where CFZ533 was added prior to, or simultaneously with rCD154, indicating that the antibody could prevent binding of the endogenous ligand. We could also demonstrate that addition of CFZ533 up to 6 hours following initiation of leukocyte cultures containing rCD154 resulted in complete inhibition of cellular activation with minimal loss of potency, indicating that CFZ533 could displace the endogenous ligand from CD40 (FIG. 5C).

We also wanted to evaluate the relationship between the degree of CD40 occupancy by CFZ533, and the extent of pathway inhibition. To do so we simultaneously assessed CD40 receptor occupancy by CFZ533 and rCD154-induced CD69 in whole blood from multiple donors. FIG. 5D indicates that CD40 receptor occupancy by CFZ533 of at least 90% was required for complete blockade of CD40 pathway activation. A similar relationship between receptor occupancy and pathway inhibition was also observed using CD23 and CD54 as Readouts of CD40 Pathway Activation (Data not Shown).

CFZ533 Displays Minimal Stimulatory Potential In Vitro

Figure 6:
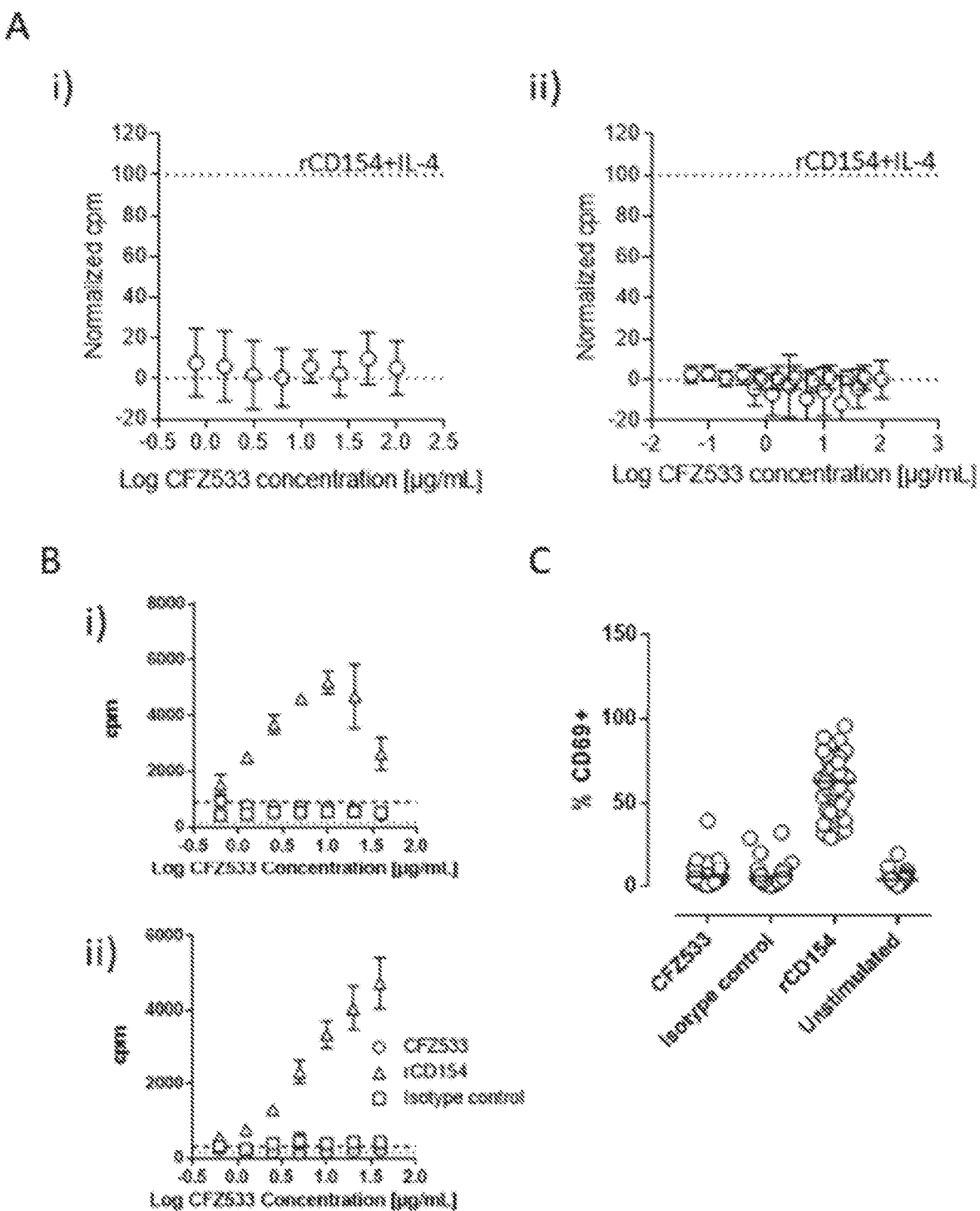
FIG. 6 is graphs showing CFZ533 minimal stimulatory activity in vitro.

The ability of CFZ533 to stimulate activation of human leukocytes was assessed using proliferation and upregulation of the activation molecule CD69 on B cells in whole blood. FIG. 6A shows data regarding i. Human whole blood from multiple donors (n=13) were incubated with a dose titration of CFZ533, and proliferation ($^3$H-TdR) was assessed after three days of culture. ii. Human PBMCs from multiple donors (n=26) were incubated with a dose titration of CFZ533, and proliferation ($^3$H-TdR) was assessed after three days of culture. For both graphs, data is presented as mean and SD of normalized cpm as a function of log-transformed CFZ533 concentration (rCD154+IL-4=100; dotted lines, cells plus media=0; dashed lines). FIG. 6B shows that CFZ533 does not induce human PBMC proliferation in the presence of additional stimuli. Human PBMCs were stimulated for 3 days with a dose titration of CFZ533 in the presence of IL-4 (i) or anti-IgM F(ab')2. (ii). The mean and SD of 3H-TdR (cpm) is shown as a function of log-transformed CFZ533 concentration. In FIG. 6C it is shown how human whole blood (41 donors) was cultured overnight with no stimuli, CFZ533, isotype control or rCD154 and CD69 expression on B cells was assessed by FACS. Each dot represents data from a single donor with mean % CD69 values indicated by a horizontal red line.

FIG. 6A shows that CFZ533 was unable to induce thymidine incorporation by human whole blood (1:10 dilution) or PBMCs in contrast to rCD154. The inability of CFZ533 to induce proliferation was unaffected by the addition of additional co-stimuli such as IL-4, or anti-IgM (FIG. 6B). We could also demonstrate that CFZ533 was unable to induce upregulation of CD69 on B cells in whole blood from multiple donors, again in contrast to rCD154 (FIG. 6C). Finally, CFZ533 was unable to induce cytokine production by CD40 expressing monocyte-derived DCs or human umbilical vein endothelial cells (HUVECs) (data not shown).

CFZ533 does not Mediate Cell Depletion

CFZ533 was engineered to contain a N297A mutation, previously demonstrated to abrogate FcγR binding resulting in an inability to mediate antibody-dependent cellular cytotoxicity (ADCC). CFZ533 was not able to bind FcγRIIIA in comparison to HCD122 (wild-type IgG1) (Table 10), and we wanted to examine how this lack of binding affected the ability of CFZ533 to mediate cell depletion.

TABLE 10

Binding affinities ($k_a$[1/M]) of HCD122 and CFZ533 to human FcγRIIIA

| FcγR species | HCD122 (wild-type IgG1) | CFZ533 (N297A IgG1) |
|---|---|---|
| Human FcγRIIIA 158V | 1.72 × 106 | n.d. |
| Human FcγRIIIA 158F | 6.99 × 105 | n.d. | n.d. not detected

Figure 7:
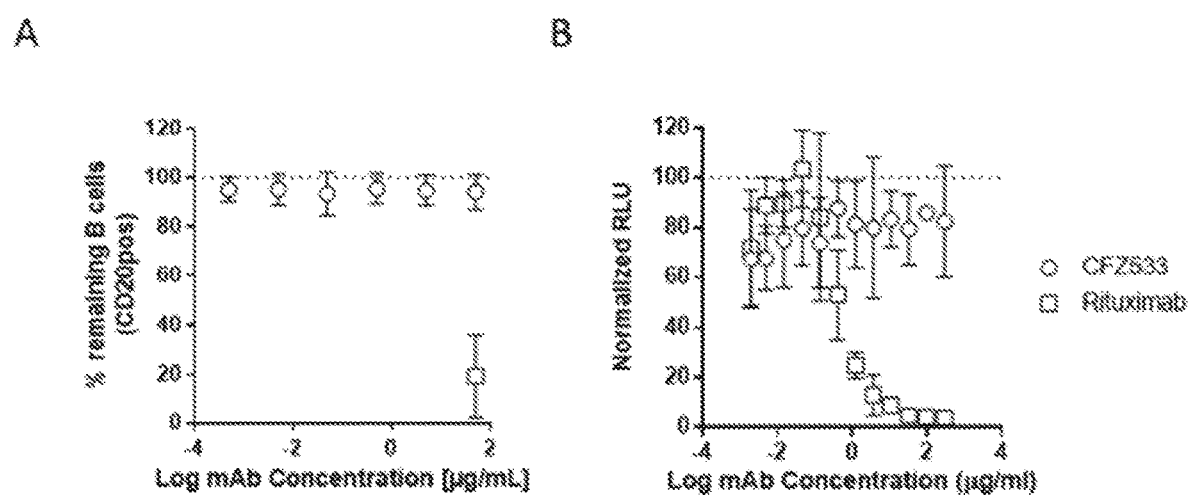
FIG. 7 is graphs showing that CFZ533 does not mediate cell depletion.

FIG. 7A shows data from human whole blood cultures incubated for 72 hours in the presence of a dose titration of CFZ533 or 50 μg/ml Rituximab. B cells numbers were determined based on CD45pos and CD19pos events falling within lymphocyte FSC (forward-scattered light)/SSC (side-scattered light) gate. Results for individual antibody concentrations were calculated as percent remaining B cells with reference to untreated samples and graphed as a function of log-transformed antibody concentration (adjusted to 100% and shown as a dotted line). Data represent the mean and SD of eight independent donors. FIG. 7B shows results from Raji B cells incubated with different concentrations of Rituximab or CFZ533 and a fixed concentration of rabbit complement. Concentration dependent killing of the Raji cells was analyzed after 2 hours, where the viability of the cells was measured by determination of the ATP concentration in each well using luciferase. Results are presented as isotype-control normalized relative luciferase units (RLU) as a function of log-transformed antibody concentration.

FIG. 7A indicates that while the depleting anti-CD20 antibody Rituximab was able to eliminate approximately 80% of B cells in human whole blood, while CFZ533 failed to mediate any cell depletion. In addition, CFZ533 was unable to mediate complement-dependent cytotoxicity (CDC) of Raji B cells, in contrast to Rituximab (FIG. 7B).

CFZ533 is Internalized by B Cells in a CD40-Dependent Manner

Figure 8:
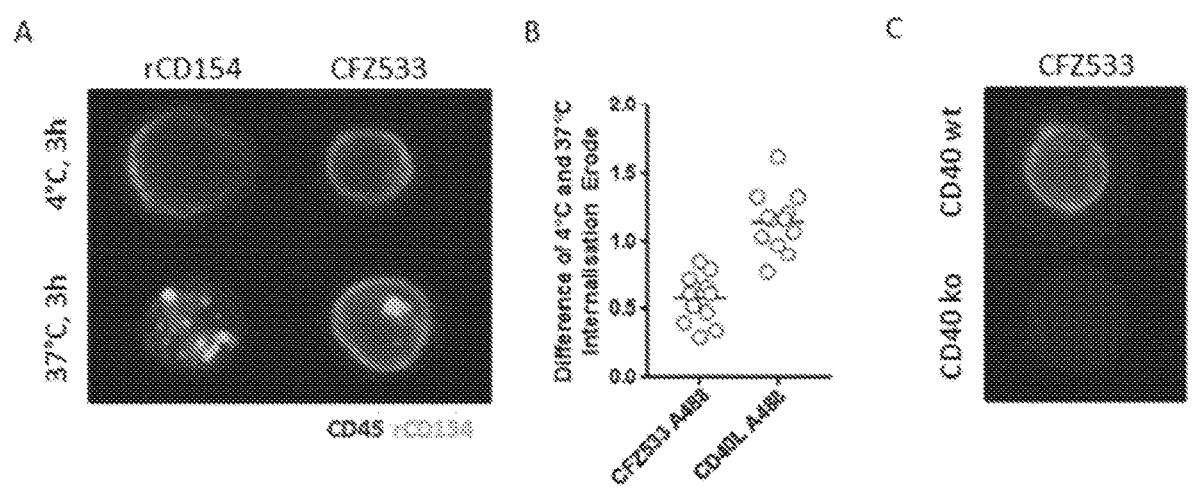
FIG. 8 is representative images of individual RI-1 B cells.

We next wanted to examine whether CFZ533 could be internalized by the CD40 expressing human B cell line RI-1. FIG. 8A indicates that rCD154 was internalized under permissive conditions (37° C.) in comparison to non-permissive conditions (4° C.), where weak staining of rCD154 could be observed on the plasma membrane. CFZ533 was also internalized, although there did appear to be residual membrane staining at 37° C. FIG. 8B indicated that the extent of internalization of rCD154 appeared to be greater than that observed for CFZ533. Using a CD40 knockout RI-1 B cell line, we could demonstrate that binding and internalization of CFZ533 (FIG. 8C) and rCD154 (data not shown) was CD40 dependent.

FIG. 8A shows Representative images of individual RI-1 B cells cultured with AlexaFlour 488 labeled rCD154 or CFZ533 for 3 hours at 37° C. or 4° C. FIG. 8B. Relative internalization erode of CFZ533 and rCD154 under permissive conditions (non-permissive erode values subtracted). Each dot represents data from an individual experiment and the population mean is indicated as a horizontal red line. FIG. 8C. Representative images of individual CD40 expressing or CD40 knock-out RI-1 cells cultured with Alexa488 labeled CFZ533 for 3 hours at 37° C. In all experiments, cells were co-stained with AlexaFlour 647 labeled CD45 to demark the cell membrane.

Pharmacokinetic Properties of CFZ533 in Non-Human Primates

Figure 9:
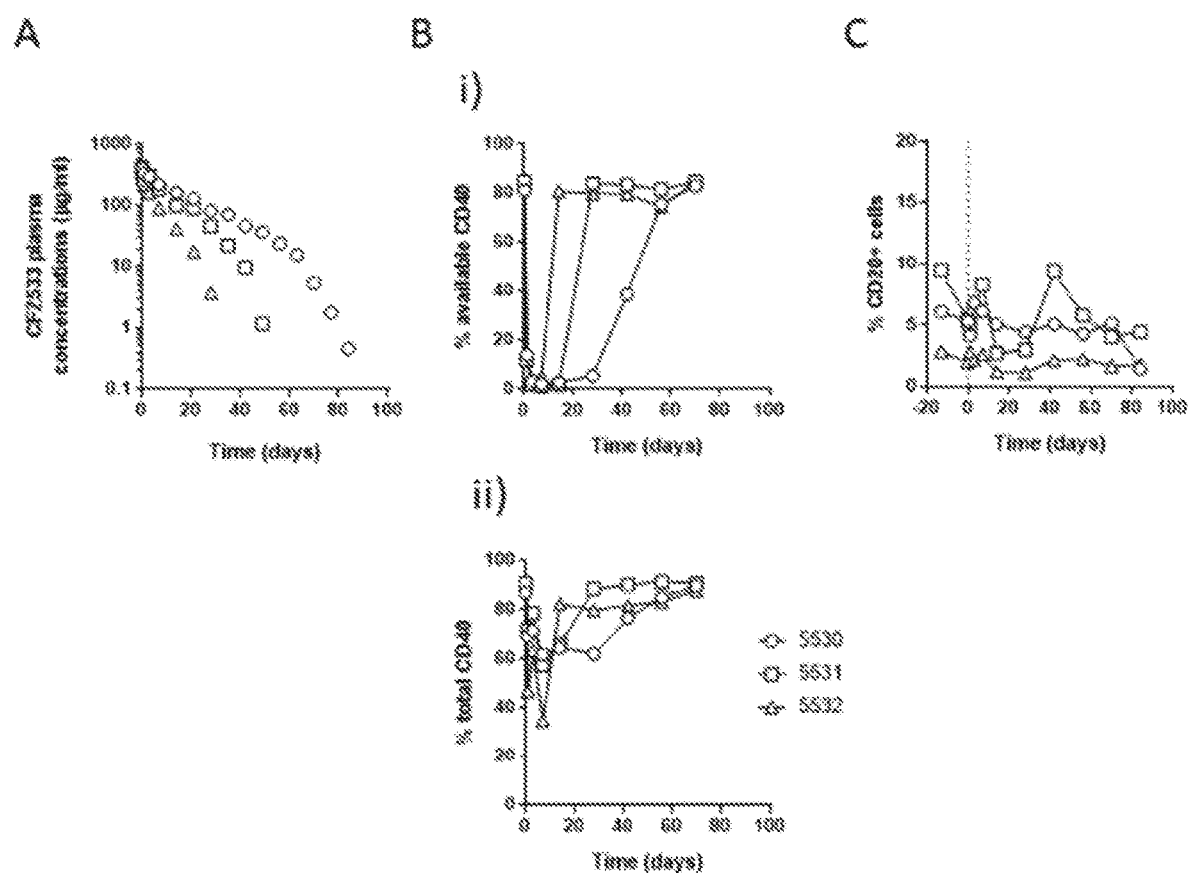
FIG. 9 is graphs showing pharmacokinetic properties of CFZ533 in non-human primates.

FIG. 9A. Serum concentrations of CFZ533 in three cynomolgus monkeys after single dose administration at calculated doses of 16.2 (5532), 18.5 (5531) and 20 (5530) mg/kg intravenously. FIG. 9B. CD40 occupancy: percent available CD40 (i) and percent total CD40 (ii) C. Peripheral B/T cells: percentage of peripheral blood B cells after single dose. Day 0 is when CFZ533 was administered.

Data above indicated that CFZ533 bound NHP CD40, and could inhibit rCD154-induced activation of NHP B cells with similar potencies. This suggested that cynomolgus and rhesus monkeys would be suitable species for in vivo studies investigating the relationship between CFZ533 PK and PD. Data in FIG. 9A shows the PK profiles of three cynomolgus monkeys following a single intravenous dose of CFZ533 (calculated doses of 16.2, 18.5 and 20 mg/kg). Typical for a monoclonal antibody targeting an internalizing membrane bound antigen (Mager et al. 2006 and Ng et al. 2006), the time course of CFZ533 concentration exhibited clear target-mediated disposition, resulting in non-linear PK profiles and concentration-dependent clearance rate and half-life. The inflection point observed in the PK profiles is a marker of target engagement and is associated with an increased contribution of CD40 to the overall clearance of CFZ533, and a shorter half-life. Further, the inflection point in the PK profiles coincided with the time where a drop of CD40 saturation was observed (FIG. 9B, i). This occurred at approximately 10-20 µg/ml, when CFZ533 was subject to more rapid elimination. In all animals, there was no loss of CD40 receptor expression on cells (FIG. 9B, ii). Further, CFZ533 did not deplete peripheral blood B cells (FIG. 9C) or T cells (data not shown), despite some observed variations throughout the study.

CFZ533 Inhibits Recall T Cell-Dependent Antibody Production

Figure 10:
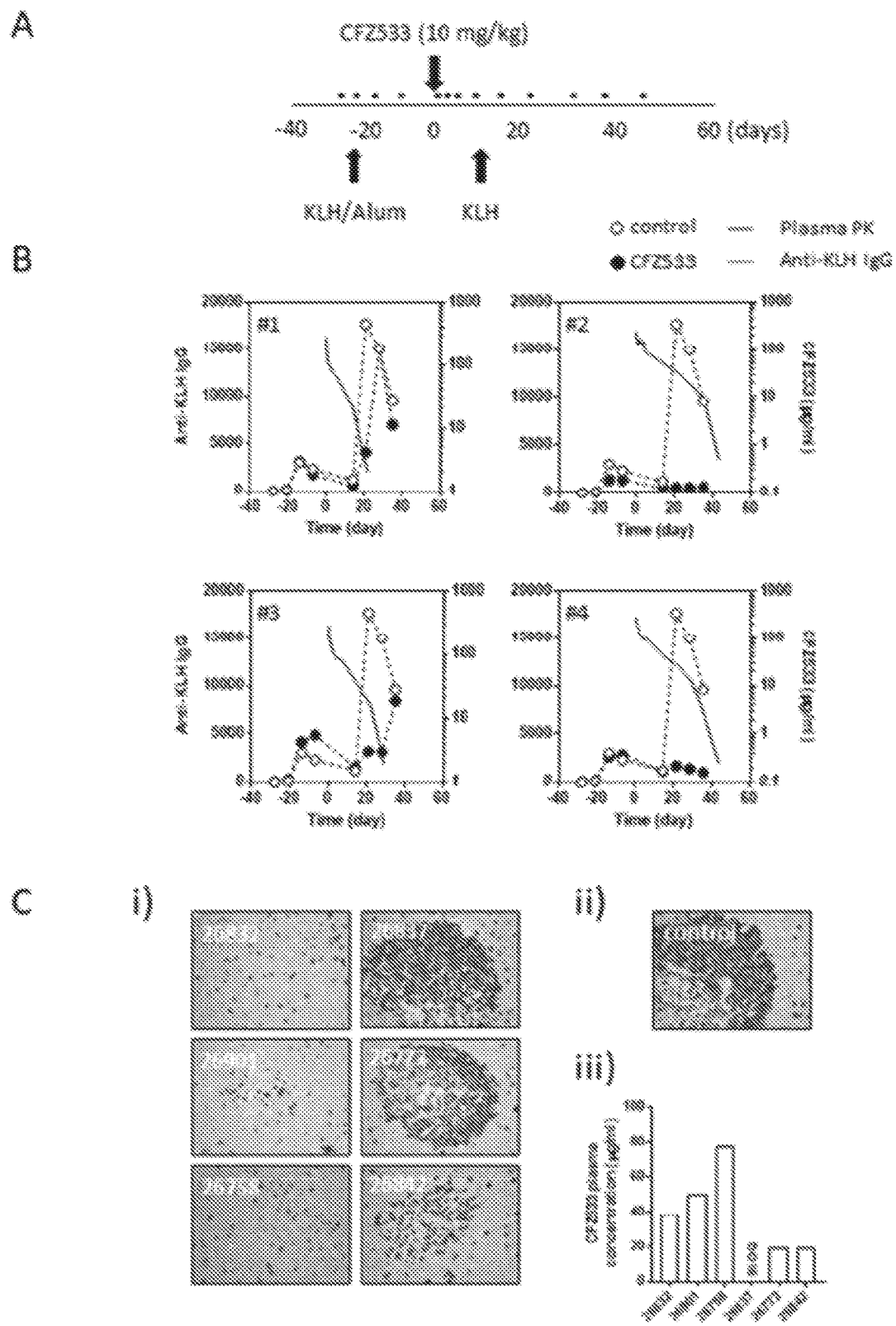
FIG. 10A is an experimental design schematic.
FIG. 10B is graphs showing anti-KLH IgG and plasma CFZ533 levels.
FIG. 10C shows results of a histological analysis.

FIG. 10A shows experimental design schematic for evaluating the effect of CFZ533 on recall TDARs. Arrows below the x-axis highlight primary and secondary KLH immunizations. The timing of a single dose of 10 mg/kg CFZ533 is shown above. The asterisks indicate time points at which anti-KLH IgG and/or CFZ533 levels were measured. FIG. 10B. Each graph shows anti-KLH IgG (closed symbols) and plasma CFZ533 levels (log-scale; unbroken line) for an individual animal. Average anti-KLH IgG levels from control animals (open symbols) are overlaid on each graph for comparative purposes. FIG. 10C. Histological analysis of germinal centers (Ki67 staining) in mLNs from Rhesus monkeys from a 1 mg/kg/week subcutaneous multiple dose 26-week study using CFZ533. Representative mLN sections from six animals are shown (i) along with a control image (ii). iii. Average steady state CFZ533 serum concentrations over a dosing interval from individual animals at the end of the treatment period.

An expected on-target, PD effect of CD40 blocked is inhibition of a TDAR (Kawabe et al. 1994). CFZ533 inhibits primary TDARs in NHPs and humans, and we also wanted to examine the effects of this antibody on a recall TDAR. The experimental design is summarized in FIG. 10A. Briefly, four rhesus monkeys were immunized with KLH in Alum at study day −28 (priming), prior to a single intravenous dose of CFZ533 at 10 mg/kg on study day 1, followed by a second KLH immunization on study day 15.

FIG. 10B illustrates the effects of CFZ533 on anti-KLH IgG recall responses in four individual animals in comparison to data from immunized controls (no CFZ533). There was inter-animal variability in PK profiles of CFZ533, with more rapid elimination of CFZ533 observed in animals #1 and #3. Higher plasma concentrations were observed for a longer period of time in animals #2 and #4. Interestingly, these animals displayed complete suppression of an anti-KLH IgG (and IgM; data not shown) recall response on study day 15 (note all animals mounted a primary TDAR to KLH). In contrast, anti-KLH IgG responses were observed (albeit with some delay) in animals with more rapid clearance of CFZ533 (higher delay for animal #3 as compared to animal #1), notably when serum CFZ533 levels were less than approximately 40 µg/ml at the time of second KLH immunization. As has been observed with previous in vivo experiments with CFZ533 in transplanted (Cordoba et al. 2015) and nontransplanted animals (FIG. 9B), no peripheral B cell depletion was observed (data not shown).

The above results indicated that CFZ533 serum concentrations higher than approximatively 40 µg/ml were required for complete suppression of a recall TDAR in NHPs. We wanted to further examine the relationship between CFZ533 exposure and CD40 pathway-relevant tissue pharmacodynamic effects. At the termination of a 26-week toxicology study, at 1 mg/kg/week CFZ533 subcutaneously we performed histological and molecular analysis of GCs in mesenteric lymph nodes (mLNs). FIG. 10C (i) indicates that of the six animals dosed, we could observe complete suppression of GCs in three individuals, whereas GCs could still be observed in the mLNs of the remaining animals. FIG. 10C (iii) indicates that serum concentrations of at least 38 µg/mL (average steady-state concentration over the dosing interval) were associated with complete suppression of GC development in cortical B cell areas of lymph nodes, whereas incomplete (animal 26842) or no suppression (animals 26772 and 26837) of GCs was observed at serum concentrations below 20 µg/mL, despite full CD40 occupancy on whole blood CD20P" B cells (animals 26842 and 26772; data not shown). There was no evidence of peripheral B cell depletion (data not shown).

DISCUSSION

CFZ533 is being developed as a potential therapy for solid organ transplantation and autoimmune diseases associated with dysregulation of the CD40-CD154 co-stimulatory pathway. Here we describe the characterization of the functional properties of CFZ533 in CD40-pathway relevant in vitro and in vivo model systems as well as investigating the relationship between CFZ533 exposure and PD effects.

CFZ533 was able to bind CD40 and completely prevent rCD154-induced pathway activation on different human immune cell types including B cells and DCs. In addition, it appears that in excess of 90% CD40 occupancy was required for CFZ533 to completely block pathway activation in whole blood. Collectively these data suggested that CFZ533 has the potential to block CD40 pathway-dependent effector functions irrespective of cell type, assuming sufficient receptor occupancy was achieved. Our data also indicated that in PBMCs, CFZ533 was able to displace pre-bound rCD154 from CD40 suggesting that the epitopes of the mAb and physiological ligand may overlap; a notion under investigation in structural studies.

In vivo, a concentration-dependent clearance rate and half-life was observed for CFZ533 in single dose PK studies. This PK profile suggested that CD40 receptor expression affected the elimination of CFZ533. At low CFZ533 concentrations (i.e. incomplete target saturation), the contribution of CD40 to the overall clearance of CFZ533 was elevated and the half-life was somewhat shorter than usually observed for IgG1 type antibodies. At higher concentrations corresponding to complete target saturation (and full functional pathway inhibition), the contribution of the receptor to the overall clearance of CFZ533 was limited and the half-life was increased. The target-mediated clearance of CFZ533 was consistent with CD40-mediated internalization of CFZ533 observed in vitro, that is likely followed by lysosomal degradation of the complex.

An additional finding from the PK/PD studies confirmed the inability of CFZ533 to deplete peripheral B cells in vivo (Cordoba et al. 2015). As mentioned, the inability of CFZ533 to deplete CD40 expressing cells is due to the presence of a N297A mutation in the antibody leading to the absence of N-linked glycosylation in the hinge region, rendering it unable to bind FcγRIIIA or mediate ADCC or CDC. Fc-silencing of CFZ533 was done to prevent depletion of CD40-expressing cell types; of particular concern given the broad tissue distribution of this receptor on immune and non-immune cell types, particularly under inflammatory conditions.

In addition to efficacy in NHP renal transplantation (Cordoba et al. 2015), results disclosed herein indicated that CFZ533 completely inhibited recall TDARs. This result suggested that memory B cell responses to T cell-dependent antigens were fully dependent on CD40-CD154 interactions. The extent of inhibition of the recall response appeared to be related to the concentration of CFZ533, with serum levels in excess of 30-40 µg/ml (for at least a week after boosting) being required for full suppression of an antigen-specific antibody response. This relationship between serum concentration and a CD40 pathway-relevant tissue PD readout also held when examining the effect of CFZ533 on mesenteric lymph node GCs, where a minimum threshold of average, steady-state serum CFZ533 concentrations was required for complete suppression of GCs. These data point to the importance of establishing a relationship between peripheral drug exposures and a target-relevant PD effect in tissue in order to inform dosing strategies. Several biologics targeting the CD40-CD154 costimulation pathway are being developed for various autoimmune diseases. In addition to anti-CD40 mAbs like CFZ533, anti-CD154 mAbs remain in the clinic, despite the potential risk for thromboembolic events (Boumpas et al., 2003). Recent results have suggested that Fc-silencing and pegylated F(ab')2 approaches may eliminate the thromboembolic liabilities of antibodies targeting CD154, however there are reports that Fc-silent anti-CD154 mAbs may be less efficacious. To date there is no evidence of thromboembolic events associated with administration of multiple anti-CD40 antibodies in preclinical models or in the clinic.

In conclusion, our data indicate that CFZ533 is a pathway blocking, non-depleting anti-CD40 antibody with minimal agonistic properties. At sufficient, pharmacologically relevant exposures, CFZ533 is able to completely inhibit recall TDARs as well as suppress germinal centers without depleting CD40 expressing cell types. These data, combined with preclinical efficacy in kidney transplantation provide solid scientific rationale for the potential clinical utility of CFZ533 in select autoimmune diseases and solid organ transplantation, like kidney transplantation, liver transplantation, heart transplantation, lung transplantation, pancreas transplantation, intestine transplantation or composite tissue transplantation.

Nonhuman Primate Studies: CFZ533 Preserves the Quality of Transplanted Kidney Grafts The goal of the present study was to assess, in a NHP model of kidney allograft rejection, the beneficial effects of CFZ533 when given as a monotherapy or in combination with Cyclosporine A.

Nonhuman primates (NHP) have been used as a model of kidney allograft rejection. Recipient NHP were transplanted with life-supporting kidney allografts. The Kidney transplantation and postoperative monitoring was performed using standard techniques (e.g. as described in Cordoba F et al, 2015). The animals were treated weekly with the study drugs CFZ533 (after loading dose on day −1, 0 and 1) and daily with Cyclosporine A (CsA) (e.g. Sandimmun Neoral®, Novartis). CsA for oral administration was a microemulsion preconcentrate (Sandimmun Neoral® drink solution, 100 mg/ml, Novartis Pharma AG and Sandimmun® concentrate for infusion, 50 mg/ml, NovartisPharma AG). The treatments started 1 day prior to Transplantation (Tx). All collected tissues (graft biopsies or at necropsy, Table 2-5) were examined macroscopically and fixed in 4% buffered formalin. After dehydration, they were embedded in paraffin wax. Three µm-thick sections were cut from paraffin blocks and stained with hematoxylin and eosin (HE), Periodc Acid Schiff (PAS), trichrome and Verhoeff-van Gieson stain. The biopsies and necropsies samples were scored according to the Banff15 classification of renal allograft pathology (Loupy 2017). The Banff grading did not include C4d score).

The cynomolgus monkeys (*Macaca fascicularis*) used in this study were captive bred (SICONBREC Inc, Makati City, Philippines) young adults and had normal hematology, serum/urine chemistry and were negative for tuberculosis, *Salmonella/Shigella*, viral infections (Herpes B, STLV, SIV, SRV type D, Hepatitis B), and ecto- and endo-parasites. Only one animal was obtained from, Nafovanny, Long Thanh, Vietnam.

TABLE 11

| Therapy | n | Days after Transplantation (median days) |
|---|---|---|
| CsA 10 mg/kg/d s.c. | 2 | 121 |
| CsA 150/100 mg/kg/d p.o. (per os) | 3 | 113 |
| CsA 20 mg/kg/d p.o. | 5 | 7 |
| CFZ533 30 mg/kg i.v. + CsA 20 mg/kg/d p.o. | 5 | 94 |
| CFZ533 30 mg/kg i.v. monotherapy | 5 | 95 |
| CsA 150/100 mg/kg/d p.o. | 5 | 150 |

Days after transplantation refers to the timepoint at which biopsies have been taken for further analysis. For s.c. application of CsA Sandimmun® was used; for p.o application of CsA Sandimun Neoral® was used. The CsA dose 20 mg/kg p.o. is considered to a non-efficacious dose.

Figure 15:
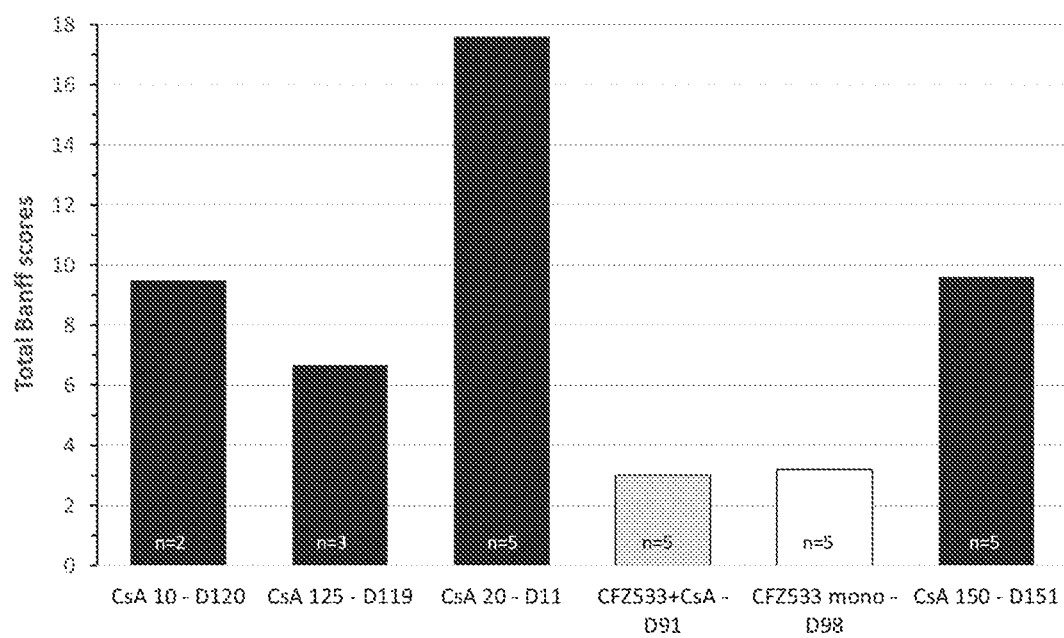
FIG. 15 shows the Banff scores obtained in a Nonhuman primates (NHP) kidney transplantation study. NHP were treated post transplantation with CsA (Sandimmun®, Novartis/Sandimmun Neoral®, Novartis), CFZ533 and combination of CFZ533 with CsA. Total Banff scores are shown.

When applied as combination therapy with CsA (20 mg/kg p.o.) or as a monotherapy, CFZ533 demonstrated efficacy in increasing the survival of kidney allografts in NHPs and well preserved graft morphology as illustrated by the total Banff scores (FIG. 15). In conclusion, the results of the study support the use of CFZ533 as a valid treatment for the prevention of kidney graft rejection as a monotherapy or in combination therapies. In addition, such combination treatment shows an excellent safety profile.

Calcineurin (CNI)-Free Therapy with CFZ533 Preserves the Quality of Transplanted Kidney Grafts.

Figure 16:
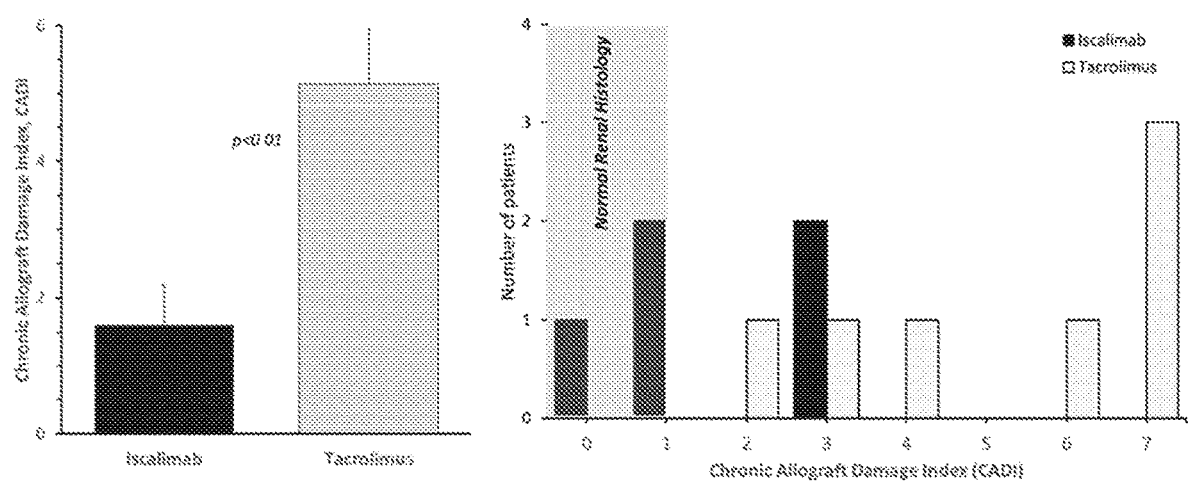
FIG. 16 shows biopsy data obtained from five patients treated with CFZ533 continuously for up to 25 months and from seven patients treated with tacrolimus for the same period (CCFZ533X2201, not disclosed herein). The quality of the graft was estimated using the Chronic Allograph Damage Index (CADI) (Isoniemi et al. 1992 and 1994), where scores of ≤1 reflects normal renal histology and higher scores correlate with poor long-term outcome (Hayry et al. 2004, Yilmaz et al. 2007, Yilmaz et al. 2003). Pristine renal histology was found in 3 of 5 patients on iscalimab (60%) and in none of the 7 treated with tacrolimus (0%). The average CADI was 1.60±0.60 for CFZ533 (n=5) vs. 5.14±0.80 for tacrolimus (n=7), (mean±SEM, p<0.01 using Student t)
Figure 17:
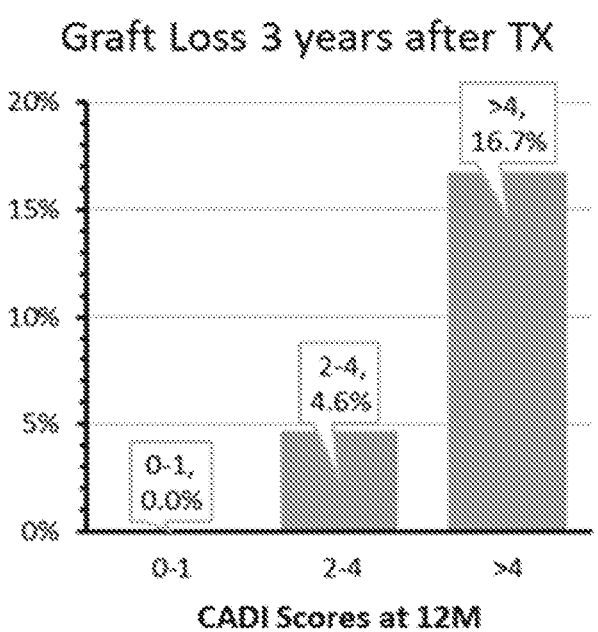
FIG. 17 is taken from Yilmaz, S. et al. 2003 (Protocol core needle biopsy and histologic Chronic Allograft Damage Index (CADI) as surrogate end point for long-term graft survival in multicenter studies. J Am Soc Nephrol, 14(3), pp. 773-9) and illustrates the link between low CADI scores and graft survival/loss after transplantation

A PoC Study in de Novo Renal Transplantation (CCFZ533X2101/NCT02217410) using CFZ533 was performed. In this multicenter randomized controlled trial, CFZ533 showed improved renal function compared to tacrolimus. Allograft biopsies were performed on a subset of study patients. A pathologist, blinded to therapy, reviewed and scored all biopsy slides using the established Banff criteria and calculated the chronic allograft damage index (CADI, Nickerson P et al., Legendre C et al., Seron D et al.,). A CADI of 1 or less was considered as 'normal renal histology'. Two patients were excluded from the analysis, since they switched therapy after only 2 months. The results of the trial are shown in FIG. 16. The results show that three of five patients (60%) on CFZ533 had 'normal renal histology' versus none of seven on tacrolimus, p<0.01. The average CADI at final biopsy was 1.6±0.6 for CFZ533 and 5.1±0.8 for tacrolimus, p<0.01.

Conclusion: Compared to current standard-of-care, CFZ533 appears to be associated with lower CADI scores, with close to normal histology maintained in a high proportion of allografts and, hence CFZ533 has the potential to improve long-term outcomes of solid organ transplantations. These findings confirm observations in the nonhuman primates. The CADI scores are directly correlated to the graft loss/graft survival after transplants. A normal renal histology, as measured by the CADI score (Yilmaz et al., 2003), after transplantation as a results of the CFZ533 treatment provides a method of ensuring long term graft survival in transplant patients.

REFERENCES

Boumpas D T, Furie R, Manzi S, Illei G G, Wallace D J, Balow J E et al. A short course of BG9588 (anti-CD40 ligand antibody) improves serologic activity and decreases hematuria in patients with proliferative lupus glomerulonephritis. Arthritis Rheum 2003; 48(3):719-727.

Clatworthy M R (2011) Targeting B cells and antibody in transplantation. Am J Transplant; 11: 1359-67.

Contin C, Pitard V, Delmas Y, et al (2003) Potential role of soluble CD40 in the humoral immune response impairment of uraemic patients. Immunology; 110(1):131-40.

Cordoba F, Wieczorek G, Audet M, Roth L, Schneider M A, Kunkler A et al. A novel, blocking, Fcsilent anti-CD40 monoclonal antibody prolongs nonhuman primate renal allograft survival in the absence of B cell depletion. Am J Transplant 2015; 15(11):2825.

Harland R, Klintmalm G, Yang H, et al. (2015) ASKP1240 in De Novo Kidney Transplant Recipients. Am J Transplant; 15(S3):Abstract #3012.

P. Hayry, T. Paavonen, E. Taskinen, E. Tomlanovich, T. Mathew, M. Navarro, E. Ramos, L. Hooftman, J. Vamvakopoulos, E. Aavik, and S. Yilmaz. Protocol Core Needle Biopsy and Histological Chronic Allograft Damage Index as Surrogate Endpoint for Long-Term Graft Survival. Transplantation Proceedings, 36, 89_91 (2004)

Kasiske B L, Israni A K, Snyder J J, et al (2011) The relationship between kidney function and long-term graft survival after kidney transplant. Am J Kidney Dis; 57(3): 466-75.

Kawabe T, Naka T, Yoshida K, Tanaka T, Fujiwara H, Suematsu S et al. The immune responses in CD40-deficient mice: impaired immunoglobulin class switching and germinal center formation. Immunity 1994; 1(3):167-178.

Komaroff A L, Fagioli L R, Doolittle T H, et al (1996) Health status in patients with chronic fatigue syndrome and in general population and disease comparison groups. Am J Med; 101:281-90.

Komura K, Fujimoto M, Matsushita T, et al (2007) Increased serum soluble CD40 levels in patients with systemic sclerosis. J Rheumatology; 34(2):353-8.

Kuenstner S, Langelotz C, Budach V, et al (2002) The comparability of quality of life scores. A multitrait multimethod analysis of the EORTC QLQ-C30, SF-36 and FLIC questionnaires. Eur J Cancer; 38:339-48.

Helena m. Isoniemi, Leena Krogerus, Eeva von Willebrand, Eero Taskinen, Juhani Ahonen, and Pekka Hayry: Histopathological findings in well-functioning, long-term renal Allografts, Kidney International, Vol. 41(1992), pp. 155-160. Helena Isoniemi, Eero Taskinen, and Pekka Hayry: Histological chronic allograft damage index accuratelly predicts chronic renal allograft rejection. Transplantation Vol 58, No. 11, 1195-1198, 1994

Legendre C, Thervet E, Skhiri H, Mamzer-Bruneel M F, Cantarovich F, Noel L H, Kreis H: Histologic features of chronic allograft nephropathy revealed by protocol biopsies in kidney transplant recipients. Transplantation 65: 1506-1509, 1998

Lowe P J, Tannenbaum S, Wu K, et al (2010) On setting the first dose in man: quantitating biotherapeutic drug-target binding through pharmacokinetic and pharmacodynamic models. Basic & Clinical Pharmacology & Toxicology; 106(3):195-209.

Loupy A, Haas M, Solez K, et al (2017) The Banff 2015 kidney meeting report: Current challenges in rejection classification and prospects for adopting molecular pathology. Am J Transpl; 17: 28-41.

Mager D E. Target-mediated drug disposition and dynamics. Biochem Pharmacol 2006; 72(1): 1-10.

Matas A J, Smith J M, Skeans M A, et al (2013) OPTN/SRTR Annual Data Report: Kidney. Am J Transplant; 13(Suppl 1):11-46.

Naesens M, Kuypers D R and Sarwal M (2009) Calcineurin inhibitor nephrotoxicity. Clin J Am Soc Nephrol; 4(2): 481-508.

Ng C M, Stefanich E, Anand B S, Fielder P J, Vaickus L. Pharmacokinetics/pharmacodynamics of nondepleting anti-CD4 monoclonal antibody (TRX1) in healthy human volunteers. Pharm Res 2006; 23(1):95-103.

Nickerson P, Jeffery J, Gough J, McKenna R, Grimm P, Cheang M, Rush D: Identification of clinical and histopathologic risk factors for diminished renal function 2 years posttransplant. J Am Soc Nephrol 9: 482-487, 1998

Schwabe R F, Engelmann H, Hess S, et al (1999) Soluble CD40 in the serum of healthy donors, patients with chronic renal failure, haemodialysis and chronic ambulatory peritoneal dialysis (CAPD) patients. Clin Exp Immunol; 117(1):153-8.

Seron D, Moreso F, Bover J, Condom E, Gil-Vernet S, Canas C, Fulladosa X, Torras J, Carrera M, Grinyo J M, Alsina J: Early protocol renal allograft biopsies and graft outcome. Kidney Int 51: 310-316, 1997.

Th'ng K H, Garewal G, Kearney L, Rassool F, Melo J V, White H et al. Establishment and characterization of three new malignant lymphoid cell lines. Int J Cancer 1987; 39(1):89-93.

van Kooten C and Banchereau J (2000). CD40-CD40 ligand. J Leukoc Biol; 67(1):2-17.

Warncke M, Calzascia T, Coulot M, Balke N, Touil R, Kolbinger F et al. Different adaptations of IgG effector function in human and nonhuman primates and implications for therapeutic antibody treatment. J Immunol 2012; 188(9):4405-4411.

Serdar Yilmaz, Steven Tomlanovich, Timothy Mathew, Eero Taskinen, Timo Paavonen, Merci Navarro, Eleanor Ramos, Leon Hooftman, Pekka Hayry. Protocol Core Needle Biopsy and Histologic Chronic Allograft Damage Index (CADI) as Surrogate End Point for Long-Term Graft Survival in Multicenter Studies. J Am Soc Nephrol 14: 773-779, 2003.

Serdar Yilmaz, Kevin McLaughlin, Timo Paavonen, Eero Taskinen, Mauricio Monroy, Einari Aavik, Joannis Vamvakopoulos, and Pekka Häyry. Clinical Predictors of Renal Allograft Histopathology: A Comparative Study of Single-Lesion Histology Versus a Composite, Quantitative Scoring System. Transplantation Volume 83, Number 6, Mar. 27, 2007

The invention claimed is:

1. A method of inhibiting CD40-mediated graft rejection in kidney transplantation in a human subject in need thereof, comprising administering a therapeutically effective dose of anti-CD40 antibody to said subject,
wherein the anti-CD40 antibody is administered through a loading dosing and a maintenance dosing, and wherein the loading dosing comprises one, two, three or four intravenous administration(s) of a first dose and the maintenance dosing comprises weekly or biweekly subcutaneous injections of a second dose, and wherein the first dose is at least 10 mg and up to 30 mg anti-CD40 antibody per kg of the subject and the second dose is between 300 mg and 600 mg anti-CD40 antibody, and
wherein the antibody comprises the heavy chain amino acid sequence of SEQ ID NO: 9 and the light chain amino acid sequence of SEQ ID NO: 10 or the heavy chain amino acid sequence of SEQ ID NO: 11 and the light chain amino acid sequence of SEQ ID NO: 12.

2. The method according to claim 1 wherein the loading dose comprises one dose of at least 10 mg and up to 30 mg of the anti-CD40 antibody per kg of the subject, administered intravenous one time on day 1, is followed by a maintenance dose which comprises unit doses of at least 300 mg administered subcutaneous weekly or bi-weekly.

3. The method of treatment according to claim 1, wherein the antibody comprises the heavy chain amino acid sequence of SEQ ID NO: 9 and the light chain amino acid sequence of SEQ ID NO: 10.

4. The method according to claim 1, 2, or 3, wherein the antibody is administered together with one or more pharmaceutically acceptable carriers.

* * * * *